US011414374B2

(12) United States Patent
Lourenço et al.

(10) Patent No.: US 11,414,374 B2
(45) Date of Patent: Aug. 16, 2022

(54) CRYSTALLINE FORMS OF VILANTEROL TRIFENATATE AND PROCESSES FOR THEIR PREPARATION

(71) Applicant: Hovione Scientia Limited, Cork (IE)

(72) Inventors: Nuno Torres Lourenço, Lisbon (PT); Luis Sobral, Montijo (PT); Joana Fernandes, Lançada (PT)

(73) Assignee: Hovione Scientia Limited, Cork (IE)

( * ) Notice: Subject to any disclaimer, the term of this patent is extended or adjusted under 35 U.S.C. 154(b) by 66 days.

(21) Appl. No.: 16/631,685

(22) PCT Filed: Jul. 9, 2018

(86) PCT No.: PCT/GB2018/051939
§ 371 (c)(1),
(2) Date: Jan. 16, 2020

(87) PCT Pub. No.: WO2019/016511
PCT Pub. Date: Jan. 24, 2019

(65) Prior Publication Data
US 2020/0148626 A1 May 14, 2020

(30) Foreign Application Priority Data
Jul. 19, 2017 (PT) .......................................... 110209

(51) Int. Cl.
*C07C 217/08* (2006.01)
*A61P 11/06* (2006.01)
(Continued)

(52) U.S. Cl.
CPC .......... *C07C 217/08* (2013.01); *A61K 31/138* (2013.01); *A61P 11/00* (2018.01);
(Continued)

(58) Field of Classification Search
CPC ... C07C 217/08; C07C 213/10; C07C 215/60; C07C 213/00; A61P 11/06; A61P 11/00; A61K 31/138; C07B 2200/13
(Continued)

(56) References Cited

U.S. PATENT DOCUMENTS 7,361,787 B2    4/2008  Box et al.
2017/0189424 A1 7/2017  Barnes et al.

FOREIGN PATENT DOCUMENTS

JP  2005511508 A  4/2005
PT     110209 A   7/2017
(Continued)

OTHER PUBLICATIONS

Foreign communication from a related application—Examination Report of Indian Patent Application No. 202017004658, dated Jul. 12, 2021, 7 pages.
(Continued)

*Primary Examiner* — Taylor V Oh
(74) *Attorney, Agent, or Firm* — Conley Rose, P.C.; Rodney B. Carroll

(57) ABSTRACT

The present invention relates to new crystalline forms of vilanterol trifenatate, processes for their preparation, and their use in a pharmaceutical composition for the treatment of respiratory diseases, particularly for the treatment of asthma and chronic obstructive pulmonary disease. In particular, the present invention relates to a crystalline form of vilanterol trifenatate characterised in that the form has an XRPD pattern as defined herein having characteristic diffraction angles (2-theta or 2θ (°)) falling within or at each end of one or more of the following ranges: (a) 3 to 5°, such as 3.8 to 4.4°; and/or (b) 7 to 9.9°, such as 7 to 8.5°; and/or
(Continued)

(c) 12 to 13.3°, such as 12 to 13.3'; and/or (d) 16.4 to 17.3°, such as 16.4 to 17.3'; and/or (e) 26.8 to 28.3°, such as 26.8 to 28.3°.

18 Claims, 13 Drawing Sheets

(51) Int. Cl.
*A61P 11/00* (2006.01)
*A61K 31/138* (2006.01)
*C07C 213/10* (2006.01)
*C07C 215/60* (2006.01)

(52) U.S. Cl.
CPC ............ *A61P 11/06* (2018.01); *C07C 213/10* (2013.01); *C07C 215/60* (2013.01); *C07B 2200/13* (2013.01)

(58) Field of Classification Search
USPC .......................................................... 514/172
See application file for complete search history.

(56) References Cited

FOREIGN PATENT DOCUMENTS

| WO | 2003024439 A1 | 3/2003 |
|---|---|---|
| WO | 2014041565 A2 | 3/2014 |
| WO | 2017001907 A1 | 1/2017 |
| WO | 2019016511 A2 | 1/2019 |

OTHER PUBLICATIONS

Relvar Ellipta Assessment Report, European Medicines Agency, Committee for Medicinal Products for Human Use (CHMP), Sep. 19, 2013, 279 pages.
"Crystalline forms of Vilanterol base and vilanterol trifenatate", Research Disclosure, 2014, pp. 772-773, vol. 604, Industrial Opportunities, Limited.
Foreign communication from related application—International Search Report, application No. PCT/GB2018/051939, dated Feb. 8, 2019, 5 pages.
Foreign communication from related application—International Preliminary Reporton Patentability, International Application No. PCT/GB2018/051939, dated Oct. 15, 2019, 7 pages.
Murikipudi, Vasudha et al., "Efficient throughput method for hygroscopicity classification of active and inactive pharmaceutical ingredients by water vapor sorption analysis", Pharmaceutical Development and Technology, 2013, pp. 348-358, vol. 18, No. 2, Informa Healthcare USA, Inc.
Procopiou, Panayiotis A. et al., "Synthesis and Structure Activity Relationships of Long-acting β2 Adrenergic Receptor Agonists Incorporating Metabolic Inactivation: An Antedrug Approach", Journal of Medicinal Chemistry, 2010, pp. 4522-4530, vol. 53, American Chemical Society.
Foreign Communication from Related Application—Japanese Notice of Reasons for Refusal with English Translation, Japanese Patent Application No. 2020-502459, dated Feb. 4, 2022, 19 pages.
Disclosure 096091 received in Japanese Patent Application No. 2020-502459, dated Feb. 4, 2022—Panayiotis A, Procopiou et al., "Synthesis and structure-activity relationships of long-acting beta2 adrenergic receptor agonists Incorporating metabolic inactivation: an antedrug approach," Journal of Medicinal Chemistry, Jun. 2010, vol. 53, No. 11, pp. 4522-4530, American Chemical Society.
Disclosure 096099 received in Japanese Patent Application No. 2020-502459, dated Feb. 4, 2022—Research Disclosure No. 604002, "Crystalline forms of vilanterol base and vilanterol trilenatate" Aug. 2014, pp. 772-773.
Disclosure 096092 received in Japanese Patent Application No. 2020-502459, dated Feb. 4, 2022—"New Galenical Pharmacy," Nov. 25, 1984, pp. 102-103 and 232-233, ISBN 4-525-77291-3, Nanzando.
Disclosure 096093 received in Japanese Patent Application No. 2020-502459, dated Feb. 4, 2022—"New Introduction to Pharmaceutics," 1987, 3 pages, ISBN 4-524-49209-7, Teisuke Okano.
Disclosure 096094 received in Japanese Patent Application No. 2020-502459, dated Feb. 4, 2022—"API Form screening and selection in drug discovery stage," Pharm Stage, 2007, vol. 6, No. 10, 9 pages.
Disclosure 096095 received in Japanese Patent Application No. 2020-502459, dated Feb. 4, 2022—Yamano, Mitsuhisa, "Approach to Crystal Polymorph in Process Research of New Drug," Journal of Organic Synthetic Chemistry, Jan. 1, 2007, vol. 65, No. 9, pp. 907-913 and 944.
Disclosure 096096 received in Japanese Patent Application No. 2020-502459, dated Feb. 4, 2022—"Science of Pharmaceutical Polymorphism and Crystallization of Pharmaceuticals," Sep. 20, 2002, pp. 1-16 and 273-278, ISBN 4-901689-06-1.
Disclosure 096097 received in Japanese Patent Application No. 2020-502459, dated Feb. 4, 2022—"Sixteenth Revision of Japanese Pharmacopoeia," 2011, pp. 64-68.
Disclosure 096098 received in Japanese Patent Application No. 2020-502459, dated Feb. 4, 2022—NIHON, "Experimental Chemistry Courses (Secondary) 2 Separation and Purification," 1967, pp. 159-178, 186-187.

CRYSTALLINE FORMS OF VILANTEROL TRIFENATATE AND PROCESSES FOR THEIR PREPARATION

CROSS REFERENCE TO RELATED APPLICATIONS

This application is a filing under 35 U.S.C. 371 of International Application No. PCT/GB2018/051939 filed Jul. 9, 2018, entitled "New Crystalline Forms of Vilanterol Trifenatate and Processes for Their Preparation," which claims priority to Portuguese Patent Application No. 110209 filed Jul. 19, 2017, which applications are incorporated by reference herein in their entirety.

DESCRIPTION

The present invention relates to new crystalline forms of vilanterol trifenatate, processes for their preparation, and their use in a pharmaceutical composition for the treatment of respiratory diseases, particularly for the treatment of asthma and chronic obstructive pulmonary disease. These new crystalline forms present advantages compared to known forms, including high purity, and are highly characterized.

BACKGROUND OF THE INVENTION

The compound vilanterol trifenatate, of molecular structure (I) depicted below, is used as an inhaled long-acting $beta_2$-agonist (LABA) for the treatment of respiratory diseases such as bronchial asthma and chronic obstructive pulmonary disease.

Vilanterol trifenatate, designated by 4-((1R)-2-((6-(2-((2,6-Dichlorophenyl)methoxy)ethoxy)hexyl) amino)-1-hydroxyethyl)-2-(hydroxymethyl)phenol triphenylacetate, was first claimed by Glaxo (now GlaxoSmithKline/GSK) in WO 2003/024439 as optically pure (R)-isomer in the form of trifenatate salt. For further reference we designate herein the form described in WO 2003/024439 as form I.

Vilanterol trifenatate is preferably administrated by inhalation, in fixed combination with fluticasone propionate, using the inhaler Breo Ellipta® that delivers powdered vilanterol/fluticasone from foil-wrapped blisters. It is also administrated by inhalation in fixed combination with umeclidinium bromide using the inhaler Anoro Ellipta® that delivers powdered vilanterol/umeclidinium from foil-wrapped blisters. GlaxoSmithKline is currently developing a once-daily 'closed' triple therapy of an inhaled corticosteroids/long-acting beta-2-agonists/long-acting muscarinic antagonist combination (fluticasone furoate/umeclidinium bromide/vilanterol trifenatate in a single device), with the aim of providing a new treatment option for the management of asthma by improving lung function, health-related quality of life and symptom control over established combination therapies (ClinicalTrials.gov; Identifier: NCT03184987).

Vilanterol, as well as certain pharmaceutically acceptable salts thereof and processes for the preparation thereof, are described in both WO 2003/024439 and in J. Med. Chem. 2010, 53 (4522-4530), authored by GSK scientists. The reaction sequence is schematically represented as follows, in which ethanol is used as the solvent at 80° C. in the conversion of vilanterol base to the trifenatate salt:

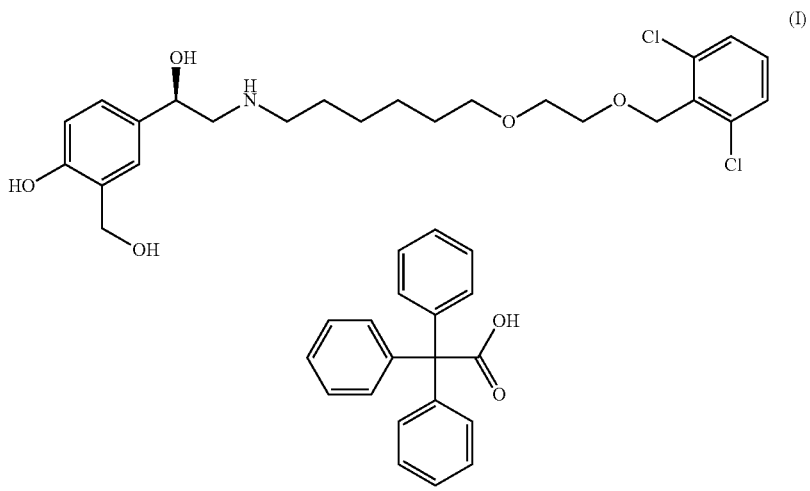 [SMILES: OCc1cc([C@@H](O)CNCCCCCCOCCOCc2c(Cl)cccc2Cl)ccc1O ; O=C(O)C(c1ccccc1)(c1ccccc1)c1ccccc1]

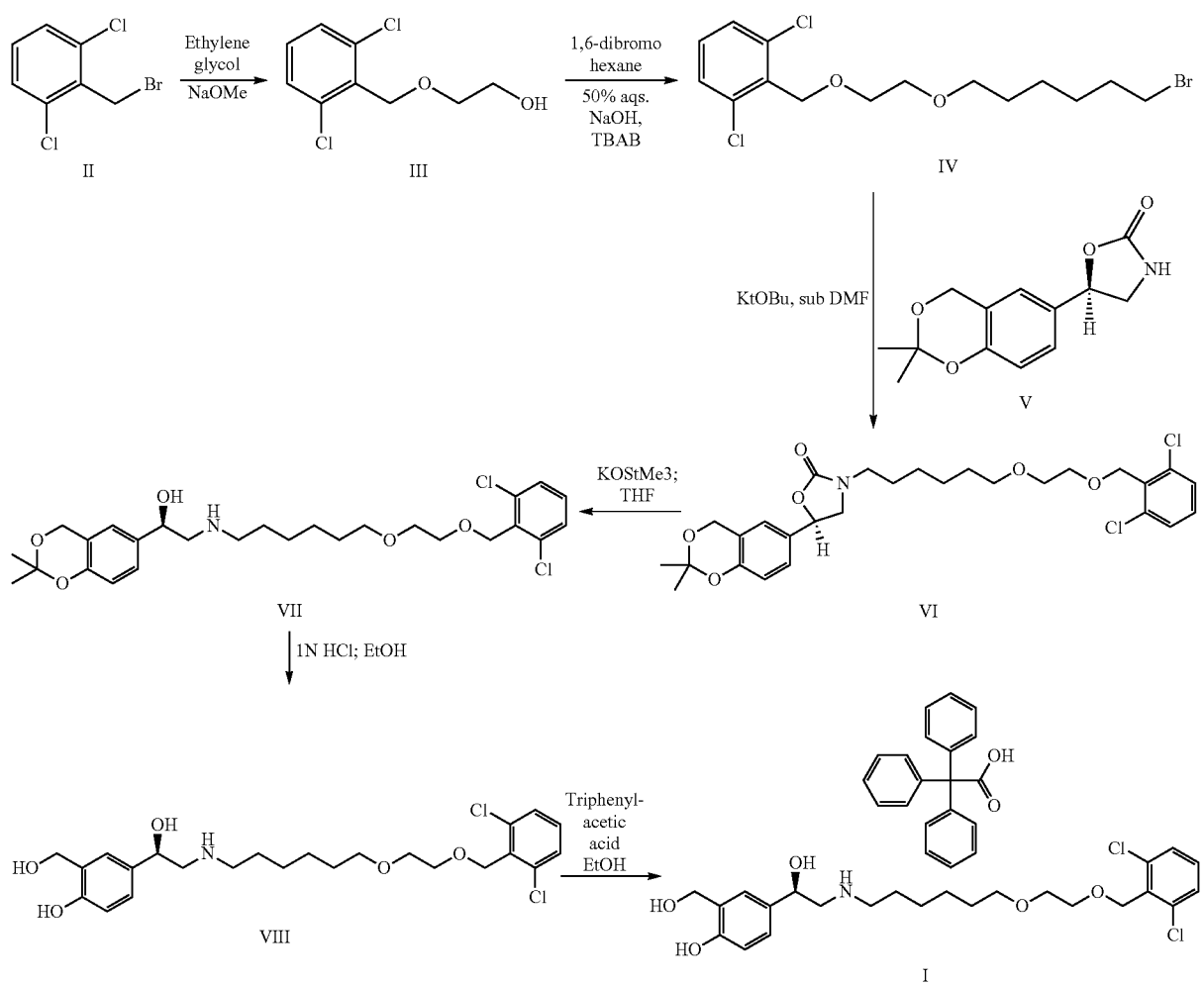

Given the interest in the drug, other companies have experimented with various aspects, including Laurus Labs, who in patent specification no. WO 2014/041565 report preparing vilanterol trifenatate using the process disclosed in the GSK specification referred to above, which resulted in a higher than desired level of impurity. They tried performing reactions in alternative alcoholic solvents such as methanol and isopropanol, but noted that these also did not result in exceptional yields or purity. Instead, they teach using a non-alcoholic solvent, preferably acetone, which results in a decreased impurity profile (greater than 99.5% purity by HPLC; no single impurity greater than 0.1%). No water was used or suggested as solvent or part of a solvent system. In particular, vilanterol trifenatate was prepared by reacting 4-(R)-2-(6-(2-(2,6-dichlorobenzyloxy)-ethoxy)-hexylamino)-1-hydroxyethyl)-2-hydroxymethylphenol (compound VIII) with an acetone solution of triphenyl acetic acid at 50-55° C. (example 13, WO 2014/041565). The product, vilanterol trifenatate, is stated to be 99.79% pure. However, the vilanterol trifenatate crystalline form obtained from this reaction is not elucidated. No other characterising data are given. No indication is given by Laurus that the trifenatate salt prepared by their method is other than the same as that described by Glaxo/GSK, i.e. 'Form I'.

A few years later, Teva described, in WO 2017/001907, a biocatalytic process for the preparation of vilanterol. Additionally, they disclose the preparation of vilanterol in the form of the L-tartrate salt, which can then be converted in a multi-step process via the base (by addition of the corresponding acid) to the trifenatate salt. Again, no indication is given by Teva that the trifenatate salt prepared by their method is other than the same ('Form I') as that described by Glaxo/GSK. Furthermore, WO 2017/001907 discloses the general desideratum that the vilanterol salt (such as tartrate or trifenatate), should be chemically pure, i.e. having no more than 0.25%, preferably no more than 0.15%, more preferably not more than 0.1%, of an impurity designated 'Impurity A'. However, in the example of the preparation of the trifenatate salt using ethanol as solvent together with residual dichloromethane from preparation of the vilanterol base (from the tartrate salt), the chemical purity of the product is given as only 99.8%; accordingly at least 0.2% impurity is present. Therefore, Teva barely achieve their own desideratum and do not disclose how to achieve levels of impurity, particularly of Impurity A, below 0.1%.

Thus, there is a need for a form of the drug that overcomes the currently-recognised disadvantages of form I with respect to characteristics such as purity and hygroscopicity whilst maintaining applicable levels of physical and chemical stability desirable in an active pharmaceutical ingredient.

Meanwhile, an anonymous research disclosure appeared in a publication of Industrial Opportunities Ltd, vol 604(2), pp 772-774 (August 2014) concerning "Crystalline forms of vilanterol base and vilanterol trifenatate". This research disclosure tabulates five hydrates or solvates of vilanterol trifenatate and three anhydrous forms, together with an alleged 'amorphous' form, prepared from the GSK form referred to above (which is also referred to in the research disclosure as 'Form I'). Scant details are provided regarding the process conditions for each except that lists of a variety of alternative solvents or solvent mixtures are provided without specifying relative concentrations, temperatures and other necessary conditions. The research disclosure lists XRPD peaks for nine of their forms and an XRPD graph is provided for two of these.

However, these data are called into question, not least because, when repeating the method described in the research disclosure for the preparation of a form designated therein as 'amorphous', the present inventors found that this product was in fact crystalline and substantially indistinguishable (by XRPD) from the original form I of Glaxo, and also has the same melting point range (by DSC). Accordingly, the research disclosure is insufficient and/or inaccurate in its description and/or characterisation of the forms listed.

Furthermore, no data are provided or given in or inferable from the research disclosure that would indicate that any of the forms prepared therein would solve any of the previously-mentioned problems with form I, or provide a credible alternative for potential use in medicine.

This, coupled with the uncertainties about the molecular rearrangement of vilanterol trifenatate disclosed in these prior art documents, moved the present inventors to develop methods to prepare and identify new crystalline forms of vilanterol trifenatate.

Additionally, some molecular rearrangements of active pharmaceutical ingredients (APIs) often have disadvantageous properties. These properties depend on the solid state and can be modified by changing the solid form by preparing different polymorphs, solvates, hydrates, salts and co-crystals. Therefore, there is a continuing need to obtain new forms having superior characteristics in terms of differentiated solubility, density, particle morphology, flow characteristics, electrostatic charge, low hygroscopicity and/or improved stability that can represent an advantage for APIs with challenging properties.

In particular, drugs for the treatment of respiratory diseases are frequently administered via dry powder inhalation devices. Formulating respiratory drugs as dry powders with inhalation excipients is not a straightforward process. The use of APIs with differentiated properties allows a better preparation of dry powder formulations with proper bioavailability and physical properties. Bioavailability and physical characteristics are important for an efficient administration of the drug substance, to ensure that an effective dose is delivered to the correct part of the lung and that the drug is effective in treating respiratory diseases.

GENERAL DESCRIPTION OF THE INVENTION

On the other hand, the present inventors have identified and characterised a number of novel polymorphic forms, which provide alternatives to form I and also certain benefits over form I, in the context of their potential use in medicine for the same or similar conditions as those known for vilanterol trifenatate.

Especially, the present inventors have developed a method to provide crystalline vilanterol trifenatate comprising less than 0.15%, preferably less than 0.1%, more preferably less than 0.075%, (such as 0.05-0.06%) of Impurity A by HPLC (as described herein). Alternatively, the present inventors provide a method for preparing crystalline vilanterol trifenatate characterised by having a purity by HPLC (as described herein) of more than 99.9%, preferably more than 99.925%, more preferably of about 99.95-99.94% purity by HPLC.

Accordingly, the present invention provides crystalline vilanterol trifenatate comprising less than 0.075%, such as 0.05-0.06%, of Impurity A by HPLC (as described herein). Alternatively, the present invention provies crystalline vilanterol trifenatate characterised by having a purity by HPLC (as described herein) of more than 99.9%, preferably more than 99.925%, purity by HPLC. This is very surprising, given that those researching this important pharmaceutical compound have been attempting to increase its purity for many years and have not yet found a way to produce it at least 99.9% pure, having less that 0.1% Impurity A present.

In particular, these crystalline forms are identifiable as distinct from form I by having common characteristic bands when analysed by X-ray powder diffraction (XRPD, e.g. by using the method described further hereinbelow).

Accordingly, the present invention provides a new crystalline form of vilanterol trifenatate, characterised in that the form has an XRPD pattern having characteristic diffraction angles (2-theta or 2θ(°)) falling within or at each end of one or more of the following ranges:
(a) 3 to 5°; and/or
(b) 7 to 9.9°; and/or
(c) 12 to 13.3°; and/or
(d) 16.4 to 17.3°; and/or
(e) 26.8 to 28.3°.

Thus, each of the polymorphs of the present invention exhibits at least one crystalline peak within one or more of the ranges (a) to (e) (inclusive) defined above, when analysed by XRPD according to the method described hereinbelow. This pattern of peaks is unique to the polymorphs of the present invention when compared with form I, as can be seen from the FIG. 24 hereinbelow.

Preferably, the polymorphs of the present invention exhibit peaks other than those at XRPD 2θ values 3.58°, 4.50°, 10.18° and 14.46°. In other words, this combination of peaks is preferably absent from the polymorphs of the present invention.

Preferably, the present invention provides a new crystalline form of vilanterol trifenatate, characterised in that the form has an XRPD pattern having characteristic diffraction angles (2-theta or 2θ (°)) falling within or at each end of the following ranges:
(a) 3.8 to 4.4°; and/or
(b) 7 to 8.5°; and/or
(c) 12 to 13.3°; and/or
(d) 16.4 to 17.3°; and/or
(e) 26.8 to 28.3°.

More preferred is when the polymorph of the invention is characterised in that the form has an XRPD pattern having characteristic diffraction angles (2-theta or 2θ))(° falling within or at each end of any one or combination of (a), (b), (c) and/or (d) as defined herein, such as a crystal form having characteristic diffraction angles (2-theta or 2θ (°)) falling within or at each end of each (i.e. all) of (a), (b), (c) and (d) as defined herein Especially preferred is a polymorph of the invention characterized by a peak in band (e) as defined hereinbefore. More preferable is when any peak in band (e) is other than in the range of from 28.0 to 28.1, such as 28.02. Also especially preferred is a polymorph of the invention characterized by at least one peak in each of bands (b), (c), (d) and (e) and a peak in band (a) and/or in the range of from 6.9 to 8.5.

Particularly preferred is a polymorph of the invention having at least one peak in more than one of the ranges (a) to (e) specified herein. For example, having at least one peak in:
(i) ranges (c) to (e), inclusive; or
(ii) ranges (b) to (e) inclusive; or
(iii) ranges (b), (c) and (e); or
(iv) ranges (a) to (e) inclusive.

Specifically, the present invention provides a new crystalline form of vilanterol trifenatate, characterised in that the form has an XRPD pattern having characteristic diffraction angles (2-theta or 2θ (°)) as indicated in Table 17 below:

TABLE 17

Compilation of the representative diffraction angles (2Theta) of the X-ray powder diffraction pattern of all vilanterol trifenatate crystalline forms.

Angle 2θ (°)

| Form I | Form II | Form III | Form IV | Form V | Form VI | Form VII | Form VIII | Form IX | Form X | Form XI | Form XII | Form XIII | Form XIV |
|---|---|---|---|---|---|---|---|---|---|---|---|---|---|
| — | — | — | 3.87 | 3.82 | — | — | — | — | — | — | — | — | — |
| — | 4.31 | 4.22 | — | — | — | — | — | — | — | — | — | — | — |
| — | — | — | — | — | — | — | 5.42 | — | 5.35 | — | — | — | — |
| 5.72 | — | — | — | — | 5.70 | — | — | — | — | — | 5.61 | — | — |
| — | — | — | — | — | — | — | 5.81 | — | 5.81 | — | — | — | — |
| — | — | — | — | — | 6.03 | 6.02 | — | 6.01 | — | 6.10 | 6.01 | — | — |
| — | — | — | — | — | — | — | — | — | — | — | — | 6.27 | — |
| — | — | — | — | — | — | — | — | — | 6.34 | — | — | — | — |
| 6.73 | — | — | — | — | — | — | — | — | — | — | — | — | — |
| — | — | — | — | — | — | 6.94 | — | — | — | — | 6.89 | — | — |
| — | — | — | — | — | — | — | 7.03 | 7.04 | — | 7.10 | — | 7.05 | — |
| — | — | — | — | — | — | — | — | — | 7.25 | — | — | — | — |
| — | — | — | — | — | — | — | — | — | 7.48 | — | — | — | — |
| — | — | — | — | — | — | — | — | — | — | — | — | — | 7.51 |
| — | — | — | 7.70 | 7.70 | — | 7.71 | — | — | — | — | — | — | — |
| — | — | — | — | — | — | — | — | — | — | — | — | — | 7.96 |
| — | 8.14 | 8.12 | 8.11 | 8.10 | — | — | — | 8.09 | — | — | — | — | — |
| — | 8.43 | 8.44 | — | — | — | — | — | — | 8.36 | — | — | — | — |
| — | — | — | — | — | — | — | — | — | — | 8.69 | — | — | 8.64 |
| — | — | — | — | 8.72 | — | — | — | — | — | — | — | — | — |
| — | — | — | — | — | — | — | 8.89 | — | — | — | — | — | — |
| — | — | — | — | — | — | 9.26 | 9.29 | 9.26 | — | — | — | — | — |
| — | — | — | — | — | — | — | — | — | — | 9.40 | 9.44 | — | — |
| — | — | — | 9.63 | 9.63 | 9.60 | — | — | — | 9.52 | — | — | — | 9.61 |
| — | — | — | — | — | — | — | 9.80 | — | — | — | 9.76 | — | — |
| 10.07 | — | — | — | — | — | — | — | — | — | — | — | — | — |
| — | 10.59 | — | — | — | — | — | 10.49 | — | — | — | — | — | — |
| — | — | — | — | — | 10.71 | 10.74 | — | — | — | — | 10.77 | — | — |
| — | — | — | — | — | — | — | — | 10.81 | 10.85 | — | — | — | — |
| 10.90 | — | 10.91 | — | — | — | — | — | 10.92 | — | 10.93 | — | — | 10.87 |
| — | 11.09 | — | — | — | 11.15 | 11.01 | — | — | — | — | — | 11.09 | — |
| — | — | — | — | — | — | — | — | 11.23 | — | 11.36 | 11.30 | — | 11.37 |
| — | — | — | — | — | 11.47 | — | — | — | 11.48 | — | — | — | — |
| 11.58 | — | 11.52 | 11.60 | 11.59 | — | — | — | — | — | — | 11.69 | 11.66 | — |
| — | — | — | — | — | — | — | — | 11.71 | 11.77 | — | — | — | — |
| 11.85 | — | 11.89 | — | — | 11.84 | 11.82 | 11.84 | — | — | 11.82 | — | 11.87 | — |
| — | — | — | — | — | 11.95 | — | 12.03 | — | — | — | — | — | — |
| — | — | — | — | — | — | — | — | — | — | 12.15 | 12.11 | — | — |
| — | — | — | 12.32 | 12.31 | — | — | — | — | 12.37 | — | — | 12.29 | — |
| — | — | — | — | — | — | — | 12.48 | — | — | 12.50 | 12.56 | — | 12.56 |
| — | — | — | 12.62 | 12.59 | — | — | — | — | — | — | — | — | — |
| 12.70 | — | 12.69 | — | — | — | — | — | — | — | — | — | — | — |
| — | 12.85 | — | — | — | 12.80 | 12.80 | — | — | — | — | — | — | — |
| — | — | 12.92 | — | — | — | — | — | — | — | — | — | 12.96 | — |
| — | — | 13.10 | 13.16 | — | — | — | — | 13.18 | 13.20 | 13.12 | — | — | 13.28 |
| — | 13.48 | 13.44 | 13.43 | 13.35 | — | — | — | — | — | — | — | 13.40 | — |
| 13.60 | — | — | — | — | 13.62 | — | — | — | 13.68 | — | — | — | — |
| — | 13.81 | — | 13.83 | — | — | — | — | — | — | — | 13.84 | — | 13.86 |
| 14.16 | — | — | — | 14.00 | 14.06 | 14.01 | 13.92 | 14.09 | 14.10 | 14.09 | 14.00 | — | — |
| — | 14.26 | 14.24 | — | — | — | — | 14.25 | — | — | — | 14.36 | — | — |
| — | — | — | — | — | — | — | — | 14.57 | — | — | — | 14.50 | — |
| 14.68 | 14.72 | — | — | — | — | 14.77 | — | — | 14.75 | 14.73 | — | — | — |
| — | — | — | — | — | 14.92 | — | — | — | — | 14.86 | 14.86 | — | — |
| — | — | 14.99 | — | — | — | — | — | 15.06 | — | — | — | — | — |
| 15.24 | — | 15.36 | — | — | — | — | — | — | — | — | — | 15.16 | 15.25 |
| 15.53 | — | — | 15.54 | 15.51 | — | 15.44 | — | — | — | — | — | — | — |
| 15.88 | — | 15.86 | — | — | — | — | — | 15.99 | 15.68 | — | — | — | 15.91 |
| 16.16 | 16.09 | 16.25 | — | 16.11 | 16.20 | 16.23 | 16.09 | — | 16.31 | 16.17 | 16.22 | — | — |
| — | — | — | — | 16.47 | — | — | — | — | — | — | 16.59 | — | — |
| — | 16.62 | 16.79 | — | — | — | 16.63 | — | — | — | — | — | 16.78 | — |
| — | — | 16.98 | 17.03 | 16.93 | — | 16.92 | 16.86 | 16.88 | 17.02 | 17.01 | — | — | — |
| — | 17.12 | 17.32 | — | 17.22 | — | — | — | — | — | — | — | — | 17.17 |
| 17.48 | 17.51 | — | 17.41 | 17.42 | — | 17.46 | — | 17.34 | 17.36 | — | 17.36 | 17.44 | 17.48 |
| — | — | — | — | — | 17.55 | 17.56 | 17.71 | — | 17.70 | 17.64 | — | — | — |
| — | — | — | — | — | 17.98 | — | — | — | 17.91 | — | — | — | — |
| — | — | 18.07 | — | — | — | — | 18.14 | 18.07 | — | — | — | — | — |
| 18.29 | — | — | — | — | — | — | 18.35 | — | — | — | 18.31 | — | — |
| — | — | — | — | — | 18.48 | — | — | — | — | — | — | 18.40 | — |
| 18.59 | — | — | — | — | — | 18.60 | — | 18.55 | 18.61 | 18.52 | 18.56 | 18.60 | 18.52 |
| 18.84 | — | 18.75 | — | — | — | — | 18.75 | 18.77 | — | — | 18.80 | — | — |
| — | 19.01 | — | 19.02 | 19.02 | — | 18.91 | — | 18.98 | — | — | — | 18.96 | 18.94 |
| — | 19.22 | 19.17 | — | — | 19.11 | — | — | 19.23 | — | — | 19.18 | — | — |

TABLE 17-continued

Compilation of the representative diffraction angles (2Theta) of the X-ray powder diffraction pattern of all vilanterol trifenatate crystalline forms.

Angle 2θ (°)

| Form I | Form II | Form III | Form IV | Form V | Form VI | Form VII | Form VIII | Form IX | Form X | Form XI | Form XII | Form XIII | Form XIV |
|---|---|---|---|---|---|---|---|---|---|---|---|---|---|
| 19.27 | — | — | 19.35 | — | — | 19.28 | — | — | — | 19.36 | — | — | — |
| — | 19.62 | — | 19.45 | 19.56 | — | — | — | 19.40 | — | 19.57 | 19.56 | — | — |
| 19.73 | — | 19.75 | 19.70 | 19.78 | — | — | 19.66 | — | — | — | 19.76 | 19.71 | 19.60 |
| — | — | — | — | — | — | — | — | 19.80 | — | 19.86 | — | — | — |
| — | 20.04 | — | — | — | 20.04 | — | — | 20.04 | — | — | — | 19.94 | — |
| 20.20 | 20.34 | 20.18 | — | 20.33 | — | 20.24 | — | — | — | 20.24 | — | 20.23 | 20.18 |
| 20.55 | — | 20.57 | 20.59 | — | 20.63 | 20.69 | 20.63 | — | 20.50 | 20.53 | — | — | — |
| 20.78 | — | 20.71 | 20.85 | — | — | — | 20.84 | — | 20.80 | — | 20.83 | — | 20.75 |
| — | — | — | — | — | — | — | — | — | — | 20.95 | — | 20.97 | — |
| — | — | — | — | 21.00 | 21.05 | — | — | — | 21.10 | 21.15 | 21.09 | 21.08 | 21.07 |
| 21.34 | 21.15 | 21.26 | 21.17 | 21.35 | — | 21.17 | 21.27 | 21.20 | — | — | — | — | — |
| — | 21.44 | 21.59 | — | — | 21.49 | — | — | 21.42 | 21.49 | — | 21.51 | 21.47 | 21.50 |
| — | 21.69 | 21.70 | — | — | — | 21.66 | — | — | — | — | 21.69 | 21.69 | 21.67 |
| 21.80 | 21.93 | — | 21.93 | 21.93 | — | — | 21.79 | 21.77 | 21.81 | 21.71 | — | — | — |
| — | — | — | — | — | 22.07 | — | 22.07 | — | — | 22.06 | 22.00 | 22.09 | 22.00 |
| — | 22.42 | — | 22.47 | — | 22.44 | — | 22.31 | — | 22.40 | 22.42 | 22.26 | 22.30 | — |
| — | — | 22.60 | — | 22.53 | — | — | — | 22.61 | — | — | — | — | 22.48 |
| 22.68 | — | 22.69 | — | — | — | 22.76 | 22.81 | — | 22.83 | 22.76 | 22.92 | — | — |
| — | 23.01 | 23.07 | 23.04 | 23.02 | 23.01 | — | — | — | — | — | — | 22.99 | 23.03 |
| 23.09 | — | — | — | 23.17 | — | — | — | — | — | — | — | — | — |
| — | 23.39 | — | — | 23.37 | — | — | 23.28 | 23.31 | — | 23.28 | 23.27 | 23.37 | — |
| — | — | — | 23.49 | 23.53 | 23.61 | 23.64 | 23.67 | — | — | — | — | — | 23.44 |
| — | 23.98 | — | — | 23.75 | — | — | 23.91 | 23.97 | 23.83 | — | 23.81 | — | 23.76 |
| 24.09 | — | 24.17 | 24.08 | — | — | — | 24.09 | — | — | — | — | — | — |
| — | — | — | — | — | 24.23 | — | — | 24.19 | — | — | 24.18 | 24.14 | — |
| — | 24.32 | — | 24.31 | 24.34 | — | — | — | 24.37 | 24.38 | 24.36 | — | — | 24.36 |
| — | 25.47 | — | — | — | — | 24.65 | — | — | — | — | 24.52 | 24.53 | — |
| 24.71 | — | 24.70 | 24.86 | 24.82 | 24.71 | — | — | 24.78 | — | — | 24.68 | 24.69 | 24.74 |
| — | — | — | — | — | — | — | 24.90 | — | — | 24.85 | — | — | — |
| 25.11 | — | — | — | — | — | — | — | — | 25.07 | — | — | — | — |
| — | — | 25.28 | 25.33 | — | — | — | 25.28 | — | — | 25.22 | 25.19 | 25.22 | 25.24 |
| — | — | 25.55 | — | 25.51 | 25.43 | — | — | — | — | 25.47 | — | 25.47 | — |
| 25.70 | 25.75 | — | — | — | — | 25.67 | 25.64 | 25.73 | — | — | — | — | 25.60 |
| — | — | — | 25.97 | 25.94 | — | — | 25.93 | — | — | — | 25.90 | 25.81 | — |
| — | — | — | — | — | 26.08 | 26.06 | — | — | 26.06 | — | — | — | — |
| — | 26.14 | 26.15 | — | — | — | — | — | — | — | 26.24 | — | — | 26.23 |
| — | — | — | — | 26.41 | — | — | — | — | — | — | 26.32 | 26.37 | — |
| 26.55 | — | — | 26.50 | — | — | — | — | — | — | — | — | — | 26.50 |
| — | 26.72 | — | 26.74 | 26.62 | — | 26.73 | — | — | — | 26.70 | — | — | — |
| — | — | 26.82 | — | 26.95 | 26.91 | — | 26.95 | — | 26.80 | — | — | — | — |
| — | — | — | 27.02 | — | — | — | — | — | — | — | 27.08 | — | 27.00 |
| 27.22 | 27.18 | — | — | — | — | 27.18 | — | — | — | — | — | 27.20 | — |
| — | — | 27.26 | 27.28 | — | — | — | — | 27.25 | — | 27.29 | — | — | — |
| — | — | — | — | 27.39 | — | — | — | — | — | — | — | — | — |
| 27.56 | — | — | — | — | 27.61 | — | — | — | — | — | 27.50 | 27.58 | — |
| — | 27.69 | — | — | — | — | — | 27.73 | — | 27.81 | — | — | — | — |
| — | — | 27.95 | — | — | — | — | — | — | — | — | 27.99 | — | — |
| — | — | — | 28.06 | — | — | — | — | — | — | — | — | 28.04 | — |
| — | — | — | — | 28.23 | — | — | — | — | — | 28.21 | — | — | 28.23 |
| 28.45 | — | — | 28.42 | — | — | — | 28.43 | — | — | — | — | 28.44 | — |
| — | 28.78 | 28.72 | 28.70 | 28.67 | 28.79 | — | 28.79 | 28.76 | — | 28.80 | 28.67 | — | 28.91 |
| 28.95 | — | — | — | — | 28.96 | — | — | — | 29.06 | — | 28.90 | — | — |
| — | — | — | — | — | 29.13 | — | — | — | — | — | — | — | — |
| — | — | — | — | — | — | — | 29.27 | — | — | — | 29.23 | 29.17 | 29.21 |
| — | — | — | 29.33 | 29.30 | — | — | — | 29.29 | — | 29.31 | 29.37 | 29.38 | — |
| — | 29.61 | 29.49 | — | — | — | 29.54 | — | — | — | — | — | — | — |
| — | 29.70 | — | — | — | — | — | 29.76 | 29.74 | — | 29.76 | — | 29.79 | — |
| — | — | 29.95 | — | — | — | — | — | — | — | — | — | 29.83 | — |
| — | — | — | — | — | — | — | — | — | — | 30.04 | — | — | 30.09 |
| — | — | — | — | — | — | 30.19 | — | — | — | — | 30.17 | — | — |
| 30.38 | — | — | 30.32 | 30.25 | — | — | — | — | — | — | — | 30.29 | — |
| — | — | — | — | — | — | — | 30.43 | — | 30.47 | 30.42 | — | — | — |
| — | — | 30.62 | — | 30.68 | — | — | — | — | — | — | — | — | — |
| 31.00 | 30.84 | — | 30.82 | — | — | — | 30.85 | — | — | — | — | — | 30.94 |
| 31.00 | — | 31.00 | — | — | — | — | 31.06 | — | 31.04 | — | — | — | — |
| — | — | — | 31.24 | — | — | — | — | — | — | — | 31.23 | — | — |
| — | — | — | — | 31.46 | 31.51 | — | 31.55 | — | — | 31.47 | 31.54 | 31.38 | 31.48 |
| 31.63 | 31.61 | 31.68 | — | — | — | — | — | — | — | — | — | 31.73 | — |
| — | — | — | 31.83 | 31.83 | — | — | — | — | — | 31.99 | 31.83 | — | 31.97 |
| — | 32.07 | — | — | — | — | — | — | — | — | — | — | — | — |
| — | — | 32.15 | 32.17 | 32.13 | — | — | 32.20 | — | — | — | — | 32.17 | — |
| 32.40 | 32.39 | — | — | — | 32.30 | — | — | — | — | — | 32.43 | — | — |
| 33.54 | — | 32.65 | — | — | — | — | — | — | — | — | — | — | — |

TABLE 17-continued

Compilation of the representative diffraction angles (2Theta) of the X-ray powder diffraction pattern of all vilanterol trifenatate crystalline forms.

Angle 2θ (°)

| Form I | Form II | Form III | Form IV | Form V | Form VI | Form VII | Form VIII | Form IX | Form X | Form XI | Form XII | Form XIII | Form XIV |
|---|---|---|---|---|---|---|---|---|---|---|---|---|---|
| — | — | — | — | 32.83 | — | — | — | 32.89 | 32.87 | — | — | — | — |
| — | — | 33.11 | 33.13 | — | — | — | 33.22 | — | — | 33.06 | 33.12 | — | — |
| — | — | — | — | — | — | — | — | 33.41 | 33.53 | — | — | — | — |
| — | — | — | 33.67 | — | — | — | — | — | — | — | 33.64 | — | 33.60 |
| — | — | 33.78 | — | 33.83 | — | — | 33.87 | — | — | — | — | — | — |
| — | 33.91 | — | — | — | — | — | — | — | — | — | — | — | 33.99 |
| — | — | — | — | 34.17 | — | — | 34.15 | — | — | — | — | 34.16 | — |
| 34.34 | — | — | 34.24 | — | — | — | — | — | — | — | — | — | — |
| — | 34.46 | — | — | — | — | — | — | 34.46 | 34.50 | 34.56 | — | — | 34.55 |
| — | — | 34.63 | 34.66 | 34.60 | — | — | 34.60 | — | — | — | — | — | — |
| — | — | — | — | — | — | — | 34.81 | — | — | — | — | 34.82 | — |
| — | 34.98 | — | — | 34.99 | — | — | — | — | — | — | — | — | 34.96 |
| — | — | — | — | — | — | — | — | — | — | — | — | 35.12 | — |
| 35.19 | — | 35.16 | — | — | — | — | — | — | — | 35.22 | 35.21 | — | — |
| — | — | — | — | — | — | — | — | — | 35.29 | — | — | — | — |
| 35.49 | 35.41 | — | 35.40 | — | 35.43 | — | 35.41 | — | — | — | — | — | — |
| — | — | — | — | — | — | 35.61 | — | — | — | — | 35.59 | — | 35.54 |
| — | — | — | — | — | — | — | — | 35.89 | — | — | — | — | 35.88 |
| — | — | — | — | 36.04 | — | — | — | — | — | — | — | — | — |
| 36.19 | — | — | — | — | — | — | — | — | — | 36.23 | — | 36.19 | — |
| — | — | 36.37 | — | — | — | 36.39 | — | — | — | — | — | — | — |
| 36.52 | 36.45 | — | — | — | — | — | — | — | 36.55 | — | — | — | — |
| — | — | — | 36.62 | 36.72 | — | 36.79 | — | 36.69 | — | — | — | — | — |
| 36.85 | — | — | — | — | — | — | — | — | — | — | 36.90 | 36.86 | — |
| — | 37.11 | — | — | — | — | — | — | — | 37.02 | — | — | — | — |
| — | — | — | 37.23 | — | — | — | 37.31 | — | — | — | 37.25 | 37.28 | — |
| — | — | 37.42 | — | — | 37.40 | — | — | 37.41 | — | — | — | — | 37.41 |
| — | — | — | — | 37.66 | — | — | 37.76 | — | — | 37.65 | — | 37.69 | — |
| 38.11 | — | 38.11 | — | 38.14 | — | — | — | — | — | — | — | — | — |
| — | — | — | 38.28 | — | — | — | — | — | — | — | — | — | — |
| — | 38.35 | — | — | — | — | — | — | — | — | — | — | — | — |
| 38.56 | — | — | 38.68 | 38.67 | — | — | — | 38.53 | 38.66 | — | 38.58 | — | 38.54 |
| — | — | — | 38.81 | — | — | — | 38.71 | — | — | — | — | — | — |
| 39.17 | 39.29 | — | — | — | — | — | — | 39.12 | 39.28 | — | — | — | — |
| — | — | — | 39.36 | — | — | — | — | — | — | — | — | — | — |
| — | — | — | — | 39.48 | — | 39.46 | — | — | — | 39.48 | 39.59 | — | 39.42 |
| 39.63 | — | — | — | — | — | — | 39.65 | — | — | — | — | 38.67 | — |

Any one or combination of the polymorphs of the present invention can be in solvated (such as hydrated) or non-solvated (such as non-hydrated) form. Therefore the present invention further provides one or more of:

a solvate of a polymorph as defined herein;

a hydrate of a polymorph as defined herein;

a non-solvate of a polymorph as defined herein; and/or a non-hydrate of a polymorph as defined herein.

The present invention further provides a crystal form of vilanterol trifenatate preparable by providing vilanterol trifenatate form I and cystallising from a mixture of acetone and water in a ratio in the range of from about 30:6-3 by volume (i.e. from about 10:2-1 or from about 5:1 to 10:1 by volume) and optionally converting the form II and/or III thus prepared to another form of vilanterol trifenatate by crystallising from a solvent or solvent system selected from: heptane, cyclohexane, methylcyclohexane, 2-propanol, 3-methyl-1-butanol, anisole, nitromethane, cyclohexane/ethanol (50:50), cyclohexane/2-methyltetrahydrofuran (50:50), heptane/dimethoxyethane (DME) (50:50), cyclohexane:methylketone (50:50) and methyl cyclohexane.

Preferably, the crystal form of vilanterol trifenatate is preparable by providing vilanterol trifenatate form I and cystallising from a mixture of acetone and water in a ratio in the range of from about 30:3 by volume (i.e. from about 10:1 by volume) and optionally converting the form II thus prepared to another form of vilanterol trifenatate as described above or by adding further water for conversion to form III.

BRIEF DESCRIPTION OF THE DRAWINGS

Specific examples of polymorphs of the present invention, in particular, novel forms II to XIV, processes for preparing them and some of their characteristics or properties will now be described, with reference to the accompanying drawings, in which.

2Theta, 2-theta and 2θ are used synonymously through this specification.

DETAILED DESCRIPTION OF THE INVENTION

Vilanterol Trifenatate Form II

Accordingly, the present invention provides a new crystalline form of vilanterol trifenatate, designated as form II, characterized by an X-ray powder diffraction pattern having the following characteristic diffraction angles (2Theta): 14.26°; 14.72°; 17.51°; 23.98° and 24.32°.

Further Structural Characterization of Form II

Figure 1:
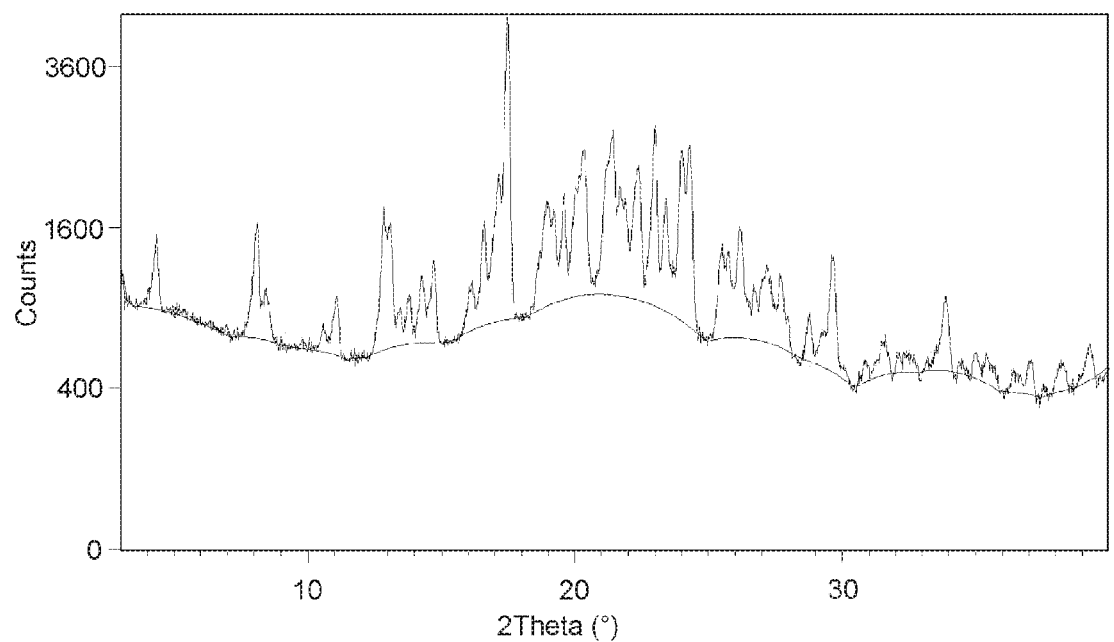
FIG. 1: XRPD diffractogram of new crystalline form II of vilaterol trifenatate.

Preferably, crystalline form II of vilanterol trifenatate has an X-ray powder diffraction pattern as depicted in FIG. 1 and shows the diffraction angles (2Theta) presented in table 1.

TABLE 1

X-ray powder diffraction peak list of vilanterol trifenatate crystalline form II.

| Angle 2θ (°) | Height [cts] | d value (Å) | Intensity (%) |
|---|---|---|---|
| *4.31 | 641 | 20.49 | 20 |
| *8.14 | 892 | 10.86 | 27 |
| *8.43 | 375 | 10.49 | 11 |
| 10.59 | 164 | 8.35 | 5 |
| 11.09 | 410 | 7.98 | 13 |

TABLE 1-continued

X-ray powder diffraction peak list of vilanterol trifenatate crystalline form II.

| Angle 2θ (°) | Height [cts] | d value (Å) | Intensity (%) |
|---|---|---|---|
| *12.85 | 1203 | 6.89 | 37 |
| 13.10 | 943 | 6.76 | 29 |
| 13.48 | 243 | 6.57 | 7 |
| 13.81 | 301 | 6.41 | 9 |
| 14.26 | 480 | 6.21 | 15 |
| 14.72 | 576 | 6.02 | 18 |
| 16.09 | 317 | 5.51 | 10 |
| *16.62 | 893 | 5.33 | 27 |
| *17.12 | 1319 | 5.18 | 40 |
| 17.51 | 3281 | 5.07 | 100 |
| 19.01 | 915 | 4.67 | 28 |
| 19.22 | 816 | 4.62 | 25 |
| 19.62 | 937 | 4.52 | 29 |
| 20.04 | 1048 | 4.43 | 32 |
| 20.34 | 1483 | 4.37 | 45 |
| 21.15 | 1184 | 4.20 | 36 |
| 21.44 | 1693 | 4.14 | 52 |
| 21.69 | 1033 | 4.10 | 31 |
| 21.93 | 851 | 4.05 | 26 |
| 22.42 | 1232 | 3.97 | 38 |
| 23.01 | 1868 | 3.87 | 57 |
| 23.39 | 1026 | 3.80 | 31 |
| 23.98 | 1660 | 3.71 | 51 |
| 24.32 | 1724 | 3.66 | 53 |
| 25.47 | 675 | 3.50 | 21 |
| 25.75 | 668 | 3.46 | 20 |
| 26.14 | 906 | 3.41 | 28 |
| 26.72 | 375 | 3.34 | 11 |
| *27.18 | 580 | 3.28 | 18 |
| *27.69 | 548 | 3.22 | 17 |
| 28.78 | 327 | 3.10 | 10 |
| 29.61 | 813 | 3.01 | 25 |
| 29.70 | 800 | 3.01 | 24 |
| 30.84 | 105 | 2.90 | 3 |
| 31.61 | 204 | 2.83 | 6 |
| 32.07 | 98 | 2.79 | 3 |
| 32.39 | 95 | 2.76 | 3 |
| 33.91 | 480 | 2.64 | 15 |
| 34.46 | 57 | 2.60 | 2 |
| 34.98 | 132 | 2.57 | 4 |
| 35.41 | 171 | 2.53 | 5 |
| 36.45 | 89 | 2.47 | 3 |
| 37.11 | 175 | 2.42 | 5 |
| 38.35 | 116 | 2.35 | 4 |
| 39.29 | 194 | 2.29 | 6 |

Figure 2:
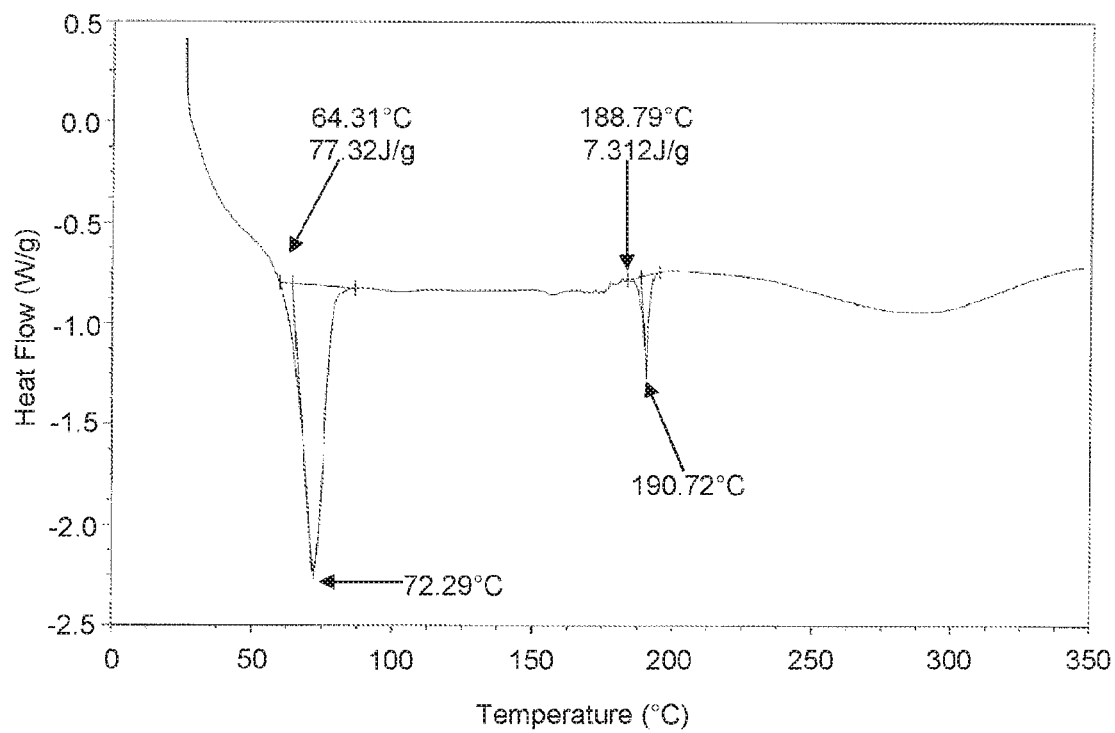
FIG. 2: DSC profile of new crystalline form II of vilaterol trifenatate.

New crystalline form II of vilanterol trifenatate may be further characterized by differential scanning calorimetry (DSC) profile as depicted in FIG. 2 having an endothermic event with onset at 64° C. and a peak at about 72° C., and a degradation event with onset at 189° C. and a peak at 191° C.

Figure 3:
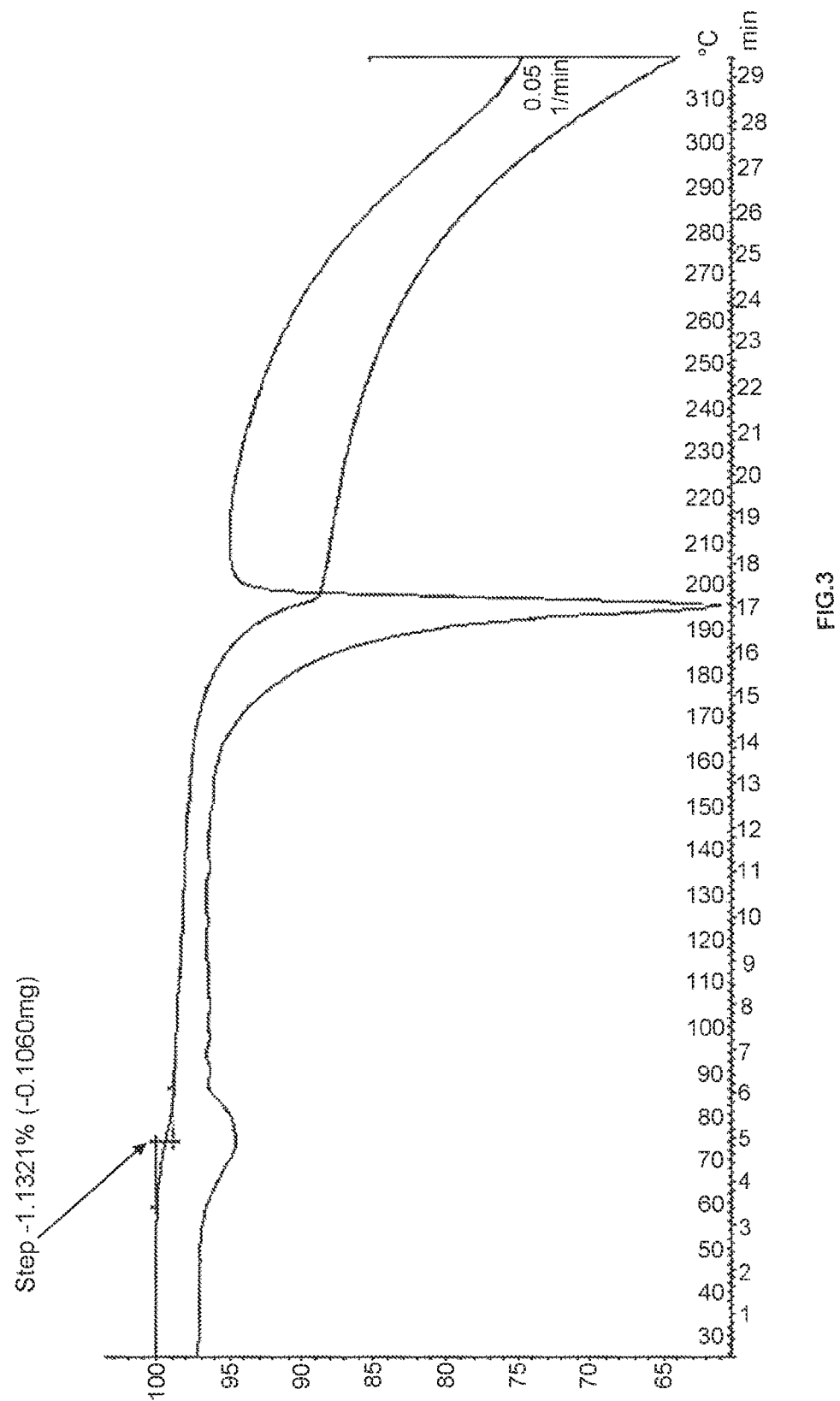
FIG. 3: TGA profile of new crystalline form II of vilaterol trifenatate.

New crystalline form II of vilanterol trifenatate may be further characterized by thermogravimetric analysis (TGA) profile as depicted in FIG. 3 having a weight loss of approx. 1.13% in agreement with the water evolution from evolved gas analysis.

The proportion molar proportion of vilanterol trifenatate: water is 1:0.57 (confined by EGA). The TGA graph shows that water release starts at about 75° C., which indicates that the water is not bonded to the vilanterol trifenatate but is on the surface of the crystals. If the water were bonded, it would be released at temperatures higher than 100° C., typical behaviour of a hydrate. Accordingly, the polymorph of the present invention is non-hydrated.

Figure 4:
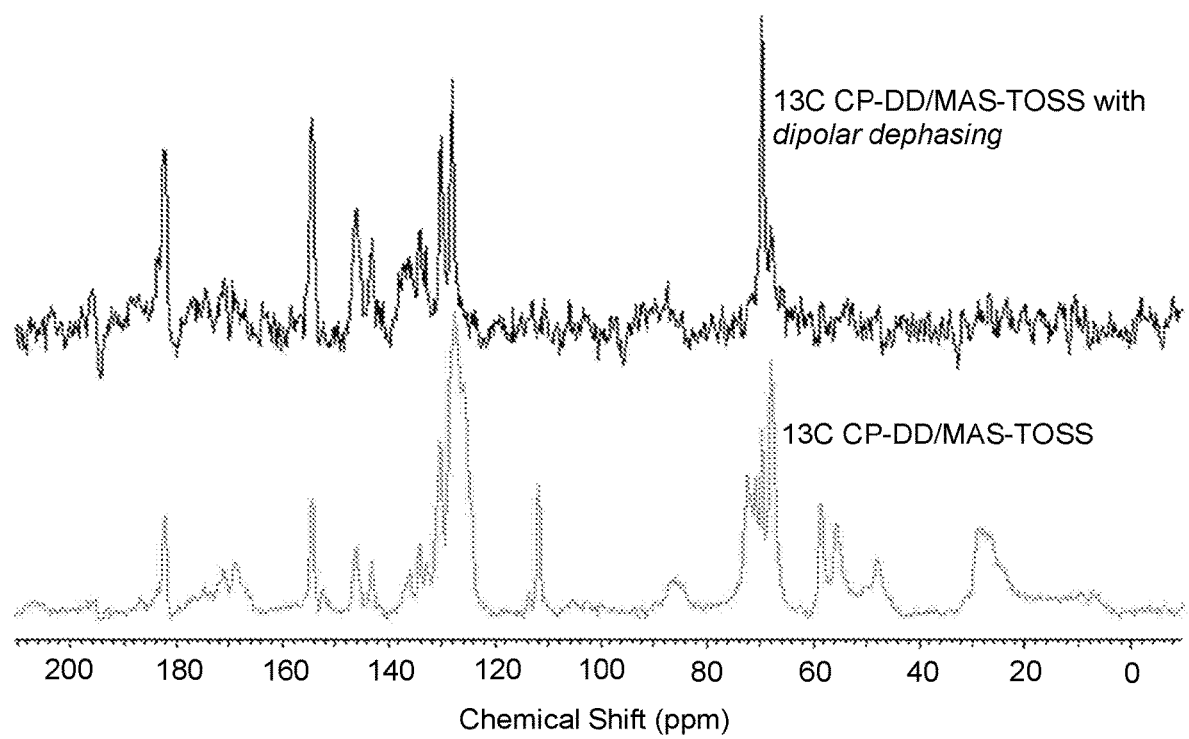
FIG. 4: 13C CP-DD/MAS-TOSS and 13C CP-DD/MAS-TOSS with Dipolar Dephasing spectrum of new crystalline form II of vilaterol trifenatate.

New crystalline form II of vilanterol trifenatate may be further characterized by $^{13}C$ CP-DD/MAS-TOSS and $^{13}C$ CP-DD/MAS-TOSS with Dipolar Dephasing spectra as depicted in FIG. 4 and shows the characteristic chemical shifts in ppm units (±0.218 ppm): 182.35, 171.24, 169.06, 154.47, 152.51, 146.19, 143.36, 136.17, 134.43, 133.12, 130.50, 127.67, 126.15, 124.62.

Figure 5:
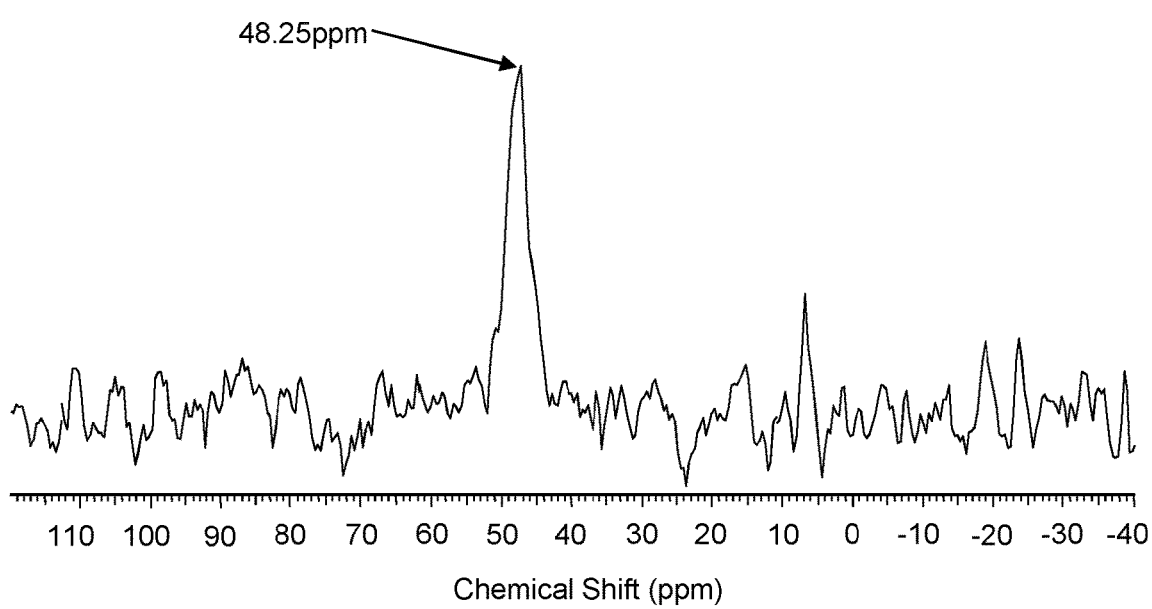
FIG. 5: 15N CP-DD/MAS spectrum of new crystalline form II of vilaterol trifenatate.

New crystalline form II of vilanterol trifenatate may be further characterized by $^{15}$N CP-DD/MAS spectrum as depicted in FIG. 5.

Hygroscopicity of Form II

New crystalline form II of vilanterol trifenatate may be further characterized by dynamic vapor sorption analysis having a mass increase of 0.04% at 80% RH and 25° C. as shown in Table 2 and Example 9 hereinbelow. The values in the table (and comparable tables in this specification) are weight % variations that result from the use of the European Pharmacopoeia equation provided in the general experimental section further below. Weights of the sample at differing % RHs are not shown in this table. The hygroscopicity value is directly obtained from the sorption row at 80% RH, cycle 1.

TABLE 2

Dynamic vapor sorption analysis of vilanterol trifenatate crystalline form II.

| | | Change In Mass (%) | | |
|---|---|---|---|---|
| | Target RH (%) | Sorption | Desorption | Hysteresis |
| Cycle 1 | 0.0 | — | −0.03351 | — |
| | 10.0 | — | −0.01706 | — |
| | 20.0 | — | −0.00684 | — |
| | 30.0 | — | 0.00031 | — |
| | 40.0 | −0.00015 | 0.00692 | 0.00707 |
| | 50.0 | 0.00607 | 0.01476 | 0.00868 |
| | 60.0 | 0.01353 | 0.02244 | 0.00892 |
| | 70.0 | 0.02160 | 0.03051 | 0.00892 |
| | 80.0 | 0.03750 | 0.04181 | 0.00430 |
| | 90.0 | 0.05802 | 0.05802 | — |
| Cycle 2 | 0.0 | −0.03351 | — | — |
| | 10.0 | −0.02290 | — | — |
| | 20.0 | −0.01545 | — | — |
| | 30.0 | −0.00907 | — | — |
| | 40.0 | −0.00261 | — | — |
| | 50.0 | 0.00277 | — | — |
| | 60.0 | 0.01068 | — | — |
| | 70.0 | 0.01821 | — | — |
| | 80.0 | 0.03189 | — | — |
| | 90.0 | 0.04819 | — | — |

The data in table 2 show that form II of vilanterol trifenatate is even less hygroscopic than form I in comparative testing (0.04% mass increase versus 0.19% mass increase for form I, as indicated in Example 9 hereinbelow) and therefore may be further characterized according to the European Pharmacopoeia (EP, version 7.0) as non-hygroscopic. This characteristic presents an advantage over other crystalline forms with respect to handling and stability.

Hygroscopicity describes water uptake by a compound under differing considions of relative humidity. The more hygroscopic the compound, the higher the difference in the water content at different relative humidities. Active pharmaceutical ingredients (APIs) that change water content during formulation processes and in the final formulation need to be handled with more care with regard to environmental control during production and packaging. Accordingly, a low level of hygroscopicity is advantageous and approximately zero hygroscopicity—defined as an increase in mass of less than 0.2%—(non-hygroscopic) is particularly preferred.

Most materials do not release water at the same rate as they absorb water, and the difference in water uptake between the sorption and desorption isotherms is termed 'hysteresis' of the material. Very similar sorption and desorption curves means little to no hysteresis, indicating that the material absorbed water onto the surface in the increasing humidity run and then the water simply desorbed from the surface at a similar rate in the decreasing humidity part of the experiment. Where the sorption and desorption curves are different, this indicates that the material absorbed water into the structure.

Accordingly, the present invention further provides a novel polymorphic form of vilanterol trifenatate having a a mass increase of less than 0.1%, preferably less than 0.75%, more preferably less than 0.5%, at 80% RH and 25° C. as determined by DVS analysis (as described herein—see Example 9 and FIG. 29 together with the General Experimental section hereinbelow).

Structural Stability of Form II

Figure 6:
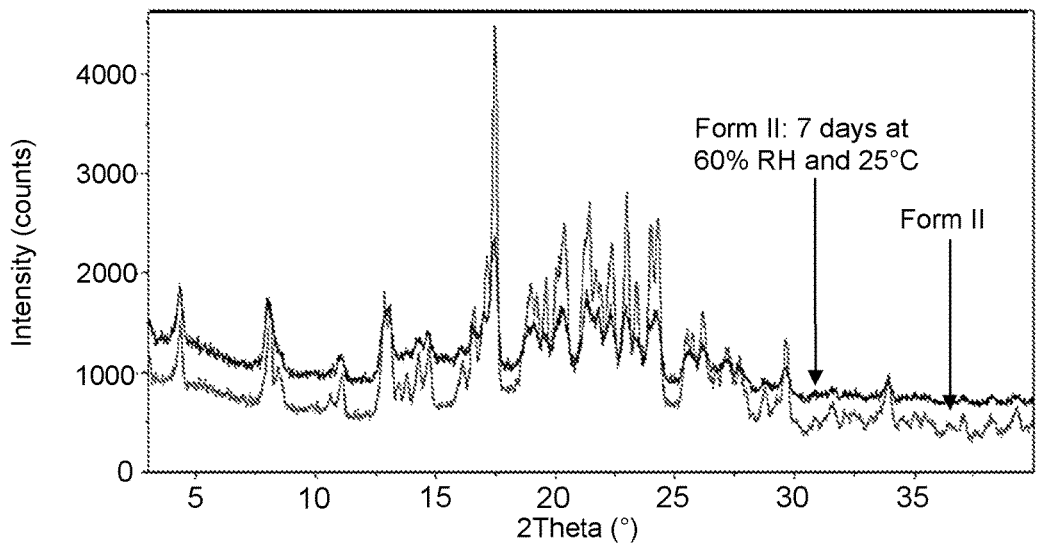
FIG. 6: XRPD diffractogram of new crystalline form II of vilaterol trifenatate under 60% RH and 25° C. for 7 days.
Figure 10:
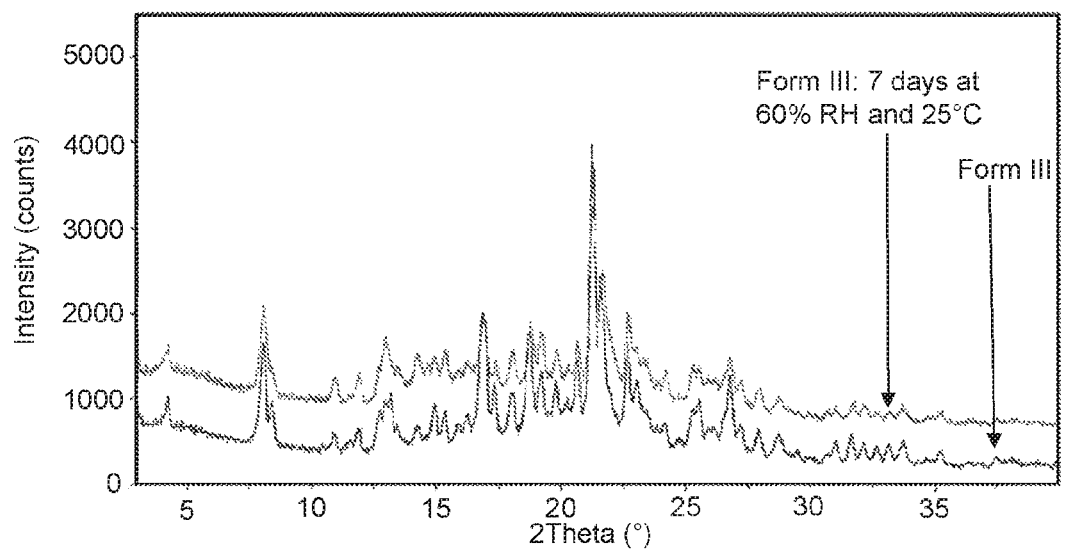
FIG. 10: XRPD diffractogram of new crystalline form III of vilaterol trifenatate under 60% RH and 25° C. for 7 days.

New crystalline form II of vilanterol trifenatate may be further characterized by its stability at 60% RH and 25° C. for 7 days, as described in FIG. 10 hereinbelow. New crystalline form II of vilanterol trifenatate provides no significant modifications in XRPD pattern when exposed to 60% RH and 25° C. for 7 days, indicating an excellent stability as depicted in FIG. 6.

Preparation of Form II

The present invention further provides a method for preparing form II of vilanterol trifenatate, which method comprises providing a solution of vilanterol trifenatate form I in acetone, adding water, preferably in a ratio of acetone 30 vol. to water less than 6 vol., more preferably less than 5 vol., especially preferably less than 4 vol., such as 3 vol. to the solution, and isolating the resulting product (form II).

Preferably, the process comprises:

a1) suspending vilanterol trifenatate form I in acetone, more preferably in about 30 vol., a2) heating the suspension, preferably up to 50° C., more preferably with stirring, a3) adding water, more preferably 3 vol. to the clear solution, yet more preferably with stirring, a4) cooling down the obtained solution, preferably to 5-0° C., more preferably at a rate about 10° C./hour a5) optionally, adding a seed of crystalline form II, and a6) isolating new crystalline form II, preferably by filtration, more preferably under reduced pressure, followed by drying or optionally by spray drying the resulting suspension.

Unexpectedly, it was observed that the use of water combined with acetone has a highly significant effect on the molecular rearrangement of vilanterol trifenatate inducing the formation of new crystalline forms, in particular forms II and III (form III is further described below).

Furthermore, the inventors have additionally found that the removal of water from the process of the present invention results in the formation of the previously described crystalline form I of vilanterol trifenatate.

High Purity Form II

The present invention still further provides an improved process to prepare vilaterol trifenatate in high purity. The purity of the product obtained by following the procedure described above presents a better purity profile than the procedures described in literature.

The present inventors also carried out recrystallizations using the solvent systems reported for the salt formation with triphenyl acetic acid according to the processes of WO2003/024439 (GSK) and WO2014/041565 (Laurus), and an impurity (referred to as impurity A, defined below) at high levels at 1.33 RRT by HPLC (using the protocol described hereinbelow) was observed.

The inventors have identified the influence of the recrystallization solvent system on the final purity of vilanterol trifenatate, where the solvent system used in the process plays an important role in maintaining the impurities below suitable limits. Recrystallizations carried out using acetone/water solvent systems, for example compared to using acetone alone, gave final products with higher chemical purity.

It has surprisingly been found that impurity A, present in the non-purified (prior art) vilanterol trifenatate at a level of 0.17% by area by HPLC, is reduced to 0.06% by area as determined by HPLC when following the process of the present invention, in particular when preparing form II according to the invention. This improvement in the final product purity is of extreme importance, allowing supply high quality medicines to patients.

The structure for the impurity A is presented below:

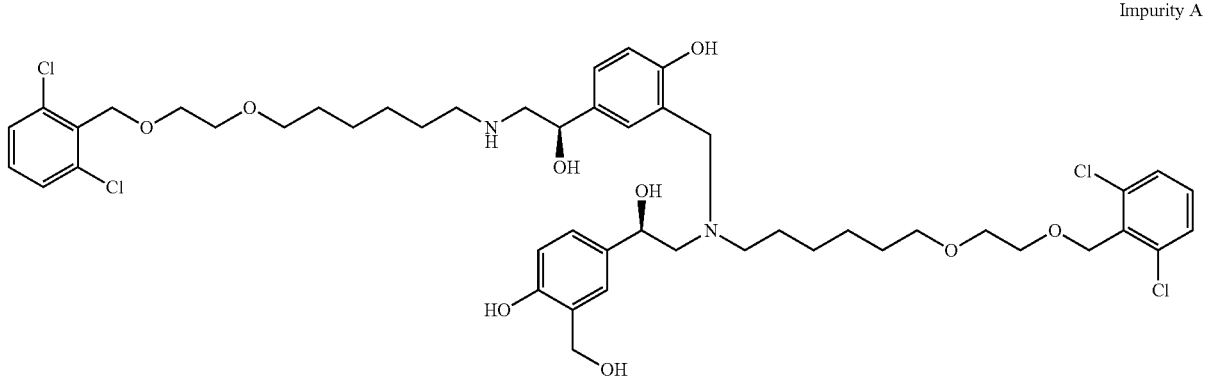 [SMILES: OCc1cc([C@@H](O)CN(CCCCCCOCCOCc2c(Cl)cccc2Cl)Cc2cc([C@@H](O)CNCCCCCCOCCOCc3c(Cl)cccc3Cl)ccc2O)ccc1O]

Impurity A

Therefore, vilanterol trifenatate obtained from the above process contains less than 0.15%, preferably less than 0.10%, of any impurity by area as determined by reverse phase HPLC.

Accordingly, the present invention further provides high purity vilanterol trifenatate, optionally a novel polymorphic form thereof, comprising less than 0.15%, preferably less than 0.1%, more preferably less than 0.075%, (such as 0.05-0.06%) of Impurity A by HPLC (as described herein).

Preferably, the high purity vilanterol trifenatate is form II or form III as defined herein.

Vilanterol Trifenatate Form III

The present invention therefore further provides a new crystalline form of vilanterol trifenatate, designated form III, characterized by an X-ray powder diffraction pattern having the following characteristic diffraction angles (2Theta): 11.89°; 15.36°; 18.07°; 21.26° and 21.59°.

Figure 7:
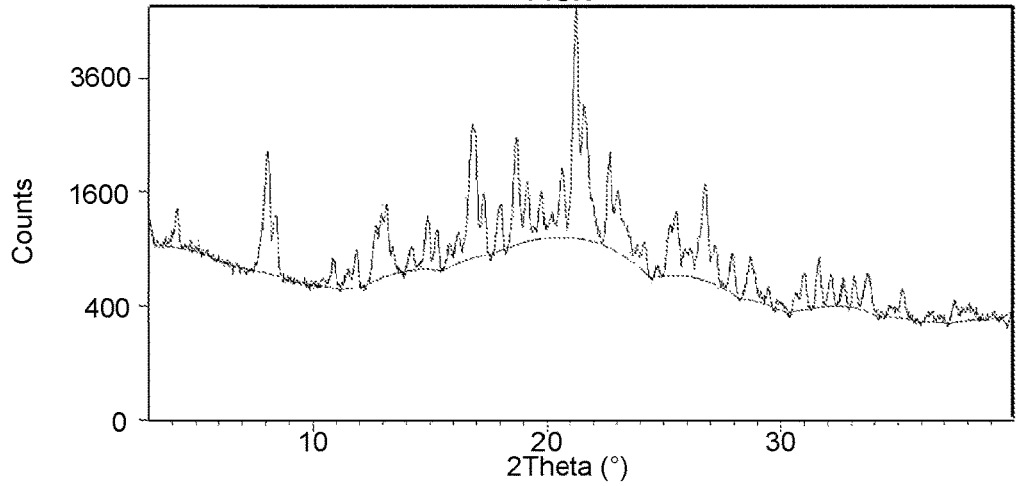
FIG. 7: XRPD diffractogram of new crystalline form III of vilaterol trifenatate.

New crystalline form III of vilanterol trifenatate trifenatate has an X-ray powder diffraction pattern as depicted in FIG. 7 and shows the diffraction angles (2Theta) presented in table 3.

TABLE 3

X-ray powder diffraction peak list of vilanterol trifenatate crystalline form III.

| Angle 2θ (°) | Height [cts] | d value (Å) | Intensity (%) |
|---|---|---|---|
| 4.22 | 444 | 20.92 | 10 |
| 8.12 | 1383 | 10.89 | 32 |
| 8.44 | 648 | 10.48 | 15 |
| 10.91 | 258 | 8.11 | 6 |
| 11.52 | 156 | 7.68 | 4 |
| 11.89 | 333 | 7.44 | 8 |
| 12.69 | 532 | 6.98 | 12 |
| 12.92 | 649 | 6.85 | 15 |
| 13.16 | 792 | 6.73 | 19 |
| 13.44 | 241 | 6.59 | 6 |
| 14.24 | 226 | 6.22 | 5 |
| 14.99 | 437 | 5.91 | 10 |
| 15.36 | 419 | 5.77 | 10 |
| 15.86 | 219 | 5.59 | 5 |
| 16.25 | 325 | 5.46 | 8 |
| 16.79 | 1775 | 5.28 | 42 |
| 16.98 | 1525 | 5.22 | 36 |
| 17.32 | 731 | 5.12 | 17 |
| 18.07 | 525 | 4.91 | 12 |
| 18.75 | 1469 | 4.73 | 34 |
| 19.17 | 748 | 4.63 | 18 |
| 19.75 | 576 | 4.49 | 14 |
| 20.18 | 246 | 4.40 | 6 |
| 20.57 | 800 | 4.32 | 19 |
| 20.71 | 634 | 4.29 | 15 |
| 21.26 | 4263 | 4.18 | 100 |
| 21.59 | 1968 | 4.12 | 46 |
| 21.70 | 1751 | 4.10 | 41 |
| 22.60 | 925 | 3.93 | 22 |
| 22.69 | 1319 | 3.92 | 31 |
| 23.07 | 739 | 3.86 | 17 |
| 24.17 | 299 | 3.68 | 7 |
| 24.70 | 68 | 3.60 | 2 |
| 25.28 | 507 | 3.52 | 12 |
| 25.55 | 705 | 3.49 | 17 |
| 26.15 | 261 | 3.41 | 6 |
| 26.82 | 1056 | 3.32 | 25 |
| 27.26 | 335 | 3.27 | 8 |
| 27.95 | 353 | 3.19 | 8 |
| 28.72 | 372 | 3.11 | 9 |
| 29.49 | 126 | 3.03 | 3 |
| 29.95 | 46 | 2.98 | 1 |
| 30.62 | 112 | 2.92 | 3 |
| 31.00 | 276 | 2.88 | 6 |
| 31.68 | 345 | 2.82 | 8 |
| 32.15 | 262 | 2.78 | 6 |

TABLE 3-continued

X-ray powder diffraction peak list of vilanterol trifenatate crystalline form III.

| Angle 2θ (°) | Height [cts] | d value (Å) | Intensity (%) |
|---|---|---|---|
| 32.65 | 209 | 2.74 | 5 |
| 33.11 | 253 | 2.71 | 6 |
| 33.78 | 266 | 2.65 | 6 |
| 34.63 | 78 | 2.59 | 2 |
| 35.16 | 196 | 2.55 | 5 |
| 36.37 | 54 | 2.47 | 1 |
| 37.42 | 132 | 2.40 | 3 |
| 38.11 | 80 | 2.36 | 2 |

Figure 8:
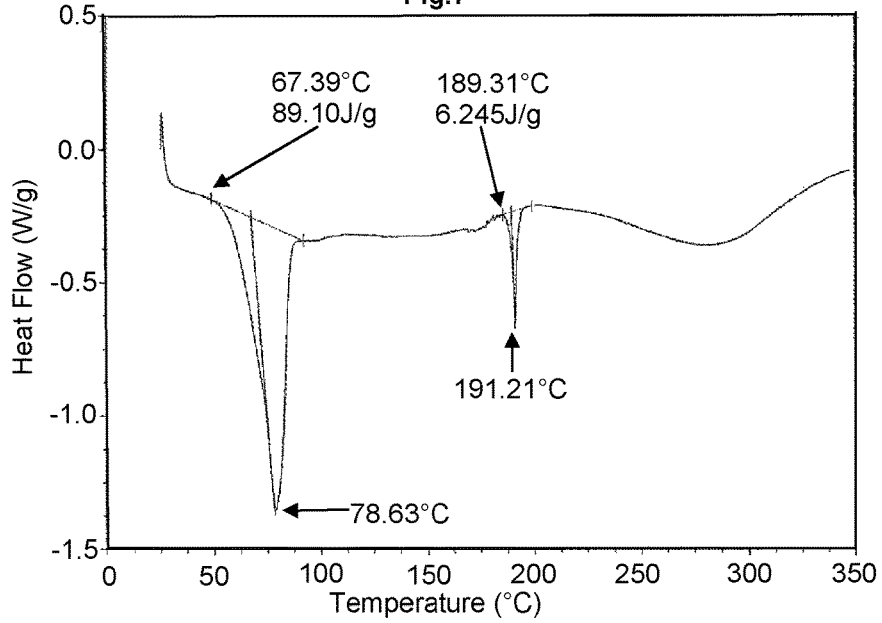
FIG. 8: DSC profile of new crystalline form III of vilaterol trifenatate.

New crystalline form III of vilanterol trifenatate may be further characterized by differential scanning calorimetry profile as depicted in FIG. 8 having an endothermic event with onset at 67° C. and peak at 79° C., and a degradation event with onset at 189° C. and peak at 191° C.

Figure 9:
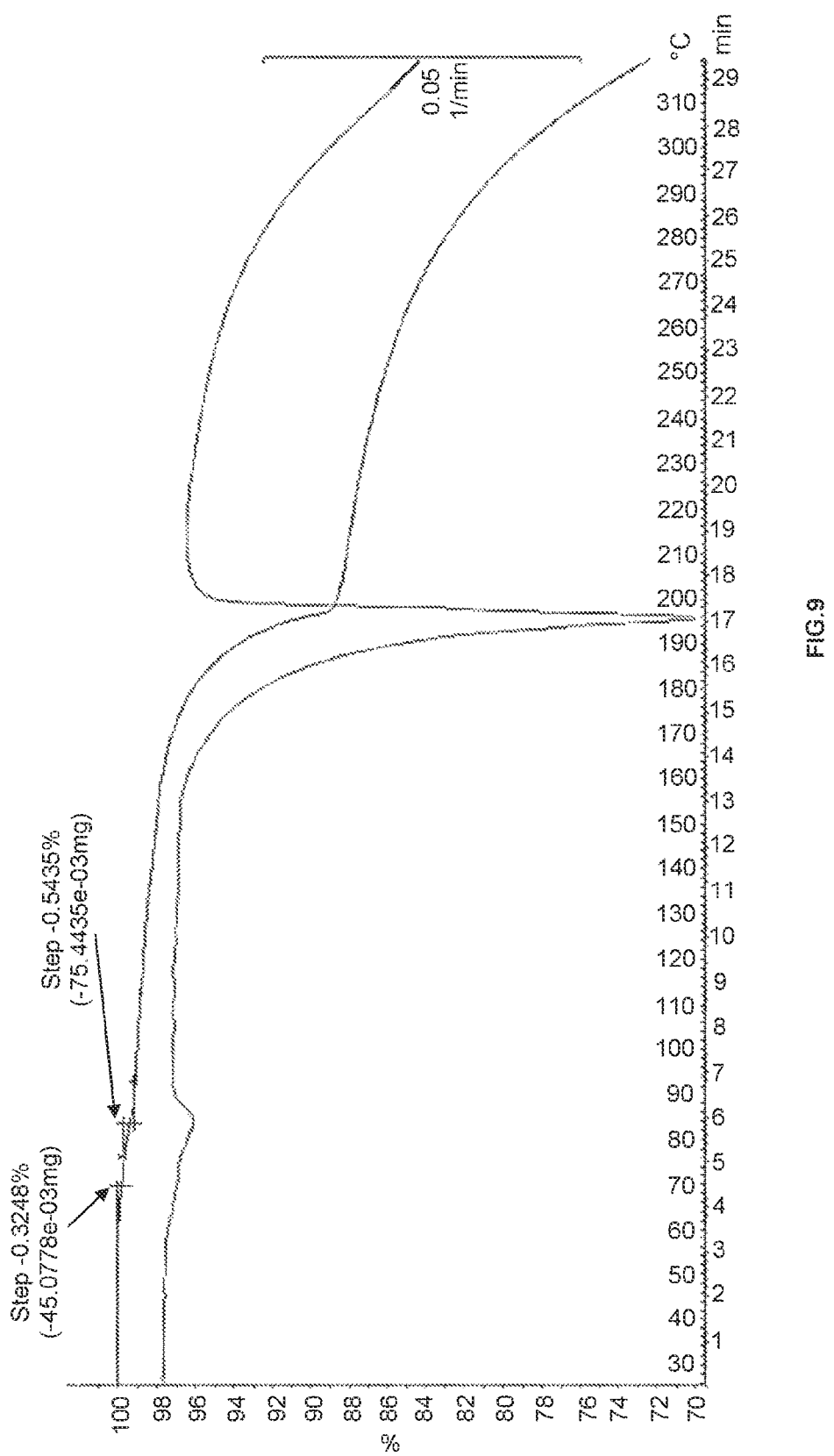
FIG. 9: TGA profile of new crystalline form III of vilaterol trifenatate.

New crystalline form III of vilanterol trifenatate may be further characterized by thermogravimetric analysis profile as depicted in FIG. 9 having two consecutive weight loss events of approx. 0.32% and 0.54% in agreement with the water evolution from evolved gas analysis.

The proportion molar proportion of vilanterol trifenatate: water is 1:0.37 (confimed by EGA). The TGA graph shows that water release starts at about 65° C. which indicates that the water is not bonded to the vilanterol trifenatate, but is on the surface of the crystals. If the water were bonded, it would be released at temperatures higher than 100° C., typical behavior of a hydrate. Accordingly, the polymorph of the present invention is non-hydrated.

Hygroscopicity of Form III

New crystalline form III of vilanterol trifenatate may be further characterized by dynamic vapor sorption analysis having a mass increase of 1.1% at 80% RH and 25° C. as shown in table 4.

TABLE 4

Dynamic vapor sorption analysis of vilanterol trifenatate crystalline form III.

| | Target RH (%) | Change In Mass (%) | | |
|---|---|---|---|---|
| | | Sorption | Desorption | Hysteresis |
| Cycle 1 | 0.0 | — | −0.017 | — |
| | 10.0 | — | 0.002 | — |
| | 20.0 | — | 0.015 | — |
| | 30.0 | — | 0.024 | — |
| | 40.0 | 0.000 | 0.035 | 0.035 |
| | 50.0 | 0.008 | 0.280 | 0.271 |
| | 60.0 | 0.022 | 0.421 | 0.399 |
| | 70.0 | 0.037 | 0.567 | 0.530 |
| | 80.0 | 1.083 | 1.144 | 0.061 |
| | 90.0 | 1.857 | 1.857 | — |
| Cycle 2 | 0.0 | −0.017 | — | — |
| | 10.0 | −0.003 | — | — |
| | 20.0 | 0.008 | — | — |
| | 30.0 | 0.016 | — | — |
| | 40.0 | 0.025 | — | — |
| | 50.0 | 0.033 | — | — |
| | 60.0 | 0.041 | — | — |
| | 70.0 | 0.056 | — | — |
| | 80.0 | 1.111 | — | — |
| | 90.0 | 1.952 | — | — |

New crystalline form III of vilanterol trifenatate may be further characterized as slightly hygroscopic.

Structural Stability of Form III

New crystalline form III of vilanterol trifenatate may be further characterized by the stability at 60% RH and 25° C. for 7 days, as described in Example 10 below. New crystalline form III of vilanterol trifenatate provides no significant modifications in XRPD pattern when exposed to 60% RH and 25° C. for 7 days, indicating an excellent stability as depicted in FIG. 10.

Preparation of Form III

The present invention provides a method for preparing form III of vilanterol trifenatate comprising providing a suspension of form II with form III in water and isolating the form III.

Preferably, the method comprises:
b1) suspending vilanterol trifenatate forms II and III in water, preferably in 5 vol., more preferably at 20-25° C. and preferably stirring,
b2) isolating new crystalline form III, preferably by filtration, preferably under reduced pressure followed by drying or optionally by spray drying the suspension.

Alternatively, particularly if no form III is available, the present invention provides a method for preparing form III of vilanterol trifenatate comprising forming a suspension of form I in acetone, adding water, preferably in a ratio of acetone 30 vols, to water 5 vols or more, such as 6 vols., and isolating new form III.

Preferably, the method comprises:
c1) suspending vilanterol trifenatate form I in acetone, more preferably in 30 vol.,
c2) heating the suspension, preferably up to 50° C.,
c3) adding water, more preferably 6 vol., to the obtained solution,
c4) cooling down the obtained solution, preferably to 5-0° C., more preferably at a rate about 10° C./hour and,
c5) optionally, adding a seed of crystalline form III, and
c6) isolating new crystalline form III, preferably by filtration preferably under reduced pressure, followed by drying or optionally by spray drying the suspension.

Unexpectedly, it was observed that the amount of water combined with acetone has an effect on the molecular rearrangement of vilanterol trifenatate leading to the formation of new crystalline forms.

High Purity Form III

The Impurity A (described above in relation to form II) that is present in the non-purified vilanterol trifenatate form I (0.17% in area by HPLC) is reduced to 0.05% in area by HPLC by following the procedure for the preparation of form III, such as described in Example 3 or Example 4 hereinbelow.

Accordingly, the present invention further provides a novel polymorphic form of vilanterol trifenatate comprising less than 0.15%, preferably less than 0.1%, more preferably less than 0.075%, (such as 0.05-0.06%) of Impurity A by HPLC (as described herein).

The present invention further provides an alternative method for preparing form III of vilanterol trifenatate comprising:
d1) suspending vilanterol trifenatate form II in heptane, preferably in 24 vol.,
d2) heating the suspension preferably up to 50° C., preferably at a rate about 20° C./hour and preferably stir,
d3) cooling down the suspension preferably to 10° C., preferably at a rate about 20° C./hour and preferably stir,
d4) optionally, heating the suspension preferably up to 50° C., preferably at a rate about 10° C./hour and preferably with stirring, cooling down the suspension preferably to 10° C., preferably at a rate about 10° C./hour and preferably with stirring, heating the suspension preferably up to 50° C., preferably at a rate about 5° C./hour and preferably with stirring, cooling down the suspension preferably to 10° C., preferably at a rate about 5° C./hour and preferably with stirring, d5) heating the suspension preferably up to 25° C., preferably at a rate about 10° C./hour and preferably with stirring, d6) isolating new crystalline form III, preferably by filtration preferably under reduced pressure and optionally followed by drying or optionally by spray drying the suspension.

Vilanterol Trifenatate Form IV

The present invention further provides a new crystalline form of vilanterol trifenatate designated form IV, characterized by an X-ray powder diffraction pattern having the following characteristic diffraction angles (2Theta): 15.54°; 17.03°; 17.41°; 34.24° and 34.66°.

Figure 11:
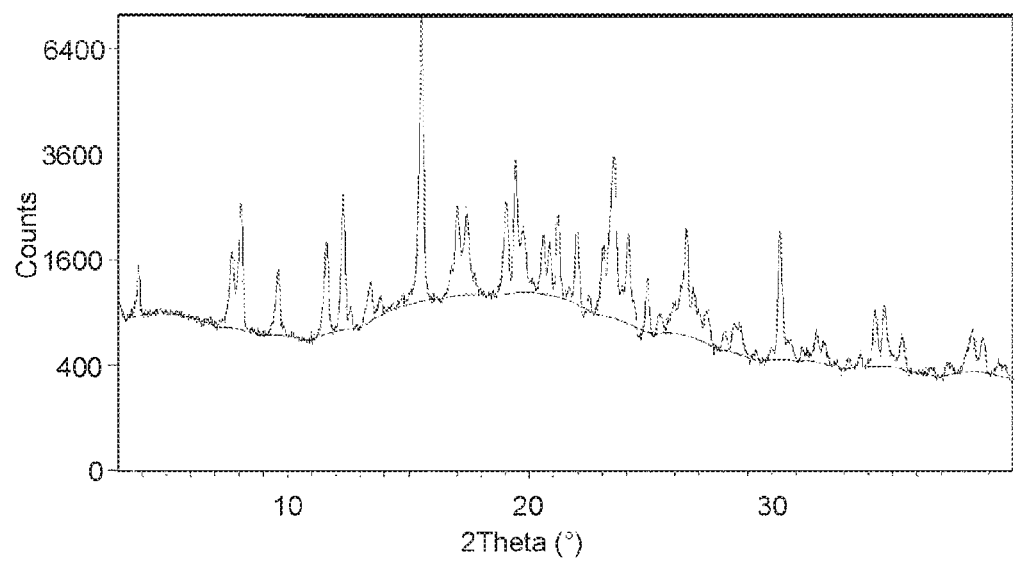
FIG. 11: XRPD diffractogram of new crystalline form IV of vilaterol trifenatate.

New crystalline form IV of vilanterol trifenatate has an X-ray powder diffraction pattern as depicted in FIG. 11 and shows the diffraction angles (2Theta) presented in table 5.

TABLE 5

X-ray powder diffraction peak list of vilanterol trifenatate crystalline form IV.

| Angle 2θ(°) | Height [cts] | d value (Å) | Intensity (%) |
|---|---|---|---|
| 3.87 | 617 | 22.82 | 10 |
| 7.70 | 996 | 11.48 | 16 |
| 8.11 | 1889 | 10.90 | 30 |
| 9.63 | 784 | 9.18 | 12 |
| 11.60 | 1190 | 7.63 | 19 |
| 12.32 | 1945 | 7.19 | 30 |
| 12.62 | 208 | 7.02 | 3 |
| 13.43 | 470 | 6.59 | 7 |
| 13.83 | 211 | 6.40 | 3 |
| 15.54 | 6401 | 5.70 | 100 |
| 17.03 | 1424 | 5.21 | 22 |
| 17.41 | 1286 | 5.10 | 20 |
| 19.02 | 1473 | 4.67 | 23 |
| 19.45 | 2335 | 4.56 | 36 |
| 19.70 | 921 | 4.51 | 14 |
| 20.59 | 897 | 4.31 | 14 |
| 20.85 | 806 | 4.26 | 13 |
| 21.17 | 1285 | 4.20 | 20 |
| 21.93 | 1112 | 4.05 | 17 |
| 22.47 | 197 | 3.96 | 3 |
| 23.04 | 963 | 3.86 | 15 |
| 23.49 | 2730 | 3.79 | 43 |
| 24.08 | 1257 | 3.70 | 20 |
| 24.31 | 280 | 3.66 | 4 |
| 24.86 | 647 | 3.58 | 10 |
| 25.33 | 180 | 3.52 | 3 |
| 25.97 | 339 | 3.43 | 5 |
| 26.50 | 1407 | 3.36 | 22 |
| 26.74 | 504 | 3.33 | 8 |
| 27.02 | 306 | 3.30 | 5 |
| 27.28 | 319 | 3.27 | 5 |
| 28.06 | 177 | 3.18 | 3 |
| 28.42 | 253 | 3.14 | 4 |
| 28.70 | 263 | 3.11 | 4 |
| 29.33 | 83 | 3.04 | 1 |
| 30.32 | 1636 | 2.95 | 26 |
| 30.82 | 159 | 2.90 | 2 |
| 31.24 | 111 | 2.86 | 2 |
| 31.83 | 303 | 2.81 | 5 |
| 32.17 | 187 | 2.78 | 3 |
| 33.13 | 63 | 2.70 | 1 |
| 33.67 | 98 | 2.66 | 2 |
| 34.24 | 522 | 2.62 | 8 |
| 34.66 | 584 | 2.59 | 9 |
| 35.40 | 290 | 2.54 | 5 |
| 36.62 | 46 | 2.45 | 1 |
| 37.23 | 77 | 2.41 | 1 |
| 38.28 | 329 | 2.35 | 5 |
| 38.68 | 242 | 2.33 | 4 |
| 38.81 | 240 | 2.32 | 4 |
| 39.36 | 96 | 2.29 | 2 |

Preparation of Form IV

The present invention provides a method for preparing form IV of vilanterol trifenatate comprising:

e1) suspending vilanterol trifenatate form II in cyclohexane, preferably in 24 vol., e2) heating the suspension preferably up to 50° C., preferably at a rate about 20° C./hour and preferably stir, e3) cooling down the suspension preferably to 10° C., preferably at a rate about 20° C./hour and preferably stir, e4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir, e5) heating the suspension preferably up to 25° C., preferably at a rate about 10° C./hour and preferably stir, e6) isolating new crystalline form IV, preferably by filtration preferably under reduced pressure and optionally followed by drying or optionally by spray drying the suspension.

Vilanterol Trifenatate Form V

This invention also discloses a new crystalline form of vilanterol trifenatate designated form V, characterized by a X-ray powder diffraction pattern having the following characteristic diffraction angles (2Theta): 15.51'; 17.22°; 20.33°; 24.34° and 26.95°.

Figure 12:
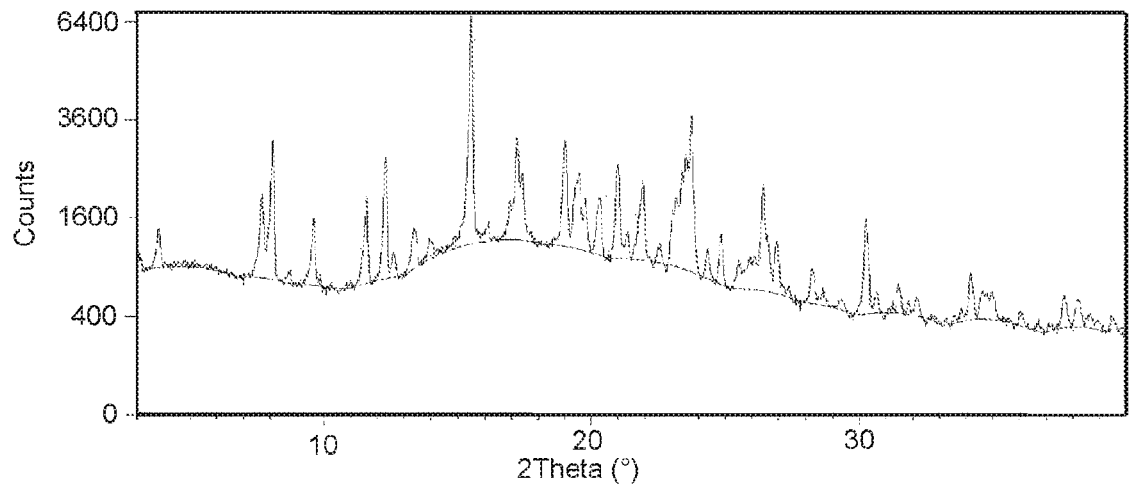
FIG. 12: XRPD diffractogram of new crystalline form V of vilaterol trifenatate.

New crystalline form V of vilanterol trifenatate has an X-ray powder diffraction pattern as depicted in FIG. 12 and shows the diffraction angles (2Theta) presented in table 6.

TABLE 6

X-ray powder diffraction peak list of vilanterol trifenatate crystalline form V.

| Angle 2θ (°) | Height [cts] | d value (Å) | Intensity (%) |
|---|---|---|---|
| 3.82 | 577 | 23.16 | 11 |
| 7.70 | 1232 | 11.48 | 23 |
| 8.10 | 2389 | 10.91 | 44 |
| 8.72 | 139 | 10.14 | 3 |
| 9.63 | 922 | 9.19 | 17 |
| 11.59 | 1317 | 7.63 | 24 |
| 12.31 | 1931 | 7.19 | 36 |
| 12.59 | 301 | 7.03 | 6 |
| 13.35 | 534 | 6.63 | 10 |
| 14.00 | 248 | 6.32 | 5 |
| 15.51 | 5440 | 5.71 | 100 |
| 16.11 | 231 | 5.50 | 4 |
| 16.93 | 581 | 5.24 | 11 |
| 17.22 | 1888 | 5.15 | 35 |
| 17.42 | 1078 | 5.09 | 20 |
| 19.02 | 1899 | 4.67 | 35 |
| 19.35 | 933 | 4.59 | 17 |
| 19.56 | 1283 | 4.54 | 24 |
| 19.78 | 830 | 4.49 | 15 |
| 20.33 | 911 | 4.37 | 17 |
| 21.00 | 1579 | 4.23 | 29 |
| 21.35 | 379 | 4.16 | 7 |
| 21.93 | 1245 | 4.05 | 23 |
| 22.53 | 184 | 3.95 | 3 |
| 23.02 | 874 | 3.86 | 16 |
| 23.17 | 1074 | 3.84 | 20 |
| 23.37 | 1571 | 3.81 | 29 |
| 23.53 | 1917 | 3.78 | 35 |
| 23.75 | 2894 | 3.75 | 53 |
| 24.34 | 394 | 3.66 | 7 |
| 24.82 | 651 | 3.59 | 12 |
| 25.51 | 289 | 3.49 | 5 |
| 25.94 | 375 | 3.43 | 7 |
| 26.41 | 1571 | 3.37 | 29 |
| 26.62 | 547 | 3.35 | 10 |

TABLE 6-continued

X-ray powder diffraction peak list of vilanterol trifenatate crystalline form V.

| Angle 2θ (°) | Height [cts] | d value (Å) | Intensity (%) |
|---|---|---|---|
| 26.95 | 629 | 3.31 | 12 |
| 27.39 | 100 | 3.26 | 2 |
| 28.23 | 364 | 3.16 | 7 |
| 28.67 | 96 | 3.11 | 2 |
| 29.30 | 88 | 3.05 | 2 |
| 30.25 | 1164 | 2.95 | 21 |
| 30.68 | 182 | 2.91 | 3 |
| 31.46 | 284 | 2.84 | 5 |
| 31.83 | 109 | 2.81 | 2 |
| 32.13 | 168 | 2.79 | 3 |
| 32.83 | 38 | 2.73 | 1 |
| 33.83 | 111 | 2.65 | 2 |
| 34.17 | 469 | 2.62 | 9 |
| 34.60 | 244 | 2.59 | 4 |
| 34.99 | 267 | 2.56 | 5 |
| 36.04 | 111 | 2.49 | 2 |
| 36.72 | 53 | 2.45 | 1 |
| 37.66 | 268 | 2.39 | 5 |
| 38.14 | 229 | 2.36 | 4 |
| 38.67 | 107 | 2.33 | 2 |
| 39.48 | 79 | 2.28 | 1 |

Preparation of Form V

The present invention also provides a method for preparing form V of vilanterol trifenatate comprising:

f1) suspending vilanterol trifenatate form II in methylcyclohexane, preferably in 24 vol., f2) heating the suspension preferably up to 50° C., preferably at a rate about 20° C./hour and preferably stir, f3) cooling down the suspension preferably to 10° C., preferably at a rate about 20° C./hour and preferably stir, f4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir, f5) heating the suspension preferably up to 25° C., preferably at a rate about 10° C./hour and preferably stir, f6) isolating new crystalline form V, preferably by filtration preferably under reduced pressure and optionally followed by drying or optionally by spray drying the suspension.

Vilanterol Trifenatate Form VI

This invention also discloses a new crystalline form of vilanterol trifenatate designated form VI, characterized by an X-ray powder diffraction pattern having the following characteristic diffraction angles (2Theta): 6.03°; 11.47°; 13.62°; 20.63° and 21.49°.

Figure 13:
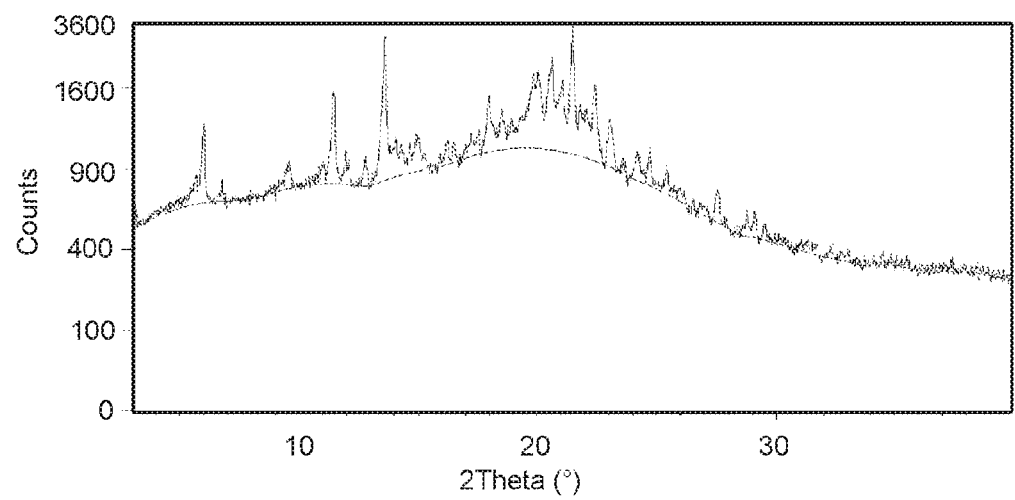
FIG. 13: XRPD diffractogram of new crystalline form VI of vilaterol trifenatate.

New form VI of vilanterol trifenatate has an X-ray powder diffraction pattern as depicted in FIG. 13 and shows the diffraction angles (2Theta) presented in table 7.

TABLE 7

X-ray powder diffraction peak list of vilanterol trifenatate crystalline form VI.

| Angle 2θ (°) | Height [cts] | d value (Å) | Intensity (%) |
|---|---|---|---|
| 5.70 | 205 | 15.52 | 15 |
| 6.03 | 607 | 14.65 | 45 |
| 9.60 | 196 | 9.21 | 15 |
| 11.47 | 787 | 7.72 | 58 |
| 11.95 | 198 | 7.41 | 15 |
| 12.80 | 188 | 6.92 | 14 |
| 13.62 | 1345 | 6.50 | 100 |
| 14.06 | 252 | 6.30 | 19 |
| 14.92 | 259 | 5.94 | 19 |
| 16.20 | 169 | 5.47 | 13 |
| 16.47 | 141 | 5.38 | 10 |
| 17.55 | 207 | 5.05 | 15 |
| 17.98 | 467 | 4.93 | 35 |
| 18.48 | 322 | 4.80 | 24 |
| 20.04 | 728 | 4.43 | 54 |
| 20.63 | 874 | 4.31 | 65 |
| 21.05 | 641 | 4.22 | 48 |
| 21.49 | 1304 | 4.14 | 97 |
| 22.07 | 403 | 4.03 | 30 |
| 22.44 | 661 | 3.96 | 49 |
| 23.01 | 393 | 3.87 | 29 |
| 23.61 | 100 | 3.77 | 7 |
| 24.23 | 201 | 3.67 | 15 |
| 24.71 | 265 | 3.60 | 20 |
| 25.43 | 191 | 3.50 | 14 |
| 26.08 | 60 | 3.42 | 4 |
| 26.91 | 58 | 3.31 | 4 |
| 27.61 | 198 | 3.23 | 15 |
| 28.79 | 154 | 3.10 | 11 |
| 29.13 | 137 | 3.07 | 10 |
| 29.54 | 84 | 3.02 | 6 |
| 31.51 | 39 | 2.84 | 3 |
| 32.30 | 44 | 2.77 | 3 |
| 35.43 | 25 | 2.53 | 2 |
| 37.40 | 47 | 2.40 | 4 |

Preparation of Form VI

The present invention further provides a method for preparing form VI of vilanterol trifenatate comprising:

g1) suspending vilanterol trifenatate form II in 2-propanol, preferably in 24 vol., g2) heating the suspension preferably up to 50° C., preferably at a rate about 20° C./hour and preferably stir, g3) cooling down the suspension preferably to 10° C., preferably at a rate about 20° C./hour and preferably stir, g4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir, g5) heating the suspension preferably up to 25° C., preferably at a rate about 10° C./hour and preferably stir, g6) isolating new crystalline form VI, preferably by filtration preferably under reduced pressure and optionally followed by drying or optionally by spray drying the suspension.

Vilanterol Trifenatate Form VII

This invention still further discloses a new crystalline form of vilanterol trifenatate designated form VII, characterized by an X-ray powder diffraction pattern having the following characteristic diffraction angles (2Theta): 9.26°; 10.71'; 14.01'; 20.24° and 25.67°.

Figure 14:
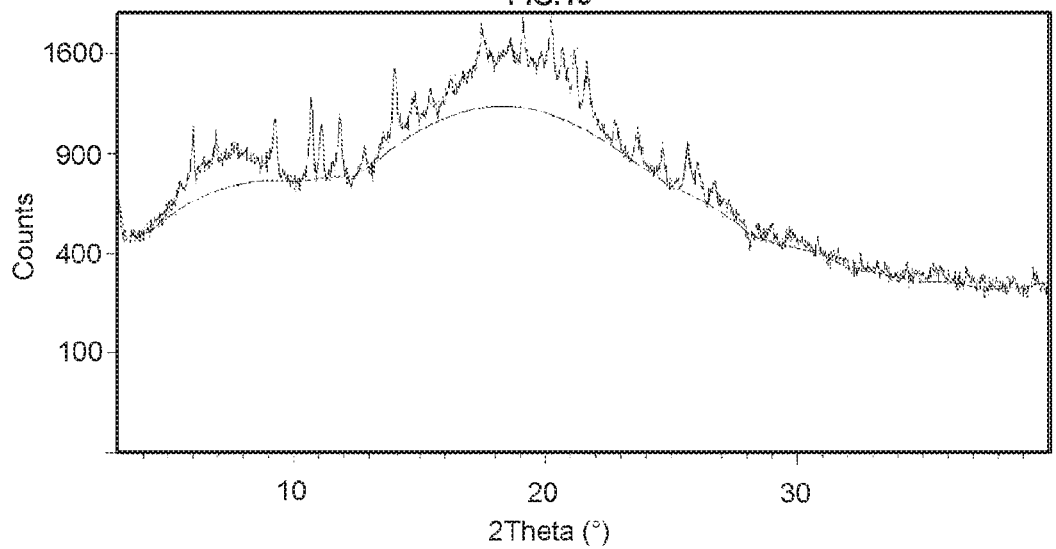
FIG. 14: XRPD diffractogram of new crystalline form VII of vilaterol trifenatate.

New form VII of vilanterol trifenatate has an X-ray powder diffraction pattern as depicted in FIG. 14 and shows the diffraction angles (2Theta) presented in table 8.

TABLE 8

X-ray powder diffraction peak list of vilanterol trifenatate crystalline form VII.

| Angle 2θ (°) | Height [cts] | d value (Å) | Intensity (%) |
|---|---|---|---|
| 6.02 | 426 | 14.69 | 53 |
| 6.94 | 325 | 12.74 | 41 |
| 7.71 | 215 | 11.46 | 27 |
| 9.26 | 358 | 9.55 | 45 |
| 10.71 | 521 | 8.26 | 65 |
| 11.15 | 294 | 7.94 | 37 |
| 11.84 | 385 | 7.48 | 48 |
| 12.80 | 115 | 6.92 | 14 |
| 14.01 | 532 | 6.32 | 67 |
| 14.77 | 229 | 6.00 | 29 |
| 15.44 | 242 | 5.74 | 30 |
| 16.23 | 272 | 5.46 | 34 |
| 17.46 | 644 | 5.08 | 81 |
| 18.60 | 503 | 4.77 | 63 |
| 19.11 | 711 | 4.64 | 89 |
| 20.24 | 798 | 4.39 | 100 |
| 20.69 | 527 | 4.29 | 66 |
| 21.17 | 553 | 4.20 | 69 |
| 21.66 | 461 | 4.10 | 58 |
| 22.76 | 191 | 3.91 | 24 |
| 23.64 | 165 | 3.76 | 21 |
| 24.65 | 207 | 3.61 | 26 |
| 25.67 | 296 | 3.47 | 37 |
| 26.06 | 203 | 3.42 | 25 |
| 26.73 | 148 | 3.34 | 19 |
| 27.18 | 64 | 3.28 | 8 |
| 28.96 | 76 | 3.08 | 10 |
| 29.76 | 57 | 3.00 | 7 |
| 30.19 | 29 | 2.96 | 4 |
| 35.61 | 44 | 2.52 | 5 |
| 36.79 | 42 | 2.44 | 5 |
| 39.46 | 28 | 2.28 | 4 |

Preparation of Form VII

The present invention accordingly provides a method for preparing form VII of vilanterol trifenatate comprising:

h1) suspending vilanterol trifenatate form II in 3-methyl-1-butanol, preferably in 24 vol., h2) heating the suspension preferably up to 50° C., preferably at a rate about 20° C./hour and preferably stir, h3) cooling down the suspension preferably to 10° C., preferably at a rate about 20° C./hour and preferably stir, h4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir, h5) heating the suspension preferably up to 25° C., preferably at a rate about 10° C./hour and preferably stir, h6) isolating new crystalline form VII, preferably by filtration preferably under reduced pressure and optionally followed by drying or optionally by spray drying the suspension.

Vilanterol Trifenatate Form VIII

Still further, this invention discloses a new crystalline form of vilanterol trifenatate designated form VIII, characterized by an X-ray powder diffraction pattern having the following characteristic diffraction angles (2Theta): 8.89°; 12.48°; 13.92°; 14.25° and 21.79°.

Figure 15:
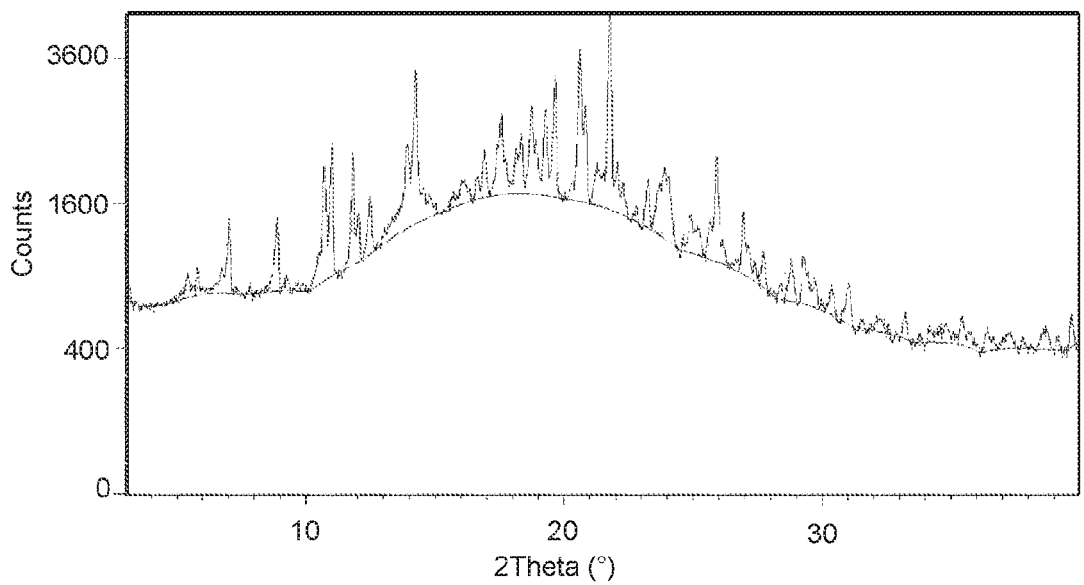
FIG. 15: XRPD diffractogram of new crystalline form VIII of vilaterol trifenatate.

New form VIII of vilanterol trifenatate has an X-ray powder diffraction pattern as depicted in FIG. 15 and shows the diffraction angles (2Theta) presented in table 9.

TABLE 9

X-ray powder diffraction peak list of vilanterol trifenatate crystalline form VIII.

| Angle 2θ (°) | Height [cts] | d value (Å) | Intensity (%) |
|---|---|---|---|
| 5.42 | 176 | 16.32 | 6 |
| 5.81 | 201 | 15.22 | 7 |
| 7.03 | 657 | 12.58 | 23 |
| 8.89 | 667 | 9.94 | 23 |
| 9.29 | 87 | 9.52 | 3 |
| 9.80 | 43 | 9.03 | 2 |
| 10.74 | 1169 | 8.24 | 41 |
| 11.01 | 1366 | 8.03 | 48 |
| 11.82 | 1182 | 7.48 | 42 |
| 12.03 | 467 | 7.35 | 16 |
| 12.48 | 576 | 7.09 | 20 |
| 13.92 | 958 | 6.36 | 34 |
| 14.25 | 2012 | 6.22 | 71 |
| 16.09 | 255 | 5.51 | 9 |
| 16.63 | 242 | 5.33 | 9 |
| 16.92 | 497 | 5.24 | 17 |
| 17.56 | 1060 | 5.05 | 37 |
| 18.14 | 574 | 4.89 | 20 |
| 18.35 | 764 | 4.84 | 27 |
| 18.75 | 1092 | 4.73 | 38 |
| 18.91 | 658 | 4.69 | 23 |
| 19.28 | 1099 | 4.60 | 39 |
| 19.66 | 1578 | 4.52 | 55 |
| 20.63 | 2028 | 4.31 | 71 |
| 20.84 | 1274 | 4.26 | 45 |
| 21.27 | 419 | 4.18 | 15 |
| 21.79 | 2846 | 4.08 | 100 |
| 22.07 | 606 | 4.03 | 21 |
| 22.31 | 366 | 3.98 | 13 |
| 22.81 | 166 | 3.90 | 6 |
| 23.28 | 505 | 3.82 | 18 |
| 23.67 | 512 | 3.76 | 18 |
| 23.91 | 803 | 3.72 | 28 |
| 24.09 | 729 | 3.69 | 26 |
| 24.90 | 376 | 3.58 | 13 |
| 25.28 | 242 | 3.52 | 9 |
| 25.64 | 358 | 3.47 | 13 |
| 25.93 | 1150 | 3.44 | 40 |
| 26.95 | 587 | 3.31 | 21 |
| 27.73 | 294 | 3.22 | 10 |
| 28.43 | 117 | 3.14 | 4 |
| 28.79 | 319 | 3.10 | 11 |
| 29.27 | 386 | 3.05 | 14 |
| 29.74 | 209 | 3.00 | 7 |
| 30.43 | 144 | 2.94 | 5 |
| 31.06 | 305 | 2.88 | 11 |
| 31.55 | 63 | 2.84 | 2 |
| 32.20 | 78 | 2.78 | 3 |
| 33.22 | 163 | 2.70 | 6 |
| 34.15 | 84 | 2.63 | 3 |
| 34.81 | 113 | 2.58 | 4 |
| 35.41 | 177 | 2.53 | 6 |
| 36.39 | 100 | 2.47 | 4 |
| 37.31 | 83 | 2.41 | 3 |
| 37.76 | 66 | 2.38 | 2 |
| 38.71 | 123 | 2.33 | 4 |
| 39.12 | 61 | 2.30 | 2 |
| 39.65 | 156 | 2.27 | 6 |

Preparation of Form VIII

The present invention additionally provides a method for preparing form VIII of vilanterol trifenatate comprising:

i1) suspending vilanterol trifenatate form II in anisole, preferably in 24 vol., i2) heating the suspension preferably up to 50° C., preferably at a rate about 20° C./hour and preferably stir, i3) cooling down the suspension preferably to 10° C., preferably at a rate about 20° C./hour and preferably stir, i4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir, i5) heating the suspension preferably up to 25° C., preferably at a rate about 10° C./hour and preferably stir, i6) isolating new crystalline form VIII, preferably by filtration preferably under reduced pressure and optionally followed by drying or optionally by spray drying the suspension.

Vilanterol Trifenatate Form IX

This invention additionally discloses a new crystalline form of vilanterol trifenatate designated form IX, characterized by an X-ray powder diffraction pattern having the following characteristic diffraction angles (2Theta): 6.01°; 7.04°; 16.86°; 24.78° and 29.29°.

Figure 16:
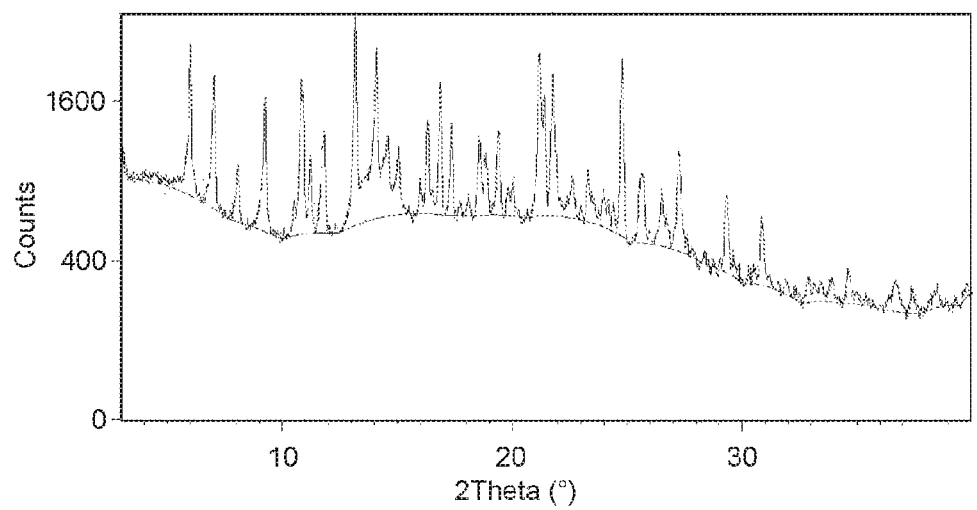
FIG. 16: XRPD diffractogram of new crystalline form IX of vilaterol trifenatate.

New form IX of vilanterol trifenatate has an X-ray powder diffraction pattern as depicted in FIG. 16 and shows the diffraction angles (2Theta) presented in table 10.

TABLE 10

X-ray powder diffraction peak list of vilanterol trifenatate crystalline form IX

| Angle 2θ (°) | Height [cts] | d value (Å) | Intensity (%) |
|---|---|---|---|
| 6.01 | 1462 | 14.71 | 73 |
| 7.04 | 1173 | 12.56 | 59 |
| 8.09 | 400 | 10.93 | 20 |
| 9.26 | 1073 | 9.55 | 54 |
| 10.49 | 189 | 8.43 | 9 |
| 10.81 | 1221 | 8.18 | 61 |
| 10.92 | 1125 | 8.10 | 56 |
| 11.23 | 533 | 7.88 | 27 |
| 11.71 | 595 | 7.56 | 30 |
| 11.84 | 774 | 7.48 | 39 |
| 13.18 | 2001 | 6.72 | 100 |
| 14.09 | 1540 | 6.29 | 77 |
| 14.57 | 612 | 6.08 | 31 |
| 15.06 | 513 | 5.88 | 26 |
| 15.99 | 251 | 5.54 | 13 |
| 16.31 | 767 | 5.43 | 38 |
| 16.86 | 1130 | 5.26 | 56 |
| 17.34 | 720 | 5.12 | 36 |
| 17.71 | 84 | 5.01 | 4 |
| 18.07 | 122 | 4.91 | 6 |
| 18.55 | 581 | 4.78 | 29 |
| 18.77 | 382 | 4.73 | 19 |
| 19.40 | 654 | 4.58 | 33 |
| 19.80 | 192 | 4.48 | 10 |
| 20.04 | 237 | 4.43 | 12 |
| 21.20 | 1484 | 4.19 | 74 |
| 21.42 | 971 | 4.15 | 49 |
| 21.77 | 1246 | 4.08 | 62 |
| 22.61 | 264 | 3.93 | 13 |
| 23.31 | 366 | 3.82 | 18 |
| 23.97 | 263 | 3.71 | 13 |
| 24.19 | 215 | 3.68 | 11 |
| 24.37 | 128 | 3.65 | 6 |
| 24.78 | 1501 | 3.59 | 75 |
| 25.73 | 398 | 3.46 | 20 |
| 26.51 | 373 | 3.36 | 19 |
| 27.25 | 694 | 3.27 | 35 |
| 28.76 | 33 | 3.10 | 2 |
| 29.29 | 429 | 3.05 | 21 |
| 30.85 | 386 | 2.90 | 19 |
| 32.89 | 83 | 2.72 | 4 |
| 33.41 | 76 | 2.68 | 4 |
| 33.87 | 82 | 2.65 | 4 |
| 34.60 | 140 | 2.59 | 7 |
| 36.69 | 112 | 2.45 | 6 |
| 37.41 | 75 | 2.40 | 4 |
| 38.53 | 78 | 2.34 | 4 |
| 39.28 | 18 | 2.29 | 1 |

Preparation of Form IX

In another embodiment, the present invention provides a method for preparing form IX of vilanterol trifenatate comprising:

j1) suspending vilanterol trifenatate form II in nitromethane, preferably in 24 vol., j2) heating the suspension preferably up to 50° C., preferably at a rate about 20° C./hour and preferably stir, j3) cooling down the suspension preferably to 10° C., preferably at a rate about 20° C./hour and preferably stir, j4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir, j5) heating the suspension preferably up to 25° C., preferably at a rate about 10° C./hour and preferably stir, j6) isolating new crystalline form IX, preferably by filtration preferably under reduced pressure and optionally followed by drying or optionally by spray drying the suspension.

Vilanterol Trifenatate Form X

This invention moreover discloses a new crystalline form of vilanterol trifenatate designated form X, characterized by an X-ray powder diffraction pattern having the following characteristic diffraction angles (2Theta): 7.25°; 7.48°; 12.37°; 13.20° and 25.07°.

Figure 17:
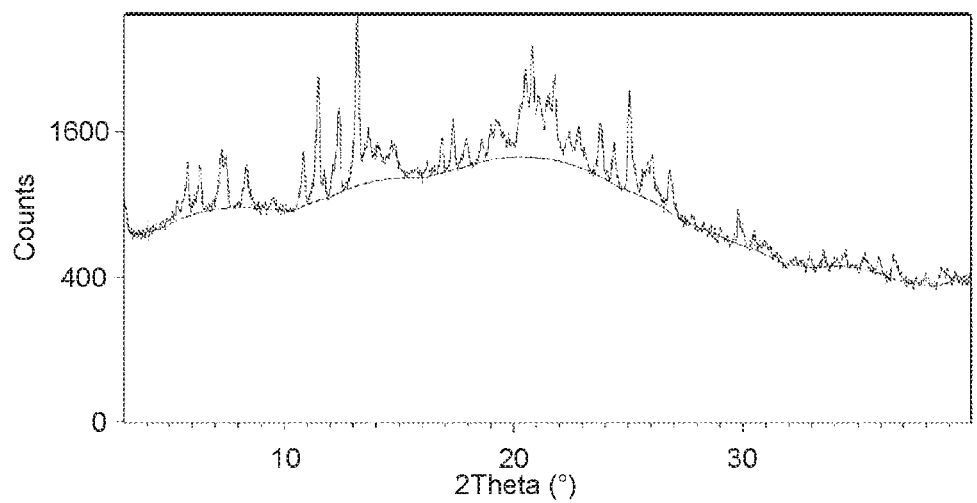
FIG. 17: XRPD diffractogram of new crystalline form X of vilaterol trifenatate.

New form X of vilanterol trifenatate has an X-ray powder diffraction pattern as depicted in FIG. 17 and shows the diffraction angles (2Theta) presented in table 11.

TABLE 11

X-ray powder diffraction peak list of vilanterol trifenatate crystalline form X.

| Angle 2θ (°) | Height [cts] | d value (Å) | Intensity (%) |
|---|---|---|---|
| 5.35 | 135 | 16.53 | 7 |
| 5.81 | 476 | 15.22 | 23 |
| 6.34 | 393 | 13.94 | 19 |
| 7.25 | 484 | 12.19 | 23 |
| 7.48 | 489 | 11.82 | 24 |
| 8.36 | 397 | 10.57 | 19 |
| 9.52 | 101 | 9.29 | 5 |
| 10.85 | 502 | 8.16 | 24 |
| 11.48 | 1323 | 7.71 | 64 |
| 11.77 | 196 | 7.52 | 9 |
| 12.37 | 859 | 7.15 | 41 |
| 13.20 | 2073 | 6.71 | 100 |
| 13.68 | 473 | 6.47 | 23 |
| 14.10 | 335 | 6.28 | 16 |
| 14.75 | 318 | 6.01 | 15 |
| 15.68 | 84 | 5.65 | 4 |
| 16.88 | 337 | 5.25 | 16 |
| 17.36 | 567 | 5.11 | 27 |
| 17.91 | 238 | 4.95 | 11 |
| 18.61 | 201 | 4.77 | 10 |
| 18.98 | 295 | 4.68 | 14 |
| 19.23 | 418 | 4.61 | 20 |
| 20.50 | 970 | 4.33 | 47 |
| 20.80 | 1223 | 4.27 | 59 |
| 21.10 | 700 | 4.21 | 34 |
| 21.49 | 638 | 4.13 | 31 |
| 21.81 | 1010 | 4.08 | 49 |
| 22.40 | 287 | 3.97 | 14 |
| 22.83 | 435 | 3.89 | 21 |
| 23.83 | 504 | 3.73 | 24 |
| 24.38 | 410 | 3.65 | 20 |
| 25.07 | 1023 | 3.55 | 49 |
| 26.06 | 445 | 3.42 | 21 |
| 26.80 | 377 | 3.33 | 18 |

TABLE 11-continued

X-ray powder diffraction peak list of vilanterol trifenatate crystalline form X.

| Angle 2θ (°) | Height [cts] | d value (Å) | Intensity (%) |
|---|---|---|---|
| 27.81 | 64 | 3.21 | 3 |
| 29.06 | 54 | 3.07 | 3 |
| 29.76 | 253 | 3.00 | 12 |
| 30.47 | 85 | 2.93 | 4 |
| 31.04 | 65 | 2.88 | 3 |
| 32.87 | 56 | 2.73 | 3 |
| 33.53 | 67 | 2.67 | 3 |
| 34.46 | 72 | 2.60 | 4 |
| 35.29 | 71 | 2.54 | 3 |
| 35.89 | 89 | 2.50 | 4 |
| 36.55 | 120 | 2.46 | 6 |
| 38.66 | 82 | 2.33 | 4 |

Preparation of Form X

The present invention also provides a method for preparing form X of vilanterol trifenatate comprising:

k1) suspending vilanterol trifenatate form I in a binary solvent mixture, preferably a ratio of 50:50 of, for example, cyclohexane:ethanol or heptane:ethanol, more preferably in 24 vols.

k2) heating the suspension preferably up to 50° C., preferably at a rate about 20° C./hour and preferably stir, k3) cooling down the suspension preferably to 10° C., preferably at a rate about 20° C./hour and preferably stir, k4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir, k5) heating the suspension preferably up to 25° C., preferably at a rate about 10° C./hour and preferably stir, k6) isolating new crystalline form X, preferably by filtration preferably under reduced pressure and optionally followed by drying or optionally by spray drying the suspension.

Alternatively, the present invention provides a method for preparing form X of vilanterol trifenatate comprising:

l1) suspending vilanterol trifenatate form II in a binary mixture as described above, preferably 50:50 of cyclohexane:ethanol or heptane:ethanol, preferably in 24 vol., l2) heating the suspension preferably up to 50° C., preferably at a rate about 20° C./hour and preferably stir, l3) cooling down the suspension preferably to 10° C., preferably at a rate about 20° C./hour and preferably stir, l4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir, l5) heating the suspension preferably up to 25° C., preferably at a rate about 10° C./hour and preferably stir, l6) isolating new crystalline form X, preferably by filtration preferably under reduced pressure and optionally followed by drying or optionally by spray drying the suspension.

Vilanterol Trifenatate Form XI

In another embodiment, this invention discloses a new crystalline form of vilanterol trifenatate designated form XI, characterized by an X-ray powder diffraction pattern having the following characteristic diffraction angles (2Theta): 14.09°; 18.52°; 20.95°; 23.28° and 29.31°.

Figure 18:
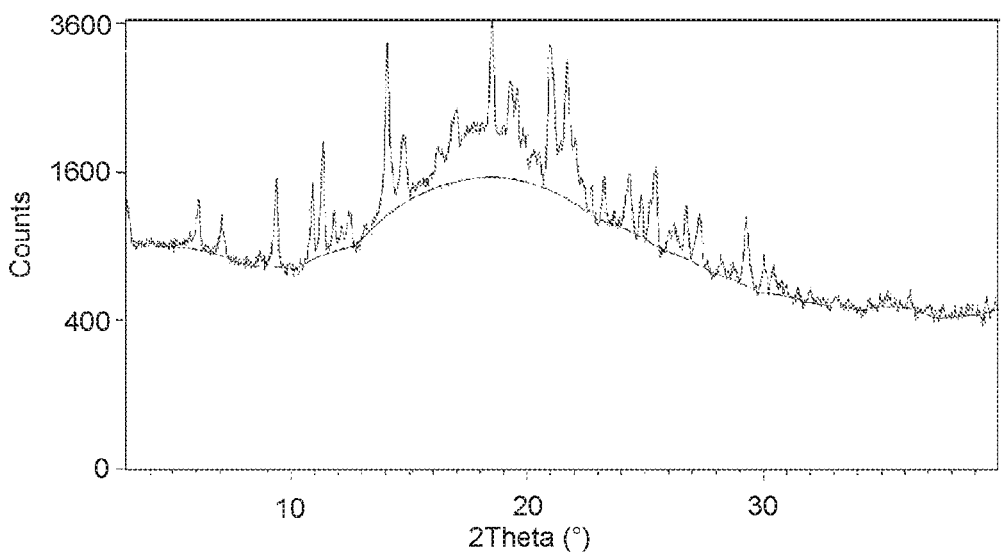
FIG. 18: XRPD diffractogram of new crystalline form XI of vilaterol trifenatate.

New form XI of vilanterol trifenatate has an X-ray powder diffraction pattern as depicted in FIG. 18 and shows the diffraction angles (2Theta) presented in table 12.

TABLE 12

X-ray powder diffraction peak list of vilanterol trifenatate crystalline form XI.

| Angle 2θ (°) | Height [cts] | d value (Å) | Intensity (%) |
|---|---|---|---|
| 6.10 | 446 | 14.49 | 21 |
| 7.10 | 329 | 12.46 | 15 |
| 8.69 | 73 | 10.17 | 3 |
| 9.40 | 771 | 9.41 | 36 |
| 10.93 | 644 | 8.10 | 30 |
| 11.36 | 1122 | 7.79 | 53 |
| 11.82 | 315 | 7.48 | 15 |
| 12.15 | 190 | 7.29 | 9 |
| 12.50 | 268 | 7.08 | 13 |
| 13.12 | 71 | 6.75 | 3 |
| 14.09 | 2130 | 6.29 | 100 |
| 14.73 | 747 | 6.01 | 35 |
| 14.86 | 618 | 5.96 | 29 |
| 16.17 | 435 | 5.48 | 20 |
| 17.02 | 862 | 5.21 | 40 |
| 17.70 | 580 | 5.01 | 27 |
| 18.52 | 2025 | 4.79 | 95 |
| 19.36 | 1065 | 4.58 | 50 |
| 19.57 | 1106 | 4.54 | 52 |
| 19.86 | 495 | 4.47 | 23 |
| 20.24 | 303 | 4.39 | 14 |
| 20.53 | 353 | 4.33 | 17 |
| 20.95 | 1666 | 4.24 | 78 |
| 21.15 | 1297 | 4.20 | 61 |
| 21.71 | 1728 | 4.09 | 81 |
| 22.06 | 717 | 4.03 | 34 |
| 22.42 | 252 | 3.97 | 12 |
| 22.76 | 296 | 3.91 | 14 |
| 23.28 | 447 | 3.82 | 21 |
| 24.36 | 553 | 3.65 | 26 |
| 24.85 | 401 | 3.58 | 19 |
| 25.22 | 412 | 3.53 | 19 |
| 25.47 | 725 | 3.50 | 34 |
| 26.24 | 263 | 3.40 | 12 |
| 26.70 | 373 | 3.34 | 17 |
| 27.29 | 438 | 3.27 | 21 |
| 28.21 | 135 | 3.16 | 6 |
| 28.80 | 79 | 3.10 | 4 |
| 29.31 | 541 | 3.05 | 25 |
| 30.04 | 268 | 2.97 | 13 |
| 30.42 | 154 | 2.94 | 7 |
| 31.47 | 53 | 2.84 | 3 |
| 31.99 | 73 | 2.80 | 3 |
| 33.06 | 55 | 2.71 | 3 |
| 34.50 | 46 | 2.60 | 2 |
| 35.22 | 59 | 2.55 | 3 |
| 36.23 | 96 | 2.48 | 5 |
| 37.02 | 52 | 2.43 | 2 |
| 37.65 | 53 | 2.39 | 3 |
| 39.48 | 84 | 2.28 | 4 |

Preparation of Form XI

The present invention provides a method for preparing form XI of vilanterol trifenatate comprising:

m1) suspending vilanterol trifenatate form II in binary mixture, preferably 50:50 of cyclohexane:2-methyltetrahydrofuran, preferably in 24 vol., m2) heating the suspension preferably up to 50° C., preferably at a rate about 20° C./hour and preferably stir, m3) cooling down the suspension preferably to 10° C., preferably at a rate about 20° C./hour and preferably stir, m4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir, m5) heating the suspension preferably up to 25° C., preferably at a rate about 10° C./hour and preferably stir, m6) isolating new crystalline form XI, preferably by filtration preferably under reduced pressure and optionally followed by drying or optionally by spray drying the suspension.

Vilanterol Trifenatate Form XII

This invention discloses a new crystalline form of vilanterol trifenatate designated orm XII, characterized by an X-ray powder diffraction pattern having the following characteristic diffraction angles (2Theta): 13.84°; 14.86°; 17.01'; 19.76° and 22.00°.

Figure 19:
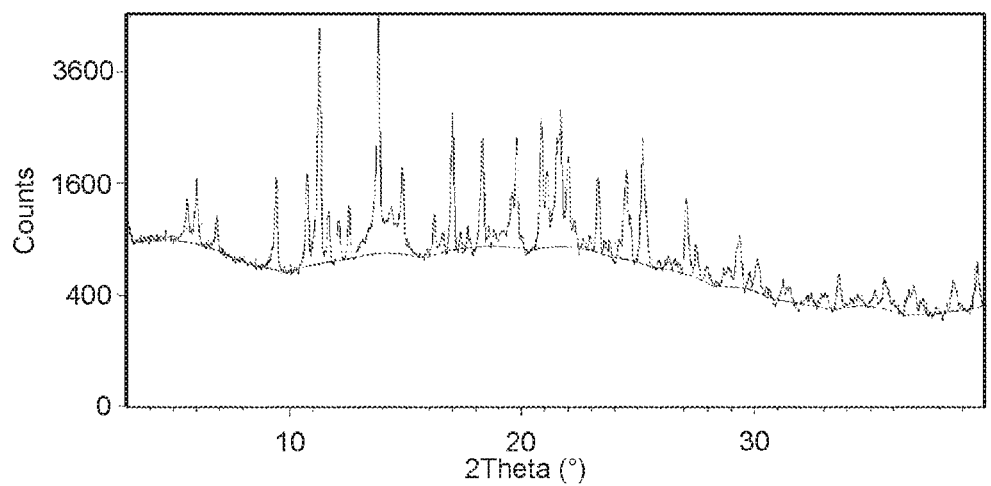
FIG. 19: XRPD diffractogram of new crystalline form XII of vilaterol trifenatate.

New form XII of vilanterol trifenatate has an X-ray powder diffraction pattern as depicted in FIG. 19 and shows the diffraction angles (2Theta) presented in table 13.

TABLE 13

X-ray powder diffraction peak list of vilanterol trifenatate crystalline form XII.

| Angle 2θ (°) | Height [cts] | d value (Å) | Intensity (%) |
|---|---|---|---|
| 5.61 | 480 | 15.75 | 12 |
| 6.01 | 837 | 14.70 | 21 |
| 6.89 | 396 | 12.83 | 10 |
| 9.44 | 1081 | 9.37 | 27 |
| 10.77 | 1120 | 8.22 | 28 |
| 11.30 | 4029 | 7.83 | 100 |
| 11.69 | 543 | 7.57 | 13 |
| 12.11 | 450 | 7.31 | 11 |
| 12.56 | 605 | 7.05 | 15 |
| 13.84 | 4025 | 6.40 | 100 |
| 14.36 | 513 | 6.17 | 13 |
| 14.86 | 1086 | 5.96 | 27 |
| 16.22 | 435 | 5.46 | 11 |
| 16.59 | 202 | 5.34 | 5 |
| 17.01 | 2000 | 5.21 | 50 |
| 17.36 | 172 | 5.11 | 4 |
| 17.64 | 241 | 5.03 | 6 |
| 18.31 | 1491 | 4.85 | 37 |
| 18.56 | 229 | 4.78 | 6 |
| 18.80 | 170 | 4.72 | 4 |
| 19.18 | 182 | 4.63 | 5 |
| 19.56 | 630 | 4.54 | 16 |
| 19.76 | 1534 | 4.49 | 38 |
| 20.83 | 1813 | 4.26 | 45 |
| 21.09 | 973 | 4.21 | 24 |
| 21.51 | 1459 | 4.13 | 36 |
| 21.69 | 1994 | 4.10 | 49 |
| 22.00 | 1176 | 4.04 | 29 |
| 22.26 | 302 | 3.99 | 8 |
| 22.92 | 165 | 3.88 | 4 |
| 23.27 | 954 | 3.82 | 24 |
| 23.81 | 124 | 3.74 | 3 |
| 24.18 | 184 | 3.68 | 5 |
| 24.52 | 993 | 3.63 | 25 |
| 24.68 | 464 | 3.61 | 12 |
| 25.19 | 1660 | 3.54 | 41 |
| 25.90 | 76 | 3.44 | 2 |
| 26.32 | 124 | 3.39 | 3 |
| 27.08 | 825 | 3.29 | 20 |
| 27.50 | 320 | 3.24 | 8 |
| 27.99 | 153 | 3.19 | 4 |
| 28.67 | 145 | 3.11 | 4 |
| 28.90 | 155 | 3.09 | 4 |
| 29.23 | 340 | 3.05 | 8 |
| 29.37 | 503 | 3.04 | 12 |
| 29.79 | 140 | 3.00 | 3 |
| 30.17 | 231 | 2.96 | 6 |
| 31.23 | 131 | 2.86 | 3 |
| 31.54 | 103 | 2.84 | 3 |

TABLE 13-continued

X-ray powder diffraction peak list of vilanterol trifenatate crystalline form XII.

| Angle 2θ (°) | Height [cts] | d value (Å) | Intensity (%) |
|---|---|---|---|
| 31.83 | 4 | 2.81 | 0 |
| 32.43 | 51 | 2.76 | 1 |
| 33.12 | 85 | 2.70 | 2 |
| 33.64 | 251 | 2.66 | 6 |
| 34.56 | 54 | 2.60 | 1 |
| 35.21 | 91 | 2.55 | 2 |
| 35.59 | 203 | 2.52 | 5 |
| 36.90 | 182 | 2.44 | 5 |
| 37.25 | 88 | 2.41 | 2 |
| 38.58 | 223 | 2.33 | 6 |
| 39.59 | 350 | 2.28 | 9 |

Preparation of form XII

The present invention moreover provides a method for preparing form XII of vilanterol trifenatate comprising:

n1) suspending vilanterol trifenatate form II in a binary mixture, preferably 50:50 of heptane: 1,2-dimethoxyethane, preferably in 24 vol., n2) heating the suspension preferably up to 50° C., preferably at a rate about 20° C./hour and preferably stir, n3) cooling down the suspension preferably to 10° C., preferably at a rate about 20° C./hour and preferably stir, n4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir, n5) heating the suspension preferably up to 25° C., preferably at a rate about 10° C./hour and preferably stir, n6) isolating new crystalline form XII, preferably by filtration preferably under reduced pressure and optionally followed by drying or optionally by spray drying the suspension.

Vilanterol Trifenatate Form XIII

This invention also discloses a new crystalline form of vilanterol trifenatate designated form XIII, characterized by an X-ray powder diffraction pattern having the following characteristic diffraction angles (2Theta): 9.76°; 16.78°; 18.40°; 18.60° and 21.08°.

Figure 20:
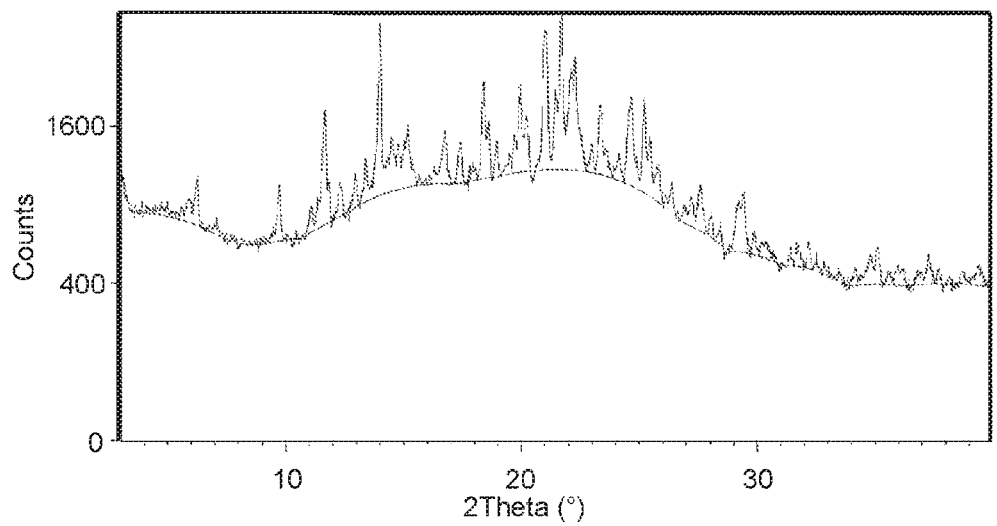
FIG. 20: XRPD diffractogram of new crystalline form XIII of vilaterol trifenatate.

New form XIII of vilanterol trifenatate has an X-ray powder diffraction pattern as depicted in FIG. 20 and shows the diffraction angles (2Theta) presented in table 14.

TABLE 14

X-ray powder diffraction peak list of vilanterol trifenatate crystalline form XIII.

| Angle 2θ (°) | Height [cts] | d value (Å) | Intensity (%) |
|---|---|---|---|
| 6.27 | 358 | 14.10 | 20 |
| 7.05 | 85 | 12.55 | 5 |
| 9.76 | 371 | 9.06 | 20 |
| 11.09 | 178 | 7.98 | 10 |
| 11.66 | 1012 | 7.59 | 56 |
| 11.87 | 305 | 7.46 | 17 |
| 12.29 | 249 | 7.20 | 14 |
| 12.96 | 218 | 6.83 | 12 |
| 13.40 | 329 | 6.61 | 18 |
| 14.00 | 1818 | 6.32 | 100 |
| 14.50 | 455 | 6.11 | 25 |
| 15.16 | 566 | 5.84 | 31 |

TABLE 14-continued

X-ray powder diffraction peak list of vilanterol trifenatate crystalline form XIII.

| Angle 2θ (°) | Height [cts] | d value (Å) | Intensity (%) |
|---|---|---|---|
| 16.78 | 437 | 5.29 | 24 |
| 17.44 | 349 | 5.09 | 19 |
| 18.40 | 960 | 4.82 | 53 |
| 18.60 | 525 | 4.77 | 29 |
| 18.96 | 314 | 4.68 | 17 |
| 19.71 | 340 | 4.50 | 19 |
| 19.94 | 839 | 4.45 | 46 |
| 20.23 | 497 | 4.39 | 27 |
| 20.97 | 1356 | 4.24 | 75 |
| 21.08 | 1424 | 4.22 | 78 |
| 21.47 | 799 | 4.14 | 44 |
| 21.69 | 1749 | 4.10 | 96 |
| 22.09 | 1024 | 4.02 | 56 |
| 22.30 | 1129 | 3.99 | 62 |
| 22.99 | 243 | 3.87 | 13 |
| 23.37 | 682 | 3.81 | 38 |
| 24.14 | 231 | 3.69 | 13 |
| 24.53 | 675 | 3.63 | 37 |
| 24.69 | 824 | 3.61 | 45 |
| 25.22 | 916 | 3.53 | 50 |
| 25.47 | 462 | 3.50 | 25 |
| 25.81 | 301 | 3.45 | 17 |
| 26.37 | 258 | 3.38 | 14 |
| 27.20 | 211 | 3.28 | 12 |
| 27.58 | 341 | 3.23 | 19 |
| 28.04 | 182 | 3.18 | 10 |
| 28.44 | 104 | 3.14 | 6 |
| 29.17 | 315 | 3.06 | 17 |
| 29.38 | 408 | 3.04 | 22 |
| 29.83 | 146 | 2.99 | 8 |
| 30.29 | 86 | 2.95 | 5 |
| 31.38 | 91 | 2.85 | 5 |
| 31.73 | 105 | 2.82 | 6 |
| 32.17 | 134 | 2.78 | 7 |
| 34.16 | 95 | 2.63 | 5 |
| 34.82 | 148 | 2.58 | 8 |
| 35.12 | 202 | 2.56 | 11 |
| 36.19 | 88 | 2.48 | 5 |
| 36.86 | 60 | 2.44 | 3 |
| 37.28 | 147 | 2.41 | 8 |
| 37.69 | 74 | 2.39 | 4 |
| 38.67 | 72 | 2.33 | 4 |

Preparation of Form XIII

The present invention provides a method for preparing form XIII of vilanterol trifenatate comprising:

o1) suspending vilanterol trifenatate form II in a binary mixture, preferably 50:50 of cyclohexane:methylethylketone or heptane:methylethylketone or mesitylene:methylethylketone, preferably in 24 vol., o2) heating the suspension preferably up to 50° C., preferably at a rate about 20° C./hour and preferably stir, o3) cooling down the suspension preferably to 10° C., preferably at a rate about 20° C./hour and preferably stir, o4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir, o5) heating the suspension preferably up to 25° C., preferably at a rate about 10° C./hour and preferably stir, o6) isolating new crystalline form XIII, preferably by filtration preferably under reduced pressure and optionally followed by drying or optionally by spray drying the suspension.

Vilanterol Trifenatate Form XIV

This invention further discloses a new crystalline form of vilanterol trifenatate designated form XIV, characterized by an X-ray powder diffraction pattern having the following characteristic diffraction angles (2Theta): 7.51°; 7.96°; 15.25°; 23.03° and 23.44°.

Figure 21:
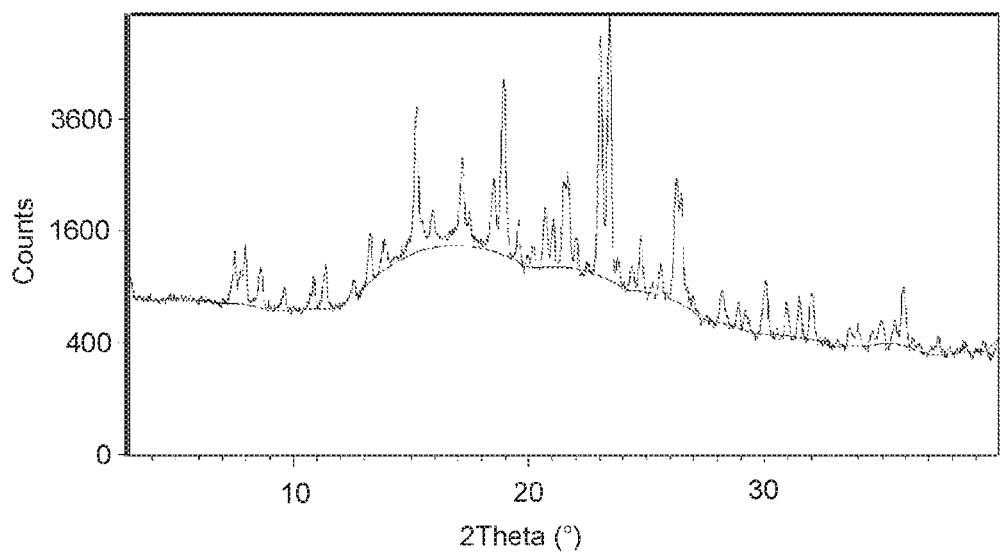
FIG. 21: XRPD diffractogram of new crystalline form XIV of vilaterol trifenatate.
Figure 22:
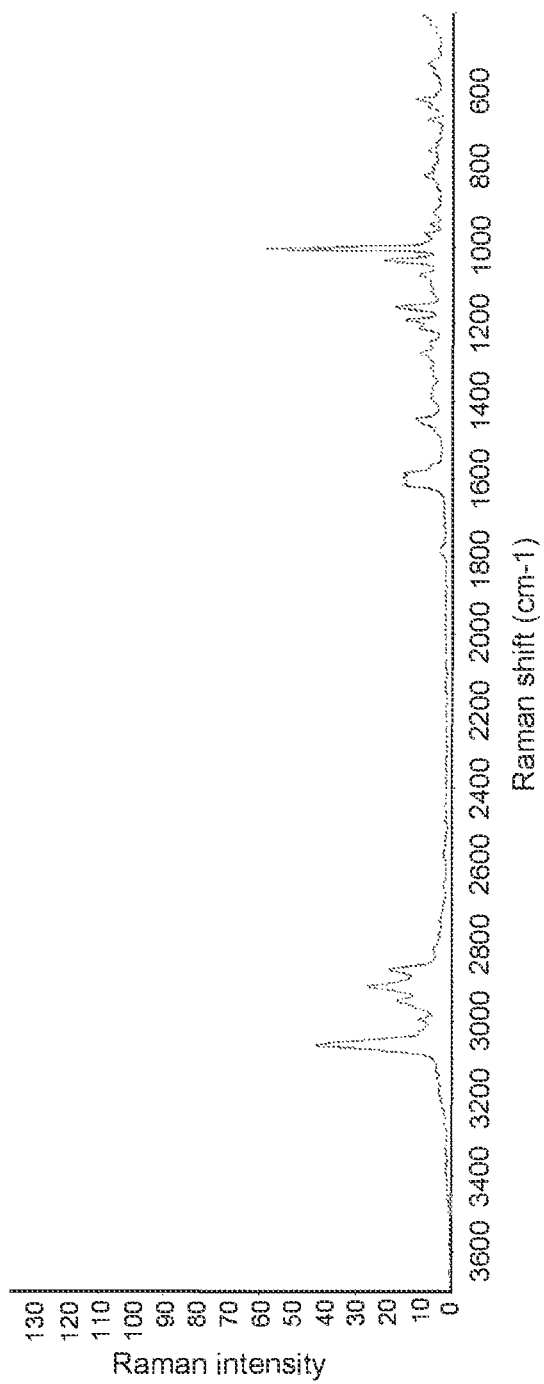
FIG. 22: FT-Raman spectrum of new crystalline form II of vilaterol trifenatate
Figure 23:
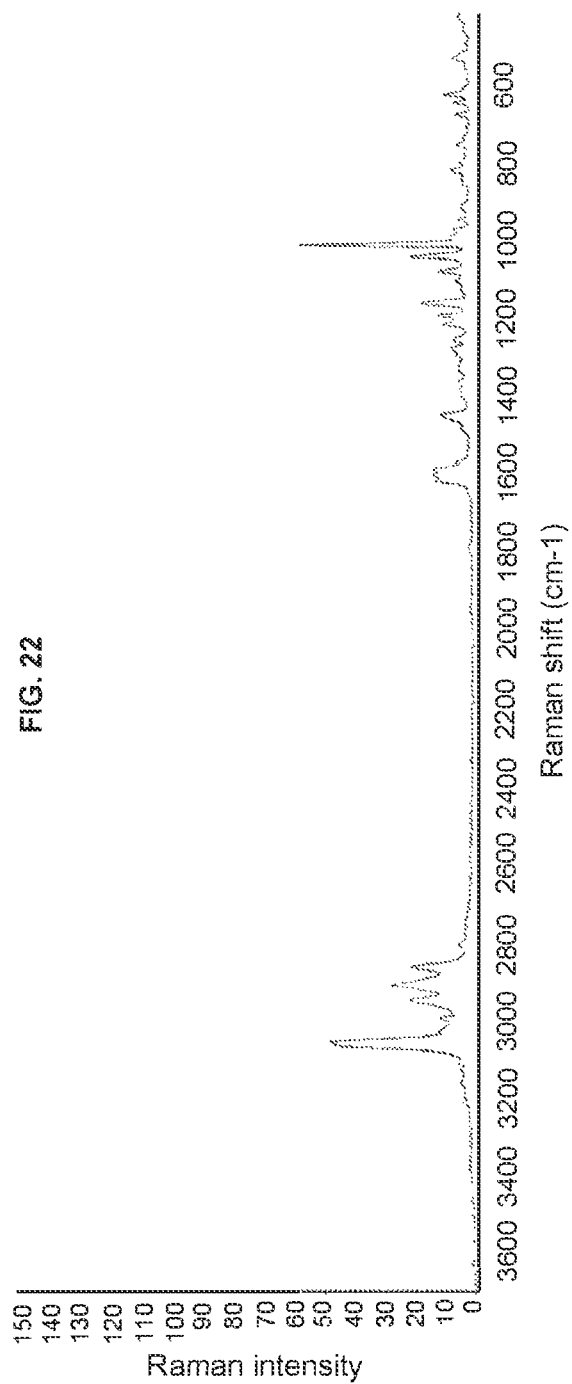
FIG. 23: FT-Raman spectrum of new crystalline form III of vilaterol trifenatate
Figure 24:
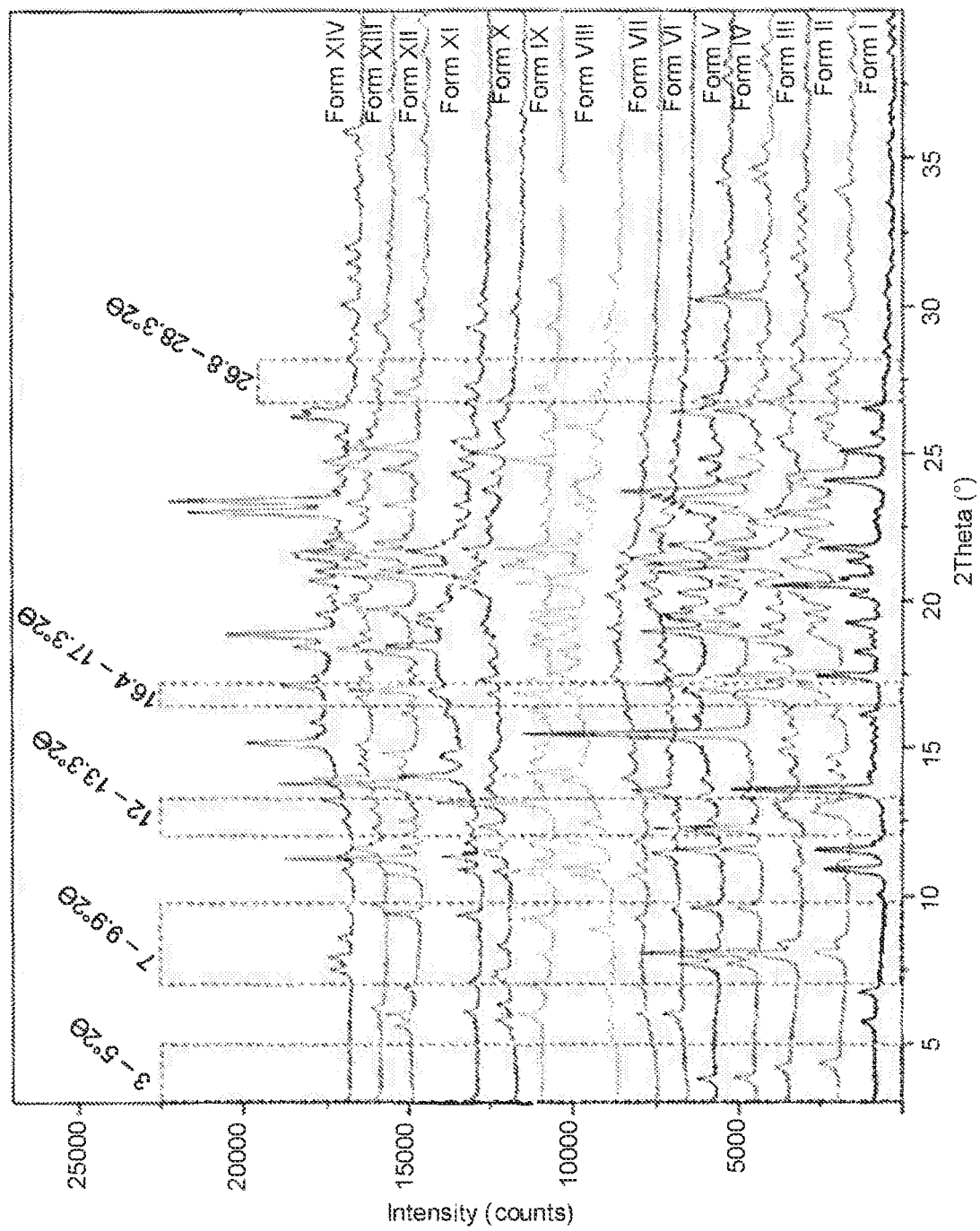
FIG. 24: XRPD diffractogram of new crystalline forms I to XIV (1 to 14) of vilaterol trifenatate

New form XIV of vilanterol trifenatate has an X-ray powder diffraction pattern as depicted in FIG. 21 and shows the diffraction angles (2Theta) presented in table 15.

TABLE 15

X-ray powder diffraction peak list of vilanterol trifenatate crystalline form XIV.

| Angle 2θ (°) | Height [cts] | d value (Å) | Intensity (%) |
|---|---|---|---|
| 7.51 | 586 | 11.77 | 11 |
| 7.96 | 713 | 11.11 | 14 |
| 8.64 | 420 | 10.24 | 8 |
| 9.61 | 213 | 9.20 | 4 |
| 10.87 | 280 | 8.14 | 5 |
| 11.37 | 481 | 7.78 | 9 |
| 12.56 | 147 | 7.05 | 3 |
| 13.28 | 602 | 6.67 | 12 |
| 13.86 | 353 | 6.39 | 7 |
| 15.25 | 2477 | 5.81 | 48 |
| 15.91 | 570 | 5.57 | 11 |
| 17.17 | 1436 | 5.17 | 28 |
| 17.48 | 505 | 5.07 | 10 |
| 18.52 | 1116 | 4.79 | 22 |
| 18.94 | 3156 | 4.69 | 61 |
| 19.60 | 486 | 4.53 | 9 |
| 20.18 | 283 | 4.40 | 5 |
| 20.75 | 751 | 4.28 | 15 |
| 21.07 | 682 | 4.22 | 13 |
| 21.50 | 1272 | 4.13 | 25 |
| 21.67 | 1303 | 4.10 | 25 |
| 22.00 | 387 | 4.04 | 8 |
| 22.48 | 106 | 3.96 | 2 |
| 23.03 | 4448 | 3.86 | 86 |
| 23.44 | 5151 | 3.80 | 100 |
| 23.76 | 337 | 3.75 | 7 |
| 24.36 | 248 | 3.65 | 5 |
| 24.74 | 684 | 3.60 | 13 |
| 25.24 | 109 | 3.53 | 2 |
| 25.60 | 315 | 3.48 | 6 |
| 26.23 | 1525 | 3.40 | 30 |
| 26.50 | 1392 | 3.36 | 27 |
| 27.00 | 162 | 3.30 | 3 |
| 28.23 | 335 | 3.16 | 7 |
| 28.91 | 197 | 3.09 | 4 |
| 29.21 | 151 | 3.06 | 3 |
| 30.09 | 505 | 2.97 | 10 |
| 30.94 | 302 | 2.89 | 6 |
| 31.48 | 365 | 2.84 | 7 |
| 31.97 | 381 | 2.80 | 7 |
| 33.60 | 152 | 2.67 | 3 |
| 33.99 | 146 | 2.64 | 3 |
| 34.55 | 89 | 2.60 | 2 |
| 34.96 | 178 | 2.57 | 3 |
| 35.54 | 186 | 2.53 | 4 |
| 35.88 | 477 | 2.50 | 9 |
| 37.41 | 117 | 2.40 | 2 |
| 38.54 | 44 | 2.34 | 1 |
| 39.42 | 29 | 2.29 | 1 |

Preparation of Form XIV

The present invention provides a method for preparing form XIV of vilanterol trifenatate comprising:

p1) suspending vilanterol trifenatate form III in methylcyclohexane, preferably in 24 vol., p2) heating the suspension preferably up to 50° C., preferably at a rate about 20° C./hour and preferably stir, p3) cooling down the suspension preferably to 10° C., preferably at a rate about 20° C./hour and preferably stir, p4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir, p5) heating the suspension preferably up to 25° C., preferably at a rate about 10° C./hour and preferably stir, p6) isolating new crystalline form XIV, preferably by filtration preferably under reduced pressure and optionally followed by drying or optionally by spray drying the suspension.

Advantages of Differentiated Solubility and Other Properties of the New Polymorphic Forms Surprisingly, it has been found that the processes of this invention afford new crystalline forms of vilanterol trifenatate that present favorable physical properties, such as differentiated solubility, particle morphology, low hygroscopicity and/or improved stability.

A summary of the solubilities of the polymorphs II and III, compound to known Form I, in various solvents is provided hereinbelow in Example 8.

A summary of other properties of the polymorphs of the invention is provided in Table 18, below. In table 18, polymorphs IV to XIV of the invention are indicated by Forms 4 to 14, respectively; and 'np' indicates test not performed.

TABLE 18

Summary of properties of polymorphs IV to XIV of the invention

| Analysis | Form 4 | Form 5 | Form 6 |
|---|---|---|---|
| Crystallization | SLHT(50PC1 + cooling to 20° C. (0.5° C./min) + SLRT (20° C.) from Cyclohexane | SLHT(50° C.) + cooling to 20° C. (0.5° C./min) + SLRT (20° C.) from Methylcyclohexane | SLHT(50° C.) + cooling to 25° C. + SLRT (25° C.) from 2-Propanol |
| XRPD | Form 4 | Form 5 | Form 6 |
| DSC (onset) | endo. 76° C. melting endo. 189° C. degradation | endo. 55-100° C. solvent loss endo. 134° C. Form 1 melting endo. 188° C. degradation | endo. 65° C. solvent loss endo. 80° C. solvent loss + Form 2 melting |
| TGA | Three consecutive solvent losses; approx. overall loss of 40% w/w/ Cyclohexane | Two consecutive weight losses; overall loss of 59% w/w Methylcyclohexane | One weight loss of 73% w/w 2-Propanol |
| EGA | Cyclohexane | Methylcyclohexane | 2-Propanol |
| Stability test (exposed sample 16 h) | Form 2 | Form 2 | Form 12 |
| Stability test (sealed vial 18 h) | Form 12 | Strong crystanllinity decrease | Form 6 |
| Stability test (25° C. 60% RH-7 d) | Np | Np | Form 1 (almost completely) |
| Stability test (60° C. 75% RH-3 d) | Np | Np | Amorphous |
| Hygroscopically (DVS) | Np | Np | Slightly hygroscopic |
| XRPD after DVS | Np | Np | Form 6 |

| Analysis | Form 7 | Form 8 | Form 9 | Form 10 |
|---|---|---|---|---|
| Crystallization | EXP 1: SLHT(50° C.) + cooling to 25° C. + SLRT (25° C.) from 3-Methyl-I-Butanol EXP 2: SLVT from 3-Methyl-I-Butanol | SLHT (50° C.) + cooling to 25° C. + SLRT (25° C.) from Anisole | EXP 1: SLHT (50° C.) + cooling to 25° C. + S:RT (25° C.) from Nitromethane EXP 2: SLVT from Nitromethane | SLHT (50° C.) + cooling to 25° C. + SLRT (25° C.) from 50:50 Cyclohexane:Ethanol |
| XRPD | EXP 1 = EXP 2 = Mixture of Form 11 and Form 12 | Form 8 | EXP 1: New Pattern EXP 2: Form 9 | Form 10 |
| DSC (onset) | Np | endo. 66° C. solvent loss endo. 136° C. solvent loss + melting endo. 191° C. degradation | endo. 68° C. solvent loss endo. 100° C. solvent loss + melting endo. 188° C. degradation | endo. 69° C. solvent loss + melting endo. 188° C. degradation |
| TGA | Np | Two consecutive weight losses; overall weight loss of approx. 68% w/w Anisole | Two consecutive weight losses; overall loss of 71% w/w Nitromethane | Two consecutive weight losses; overall loss of 60% w/w Ethanol |
| EGA | Np | Anisole | Nitromethane | Ethanol |
| Stability test (exposed sample 16 h) | Np | Form 8 | Form 9 | Form 10 |
| Stability test (sealed vial 18 h) | Np | Form 8 | Form 9 | Form 10 |
| Stability test (25° C. 60% RH-7 d) | Np | Strong crystallinity decrease (Form 12 conversion supposed) | Form 9 | Conversion to Form 1 |

TABLE 18-continued

Summary of properties of polymorphs IV to XIV of the invention

| | | | | |
|---|---|---|---|---|
| Stability test (60° C. 75% RH-3 d) | Np | Partial conversion to Form 12 | Partial conversion to Form 1 | Conversion to Form 1 |
| XRPD after Grinding | Np | Strong crystallinity decrease (partial conversion to Form 12) | Amorphous | Amorphous |
| Hygroscopically (DVS) | Np | Not hygroscopic | Slightly hygroscopic | Slightly hygroscopic |
| XRPD after DVS | Np | Form 8 | Low crystallinity degree | Conversion to Form 1 |

| Analysis | Form 11 | Form 12 | Form 13 | Form 14 |
|---|---|---|---|---|
| Crystallization | SLHT (50° C.) + cooling to 25° C. + SLRT (25° C.) from 50:50 Cyclohexane:2-Methyltetrahydrofuran | SLHT (50° C.) + cooling to 25° C. + SLRT (25° C.) from 50:50 Heptane:1,2-Dimethoxyethane | SLVT from 50:50 Mesitylene/Methyl ethyl ketone | SLVT from Methylcyclohexane |
| XRPD | Form 11 | Form 12 | Form 13 | Form 14 |
| DSC (onset) | endo. 50-100° C. solvent loss endo. 135° C. Form 1 melting endo. 188.6° C. degradation | endo. 21° C. solvent loss endo. 134° C. Form 1 melting endo. 189° C. degradation | endo. 54° C. solvent loss endo. 83° C. solvent loss exo. 93° C. recrystallization endo. 105° C. melting endo. 120° C. solvent loss endo. 189° C. degradation | endo. 58° C. solvent loss endo. 80° C. solvent loss + Form 3 melting |
| TGA | Four consecutive weight losses; overall loss of 51% w/w Cyclohexane and 2-Methyltetrahydrofuran | One loss of 61.6% w/w Water and 1,2-Dimethoxyethane | One loss of 34% w/w Water and Mesitylene | Several consecutive weight losses; overall one loss of 26% w/w Methylcyclohexane |
| EGA | Cyclohexane and 2-Methyltetrahydrofuran | Water and 1,2-Dimethoxyethane | Water and Mesitylene | Methylcyclohexane |
| Stability test (exposed sample 16 h) | Form 11 | Form 12 | Form 12 | Form 3 |
| Stability test (sealed vial 18 h) | Form 11 | Form 12 | Form 12 (almost completely) | Form 3 (almost completely) |
| Stability test (25° C. 60% RH-7 d) | Form 1 (start conversion) | Form 1 (almost completely) | Np | Np |
| Stability test (60° C. 75% RH-3 d) | Form 1 (almost completely) | Form 1 (almost completely | Np | Np |
| XRPD after Grinding | Form 12 | Amorphous (few signal of Form 12) | Np | Np |
| Hygroscopically (DVS) | Slightly hygroscopic | Slightly hygroscopic | Np | Np |
| XRPD after DVS | Ascribable to Form 11 | Ascribable to Form 1 | Np | Np |

Pharmaceutical Use and Formulations

The present invention further provides a method for the preparation of vilanterol trifenatate having a particle size suitable for inhalation, which method comprises providing a polymorphorph having the characteristics defined herein, in particular, form II, form III, form IV, form V, form, VI, form VII, form VIII, form IX, form X, form XI, form XII, form XIII or form XIV, or any combination thereof, and modifying the particle size to that suitable for inhalation.

For example, any one or more of vilanterol trifenatate forms II to XIV, obtained according to the present invention, is/are preferably micronized to obtain material having a particle size suitable for inhalation, preferably having a Dv90 less than 10 microns, more preferably less than 5 microns.

Therefore, the present invention also provides a micronization process for tailoring the particle size of a vilanterol trifenatate form whilst maintaining its crystalline form, which process comprises providing a polymorphorph having the characteristics defined herein, in particular, form II, form III, form IV, form V, form, VI, form VII, form VIII, form IX, form X, form XI, form XII, form XIII or form XIV, or any combination thereof, and modifying the particle size to that suitable for inhalation.

The present invention further provides a vilanterol trifenatate crystalline form as defined herein for use in medicine, particularly for use as a beta2 adrenoreceptor agonist, especially as a selective long-acting such agonist (LABA) and/or for use in the treatment of COPD, including chronic bronchitis and emphysema, and asthma.

The present invention still further provides the use of a vilanterol trifenatate crystalline form as defined herein in the preparation of a medicament, particularly wherein the medicament is for use as a beta2 adrenoreceptor agonist, especially as a selective long-acting beta2 adrenoreceptor agonist (LABA) and/or for use in the treatment of COPD, including chronic bronchitis and emphysema, and asthma.

The present invention also provides a method of treatment of a condition benefitting from or requiring administration of a beta2 adrenoreceptor such agonist (LABA), which method comprises administration to a patient in need thereof of an effective amount of a vilanterol trifenatate crystalline form as defined herein. Preferred conditions include COPD, including chronic bronchitis and emphysema, and asthma.

The present invention in another aspect provides a pharmaceutical composition comprising a vilanterol trifenatate crystalline form as defined herein in association with a pharmaceutically acceptable carrier therefor and optionally one or more additional active pharmaceutical ingredient(s) (APIs). Preferred additional APIs include fluticasone furoate and/or umeclidinium bromide.

The pharmaceutical compositions of the present invention may be presented in any form known in the art of pharmacy and suitable for these APIs and their purpose. In particular, such compositions may be suitable for inhalation, such as in powdered form, deliverable from foil-wrapped blisters. More preferably, the compositions of the present invention are in the form of micronized powders, having a particle size suitable for inhalation, preferably having a Dv90 less than 10 microns, e.g. less than 5 microns.

Especially preferred is when the compositions of the present invention are provided in association with instructions for use thereof, optionally including dosage information, dosing regime instructions and the like. Conveniently, the compositions of the present invention, together with any medical device such as inhalers, are packaged together in outer packaging which may include a carton, box or other suitable container for the composition and instructions.

EXAMPLES

The following examples are provided further to illustrate the new polymorphic forms and the processes of the present invention, and are not intended to be construed as limitations of the present invention; minor variations may be resorted to without departing from the spirit and scope of the present invention. Throughout this specification, any aspect, whether general, a sub-genus or specific, may be combined with any other aspect, as would be understood by a person skilled in this art.

Example 1: Preparation of Crystalline Form II of Vilanterol Trifenate 30 g of vilanterol trifenatate form I are suspended in 900 mL of acetone and the suspension heated up to 45° C. The clear solution is stirred for 2 h at a temperature up to 45° C. 90 mL of water is added to the clear solution and left to stir for 2 h at a temperature up to 45° C. The clear solution is slowly cooled down to a temperature of about 5-0° C. The crystalline form II is isolated by filtration under reduced pressure, and dried under reduced pressure at a temperature up to 50° C. Yield: 22.79 g (76% w/w).

Example 2: Preparation of Crystalline Form II of Vilanterol Trifenate with Seed 2.5 g of vilanterol trifenatate form I are suspended in 75 mL of acetone and the suspension heated up to 45° C. The clear solution is stirred for 2 h at a temperature up to 45° C. 90 mL of water is added to the clear solution and left to stir for 2 h at a temperature up to 45° C. The clear solution is slowly cooled down to a temperature of about 5-0° C. and a seed of crystalline form II added. The crystalline form II is isolated by filtration under reduced pressure, and dried under reduced pressure at a temperature up to 40° C. Yield: 1.39 g (56% w/w).

Example 3: Preparation of Crystalline Form III of Vilanterol Trifenate 1 g of vilanterol trifenatate form II and III is suspended in 5 mL of water and the suspension stirred at a temperature up to 25° C. The crystalline form III is isolated by filtration under reduced pressure, and dried under reduced pressure at a temperature up to 40° C. Yield: 0.72 g (72% w/w).

Example 4: Preparation of Crystalline Form III of Vilanterol Trifenate with Seed 15 g of vilanterol trifenatate form I are suspended in 450 mL of acetone and the suspension heated up to 45° C. The clear solution is stirred for 2 h at a temperature up to 45° C. 90 mL of water is added to the clear solution and left to stir for 2 h at a temperature up to 45° C. The clear solution is slowly cooled down to a temperature of about 5-0° C. and a seed of crystalline form III added. The crystalline form III is isolated by filtration under reduced pressure, and dried under reduced pressure at a temperature up to 50° C. Yield: 11.36 g (76% w/w).

Comparative Example 5: Micronization of Vilanterol Trifenatate Form I

Vilanterol trifenatate form I (15.0 g) was fed to a fluid energy jet mill at 19 g/h, operated with $N_2$ at a pressure of 1 bar for the venturi and a pressure of 1 bar for the ring.

The isolated product isolated presented an XRPD identical to that of the starting material with a particle size distribution of Dv50=4.2 μm; Dv90=9.6 μm.

Example 6: Micronization of Vilanterol Trifenatate Form II

Vilanterol trifenatate form II is fed to a fluid energy jet mill at 10-100 g/h, operated with $N_2$ at a pressure of 1 to 8 bar for the venturi and a pressure of 1 to 8 bar for the ring.

The isolated product presents an XRPD identical to the one of the starting material with a particle size distribution of Dv90 below 10 μm, i.e. comparable to known form I.

Example 7: Micronization of Vilanterol Trifenatate Form III

Vilanterol trifenatate form III is fed to a fluid energy jet mill at 10-100 g/h, operated with $N_2$ at a pressure of 1 to 8 bar for the venturi and a pressure of 1 to 8 bar for the ring.

The isolated product presents an XRPD identical to the one of the starting material with a particle size distribution of Dv90 below 10 μm, i.e. comparable to known form I.

Example 8: Solubilities of Forms II and III of the Invention and Comparative Data for Form I Visual solubility of certain forms (compounds) in differing solvents was assessed according to the procedure described in the *European Pharmacopeia* 6.0 section 5.11. p. 659 (indicated in Table 19).

8.1 Methodology
8.1.1 Dissolving Procedure

The compound was shaken vigorously for 1 min and placed in a constant temperature device for 15 min at 25.0±0.5° C. If the compound was not completely dissolved, the shaking was repeated for 1 min and the tube placed in a constant temperature device for 15 min.

8.1.2 Method 50 mg of compound was weighed in a stoppered tube, 0.05 mL of the solvent added and the Dissolving Procedure (see above) followed. If the compound was completely dissolved, it is very soluble.

If the compound was not completely dissolved, a further 0.45 mL of the solvent was added and the Dissolving Procedure (see above) followed. If the compound was completely dissolved, it is freely soluble.

If the compound was still not completely dissolved, still further 1.0 mL of the solvent was added and the Dissolving Procedure (see above) followed. If the compound was completely dissolved, it is soluble.

If the compound was still not completely dissolved, another 3.5 mL of the solvent was added and the Dissolving Procedure (see above) followed. If the compound was completely dissolved, it is sparingly soluble.

If the compound was still not completely dissolved, the compound is slightly soluble or very slightly soluble. In this case, and the suspension was heated up to the boiling point (max 80° C.) under stirring to verify the solubility at high temperature. The hot solution was afterwards cooled to room temperature to observe whether the compound precipitates. If the compound at room temperature was completely dissolved, it is soluble at high temperature.

TABLE 19

Solubility ranges description

| Descriptive terms | Abbreviation | Parts of solvent needed for 1 part solute | Solubility (mg/mL) |
|---|---|---|---|
| Very soluble | | <1 | >1000 |
| Freely soluble | FS | 1-10 | 100-1000 |
| Soluble | S | 10-30 | 33-100 |
| Sparingly soluble | SS | 30-100 | 10-33 |
| Slightly soluble | VSS | 100-1000 | 1-10 |
| Very slightly soluble | | 1000-10000 | 1-0.1 |
| Insoluble | INS | >10000 | <0.1 |

8.2 Results

Forms I, II and III of vilanterol trifenatate are soluble in methanol at 25° C.

Forms I and III of vilanterol trifenatate are sparingly soluble in ethanol at 25° C.

Form II of vilanterol trifenatate is sparingly soluble in ethanol at 50° C.

Forms I and II of vilanterol trifenatate are freely soluble in tetrahydrofuran (THF) at 25° C.

Form III of vilanterol trifenatate is sparingly soluble in THF at 25° C.

Form I of vilanterol trifenatate is freely soluble in 1,4-dioxane at 25° C.

Form II of vilanterol trifenatate is soluble in 1,4-dioxane at 25° C.

Form III of vilanterol trifenatate is sparingly soluble in 1,4-dioxane at 25° C.

Forms I, II and III of vilanterol trifenatate are insoluble in water at 75° C.

Example 9: Comparison of Hygroscopicity of New Form II with Form I

Hygroscopicity of a sample of each of new form II and comparative form I was determined using the protocol provided below in conditions of 80% RH and 25° C. Both samples of new form II and form I treated under these conditions showed stability after DVS analysis (as provided in the protocol below) in comparison with an untreated sample.

In the case of form I, data recorded by DVS analysis showed a mass increased percentage of 0.19% whereas that for new polymorph II showed an improved massed increased percentage of 0.04%. Therefore, although both forms can be classified as non-hygroscopic, form II shows a difference in hygroscopicity which, under certain conditions of handling or processing, is significant, as discussed hereinabove.

Figure 25:
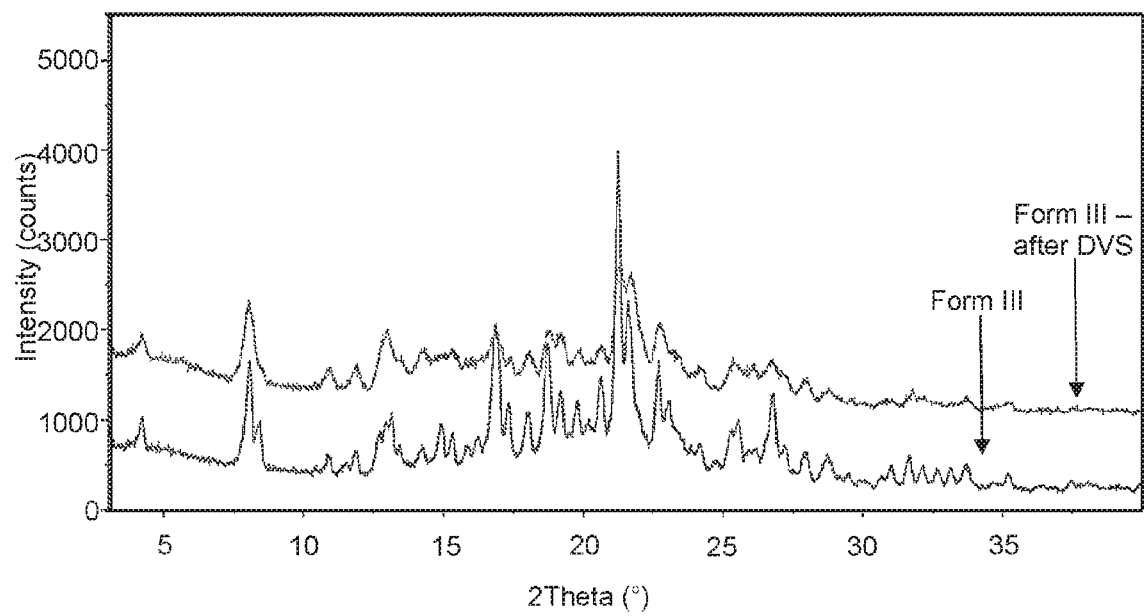
FIG. 25: XRPD diffractogram of new crystalline form III of vilaterol trifenatate after DVS analysis Comparative

Furthermore, after DVS analysis of a sample of form III, the XRPD pattern shows no significant modifications as shown in FIG. 25.

Example 10: Comparison of Storage Stability of New Forms II and III with Form I

Figure 27:
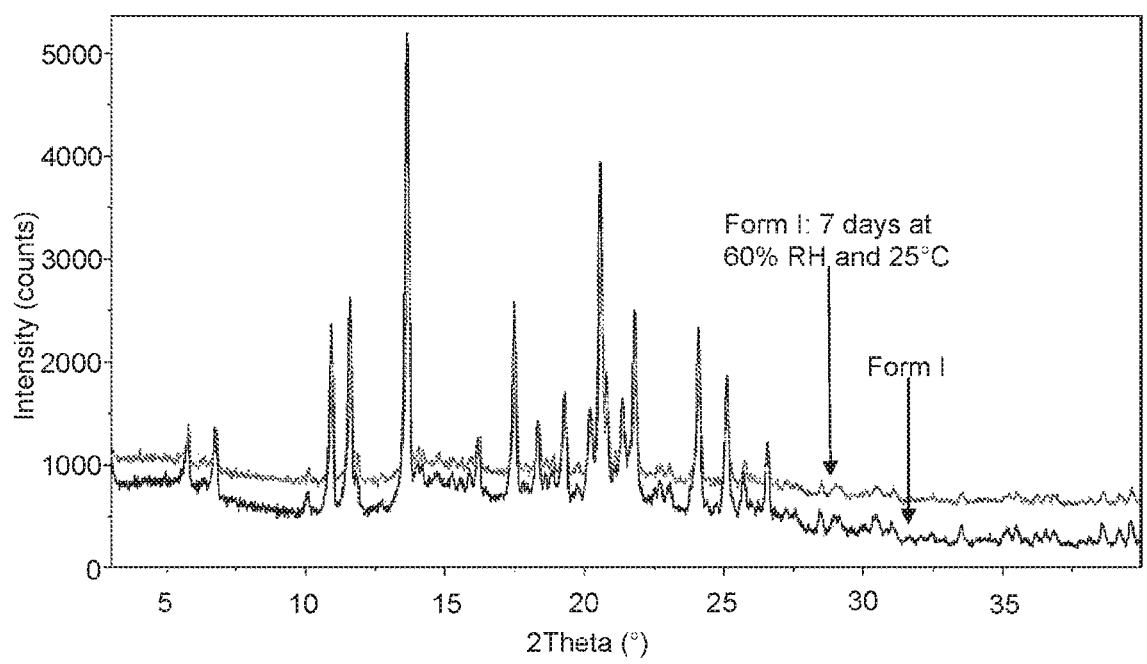
FIG. 27: XRPD diffractogram of form I of vilaterol trifenatate under 60% RH and 25° C. for 7 days.
Figure 26:
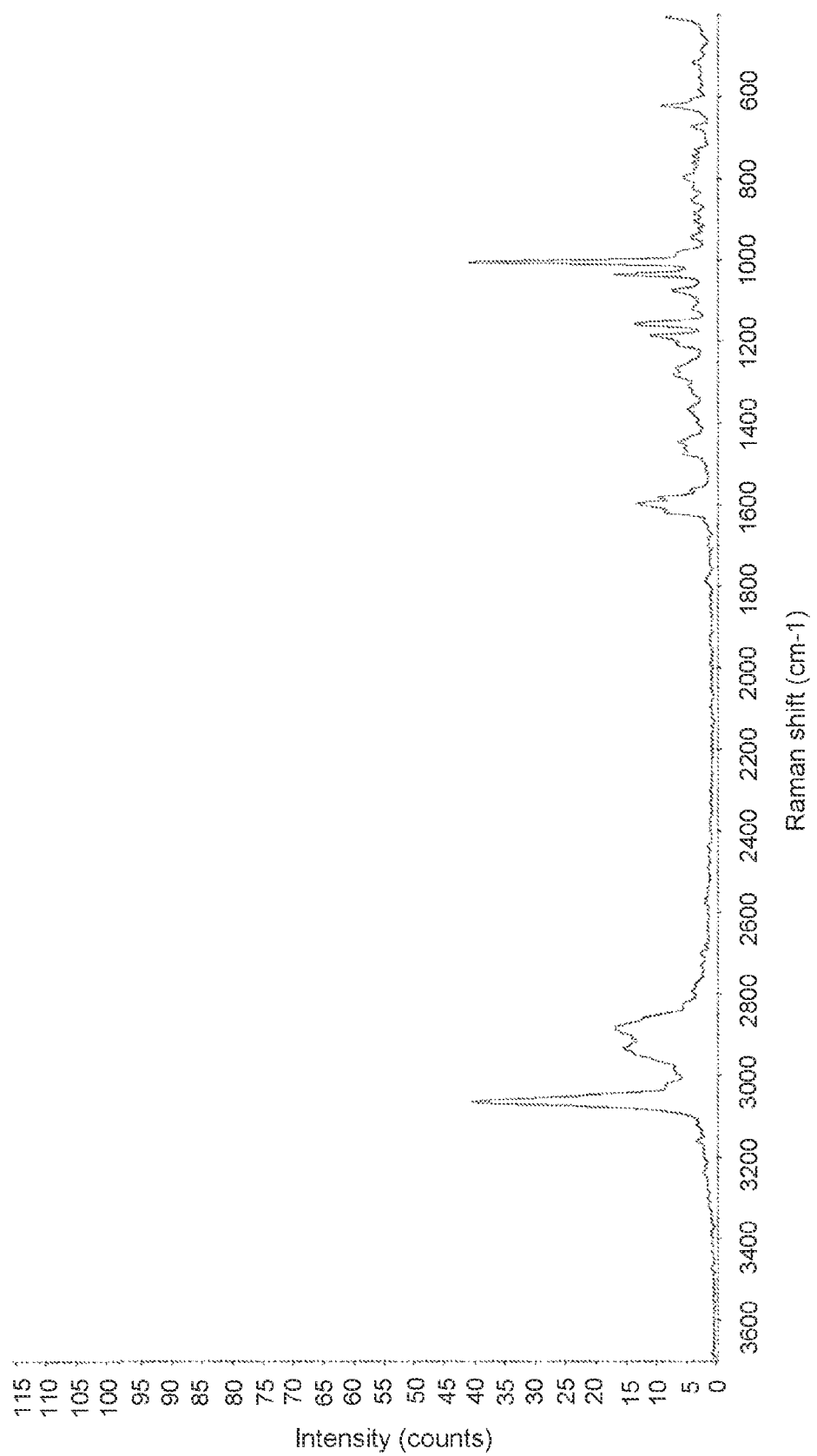
FIG. 26: FT-Raman spectrum of form I of vilaterol trifenatate Comparative

Approximately 30 mg of exposed powder of comparative form 1 and new forms II and III, respectively, were stored at 25'C and 60% RH for seven days. Each powder was then analyzed by XRPD and its diffraction pattern was compared with that of untreated sample. No significant modifications in XRPD pattern were observed, as shown in the FIG. 27 below for form I (comparative) and FIGS. 6 and 10 for novel forms II and III.

Instrument Parameters & General Experimental Protocols
FT-Raman Spectroscopy

Raman spectra were recorded with a Nicolet iS50 FT-IR Spectrometer The excitation source was a Nd-YAG laser (1064 nm) in the backscattering (180°) configuration. The focused laser beam diameter was approx. 50 mm and the spectral resolution 4 cm-1. The spectra were recorded with a laser power at the sample of approx. 100 mW.

HPLC—High Performance Liquid Chromatography

The HPLC analysis was conducted using a waters system under the following conditions:
Column: waters symmetry shield rp18 4.6×150 mm 3.5 micra
Flow rate: 0.8 ml/min
Injection volume: 10 ul
Temperature: 30° c.
Solvents a: $H_2O$ (0.1% tfa)
Solvent b: $CH_3CN$
The gradient elution method as follows:

| Time (min.) | Flow (ml/min.) | Mobile phase a (%) | Mobile phase b (%) |
|---|---|---|---|
| 0.01 | 0.80 | 85.0 | 15.0 |
| 0.10 | 0.80 | 85.0 | 15.0 |
| 36.00 | 0.80 | 20.0 | 80.0 |
| 42.00 | 0.80 | 20.0 | 80.0 |
| 42.10 | 0.80 | 85.0 | 15.0 |
| 50.00 | 0.80 | 85.0 | 15.0 |

XRPD—X-Ray Powder Diffraction

The X-ray powder patterns were recorded using the PANalytical X'Pert PRO X-ray diffraction system equipped with a PW3373/00 Cu LFF DK184511 X-Ray tube and a X'Celerator RTMS (Real Time Multiple Strip) detector under the following conditions:

| Measurement details | |
|---|---|
| Measurement type: | Single Scan |
| Sample mode | Reflection |
| Voltage (kV): | 40 |
| Current (mA): | 40 |
| Sample Movement mode | Spinning |
| Rotation time (s): | 1.0 |
| Scan | |
| Scan axis: | Gonio |
| Scan mode: | Continuous |
| Scan range: | 3.0010-39.9997 |
| Step size (°): | 0.0167 |
| Counting time (s): | 12.700 |
| N° of points: | 2214 |
| Used wavelength | |
| Intended wavelength type: | Kα1 |
| Kα1 (A): | 1,540598 |
| Kα2 (A): | 1,544426 |
| Kα2/Kα1 intensity ratio: | 0,50 |
| Kα (A): | 1,541874 |
| Kα (A): | 1,392250 |
| Incident beam path | |
| Radius (mm): | 240.0 |
| Soller slit | 0.04 rad |
| Mask | 15 mm |
| Divergent slit | 1/4° |
| Anti-scatter slit | 1/2° |
| Diffracted beam path | |
| Anti-scatter slit | 5.0 mm |
| Filter | Nickel |
| Soller slit | 0.04 rad |
| Detector | X'Celerator |
| Mode | Scanning |
| Active length (2Theta) | 2.122° |

DSC—Differential Scanning Calorimetry

The analysis was carried out using a DSC Q200 TA instruments equipped with a refrigerator cooling system (RCS40) and autosampler.

The sample was weighed in an aluminum hermetic pan with pinhole. The analysis was performed heating the sample from 25° C. to 350° C. at 10° C./min.

TGA—Thermal Gravimetric Analysis

The analysis was carried out using the Mettler Toledo TGA/DSC1.

The sample was weighed in an aluminum pan hermetically sealed with an aluminum pierced cover. The analysis was performed heating the sample from 25° C. to 320° C. at 10° C./min. TGA-FTIR coupled with Thermo Nicoled is 10 spectometer.

TGA-EGA ThermoGravimetric Analysis-Evolution Gas Analysis

The analysis was carried out using the mettler toledo TGA/DSC1. The sample was weighed in an aluminum pan hermetically sealed with an aluminum pierced cover. The analysis was performed heating the sample from 25° C. to 320° C. at 10° C./min. The evolved gas is compared with ft-ir spectra database for identification.

DVS—Dynamic Vapor Sorption

The sample was subjected to DVS measuring using SMS-DVS intrinsic. The kinetic moisture sorption measurement was performed at 25° C. and in a RH % range described in the following:
From 40% RH to 90% RH
Form 90% RH to 0% RH
From 0% RH to 90% RH
From 90% RH to 0% RH
The sample was analyzed by XRPD after the analysis.

Hygroscopicity

The hygroscopicity of the sample was determined using the method reported in the academic article "Efficient throughput method for hygroscopicity classification of an active and inactive pharmaceutical ingredients by water vapor sorption analysis" V. Murikipudi et al., Pharmaceutical Development and Technology, 2013, 18(2): 348-358.

The hygroscopicity was calculated using the following equation:

% Weight Change=[(W2−W1)/W1]*100

W1: weight of sample at the start of the experiment (25° C. and 40% RH)
W2: weight of sample at 25° C. and 80% RH in the first absorption cycle

| EP 7.0 CLASSIFICATION | CRITERIA |
|---|---|
| Non hygroscopic | Increase in mass is less than 0.2% |
| Slightly hygroscopic | Increase in mass is less than 2% and equal to or greater than 0.2% |
| Hygroscopic | Increase in mass is less than 15% and equal to or greater than 2% |
| Very Hygroscopic | Increase in mass is equal to or greater than 15% |
| Deliquescent | Sufficient water is absorbed to form a liquid |

SUMMARY

Therefore, herein has been described, inter alia:
A. A crystalline form II of vilanterol trifenatate characterized by a x-ray powder diffraction pattern as depicted in FIG. 1 and comprising the diffraction angles (2Theta) as listed in table 1.
B. Crystalline form II of vilanterol trifenatate according to claim 1 further characterized by DSC profile having an endothermic event with onset at 64° C. and peak at 72° C. and a degradation event with onset at 189° C. and peak at 191° C.
C. Crystalline form II of vilanterol trifenatate according to A or B further characterized by TGA profile having a weight loss of 1.13%.
D. Crystalline form II of vilanterol trifenatate according to any one of A to C further characterized by a vilanterol trifenatate:water ratio of 1:0.57.
E. Crystalline form II of vilanterol trifenatate according to any one of A to D further characterized by $^{13}$C CP-DD/MAS-TOSS and $^{13}$C CP-DD/MAS-TOSS with Dipolar Dephasing comprising the characteristic chemical shift (±0.218 ppm): 182.35, 171.24, 169.06, 154.47, 152.51, 146.19, 143.36, 36.17, 134.43, 133.12, 130.50, 127.67, 126.15, 124.62.
F. Crystalline form II of vilanterol trifenatate according to any one of the claims A to E further characterized by $^{15}$N CP-DD/MAS as depicted in FIG. 5.
G. Crystalline form II of vilanterol trifenatate according to any one of A to F further characterized as not hygroscopic.
H. A crystalline form III of vilanterol trifenatate characterized by a x-ray powder diffraction pattern as depicted in FIG. 7 and comprising the diffraction angles (2Theta) as listed in table 3.
I. Crystalline form III of vilanterol trifenatate according to claim 8 further characterized by DSC profile having a endothermic event with onset at 67° C. and peak at 79° C. and a degradation event with onset at 189° C. and peak at 191° C.
J. Crystalline form III of vilanterol trifenatate according to H or I further characterized by TGA profile having a two consecutive poor weight loss of approx. 0.32% and 0.54%.
K. Crystalline form III of vilanterol trifenatate according to any one of H to J further characterized by an ratio vilanterol trifenatate:water 1:0.37.
L. Crystalline form III of vilanterol trifenatate according to any one of H to K further characterized as slightly hygroscopic.
M. Crystalline form IV of vilanterol trifenatate characterized by a x-ray powder diffraction pattern as depicted in FIG. 11 and comprising the following characteristic diffraction angles (2Theta) as listed in table 5.
N. Crystalline form V of vilanterol trifenatate characterized by a x-ray powder diffraction pattern as depicted in FIG. 12 and comprising the following characteristic diffraction angles (2Theta) as listed in table 6.
O. Crystalline form VI of vilanterol trifenatate characterized by a x-ray powder diffraction pattern as depicted in FIG. 13 and comprising the following characteristic diffraction angles (2Theta) as listed in table 7.
P. Crystalline form VII of vilanterol trifenatate characterized by a x-ray powder diffraction pattern as depicted in FIG. 14 and comprising the following characteristic diffraction angles (2Theta) as listed in table 8.
Q. Crystalline form VIII of vilanterol trifenatate characterized by a x-ray powder diffraction pattern as depicted in FIG. 15 and comprising the following characteristic diffraction angles (2Theta) as listed in table 9.
R. Crystalline form IX of vilanterol trifenatate characterized by a x-ray powder diffraction pattern as depicted in FIG. 16 and comprising the following characteristic diffraction angles (2Theta) as listed in table 10.
S. Crystalline form X of vilanterol trifenatate characterized by a x-ray powder diffraction pattern as depicted in FIG. 17 and comprising the following characteristic diffraction angles (2Theta) as listed in table 11.
T. Crystalline form XI of vilanterol trifenatate characterized by a x-ray powder diffraction pattern as depicted in FIG. 18 and comprising the following characteristic diffraction angles (2Theta) as listed in table 12.
U. Crystalline form XII of vilanterol trifenatate characterized by a x-ray powder diffraction pattern as depicted in FIG. 19 and comprising the following characteristic diffraction angles (2Theta) as listed in table 13.
V. Crystalline form XIII of vilanterol trifenatate characterized by a x-ray powder diffraction pattern as depicted in FIG. 20 and comprising the following characteristic diffraction angles (2Theta) as listed in table 14.
W. Crystalline form XIV of vilanterol trifenatate characterized by a x-ray powder diffraction pattern as depicted in FIG. 21 and comprising the following characteristic diffraction angles (2Theta) as listed in table 15.
X. A process for the preparation of new crystalline form II of vilanterol trifenatate according to any one of A to G comprising the steps of:
  a1) suspending vilanterol trifenatate in acetone, preferably in 30 vol.,
  a2) heating the suspension, preferably up to 50° C. and preferably stirred,
  a3) add water, preferably 3 vol. to the clear solution and preferably stirred,
  a4) cooling down the obtained solution, preferably to 5-0° C., preferably at a rate about 10° C./hour and,
  a5) optionally, add seed of crystalline form II, and
  a6) isolating new crystalline form II, preferably by filtration, preferably under reduced pressure, followed by drying or optionally by spray drying the suspension.
Y. A process for the preparation of new crystalline form III of vilanterol trifenatate according to any one of the claims H to L comprising the steps of:
  b1) suspending vilanterol trifenatate form II and III in water preferably in 5 vol., preferably at 20-25° C. and preferably stir,
  b2) isolating new crystalline form III, preferably by filtration, preferably under reduced pressure followed by drying or optionally by spray drying the suspension.
Z. A process for the preparation of new crystalline form III of vilanterol trifenatate according to any one of the claims H to L comprising the steps of:
  c1) suspending vilanterol trifenatate in acetone, preferably in 30 vol.,
  c2) heating the suspension, preferably up to 50° C.,
  c3) add water, preferably 6 vol., to the obtained solution,
  c4) cooling down the obtained solution, preferably to 5-0° C., preferably at a rate about 10° C./hour and,
  c5) optionally, add seed of crystalline form III, and
  c6) isolating new crystalline form III, preferably by filtration preferably under reduced pressure, followed by drying or optionally by spray drying the suspension.
AA. Vilanterol trifenatate according to any one of A to L and BB to DD containing less than 0.15%, preferably less than 0.10% in area by HPLC of impurity A.
BB. A process for the preparation of new crystalline form III of vilanterol trifenatate according to any one of H to L comprising the steps of:
  d1) suspending vilanterol trifenatate form II in heptane, preferably in 24 vol.,
  d2) heating the suspension preferably up to 50° C., preferably at a rate about 20° C./hour and preferably stir,
  d3) cooling down the suspension preferably to 10° C., preferably at a rate about 20° C./hour and preferably stir,
  d4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir,
  d5) heating the suspension preferably up to 25° C., preferably at a rate about 10° C./hour and preferably stir,
  d6) isolating new crystalline form III, preferably by filtration preferably under reduced pressure and optionally followed by drying or optionally by spray drying the suspension.

CC. A process for the preparation of new crystalline form IV of vilanterol trifenatate according to M comprising steps of:
- e1) suspending vilanterol trifenatate form II in cyclohexane, preferably in 24 vol.,
- e2) heating the suspension preferably up to 50° C., preferably at a rate about 20° C./hour and preferably stir,
- e3) cooling down the suspension preferably to 10° C., preferably at a rate about 20° C./hour and preferably stir,
- e4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir,
- e5) heating the suspension preferably up to 25° C., preferably at a rate about 10° C./hour and preferably stir,
- e6) isolating new crystalline form IV, preferably by filtration preferably under reduced pressure and optionally followed by drying or optionally by spray drying the suspension.

DD. A process for the preparation of new crystalline form V of vilanterol trifenatate according to N comprising steps of:
- f1) suspending vilanterol trifenatate form II in methylcyclohexane, preferably in 24 vol.,
- f2) heating the suspension preferably up to 50° C., preferably at a rate about 20° C./hour and preferably stir,
- f3) cooling down the suspension preferably to 10° C., preferably at a rate about 20° C./hour and preferably stir,
- f4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir,
- f5) heating the suspension preferably up to 25° C., preferably at a rate about 10° C./hour and preferably stir,
- f6) isolating new crystalline form V, preferably by filtration preferably under reduced pressure and optionally followed by drying or optionally by spray drying the suspension.

EE. A process for the preparation of new crystalline form VI of vilanterol trifenatate according to 0 comprising steps of:
- g1) suspending vilanterol trifenatate form II in 2-propanol, preferably in 24 vol.,
- g2) heating the suspension preferably up to 50° C., preferably at a rate about 20° C./hour and preferably stir,
- g3) cooling down the suspension preferably to 10° C., preferably at a rate about 20° C./hour and preferably stir,
- g4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir,
- g5) heating the suspension preferably up to 25° C., preferably at a rate about 10° C./hour and preferably stir,
- g6) isolating new crystalline form VI, preferably by filtration preferably under reduced pressure and optionally followed by drying or optionally by spray drying the suspension.

FF. A process for the preparation of new crystalline form VII of vilanterol trifenatate according to P comprising steps of:
- h1) suspending vilanterol trifenatate form II in 3-methyl-1-butanol, preferably in 24 vol.,
- h2) heating the suspension preferably up to 50° C., preferably at a rate about 20° C./hour and preferably stir,
- h3) cooling down the suspension preferably to 10° C., preferably at a rate about 20° C./hour and preferably stir,
- h4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir,
- h5) heating the suspension preferably up to 25° C., preferably at a rate about 10° C./hour and preferably stir,
- h6) isolating new crystalline form VII, preferably by filtration preferably under reduced pressure and optionally followed by drying or optionally by spray drying the suspension.

GG. A process for the preparation of new crystalline form VIII of vilanterol trifenatate according to Q comprising steps of:
- i1) suspending vilanterol trifenatate form II in anisole, preferably in 24 vol.,
- i2) heating the suspension preferably up to 50° C., preferably at a rate about 20° C./hour and preferably stir,
- i3) cooling down the suspension preferably to 10° C., preferably at a rate about 20° C./hour and preferably stir,
- i4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir,
- i5) heating the suspension preferably up to 25° C., preferably at a rate about 10° C./hour and preferably stir, i6) isolating new crystalline form VIII, preferably by filtration preferably under reduced pressure and optionally followed by drying or optionally by spray drying the suspension.

HH. A process for the preparation of new crystalline form IX of vilanterol trifenatate according to R comprising steps of:
- j1) suspending vilanterol trifenatate form II in nitromethane, preferably in 24 vol.,
- j2) heating the suspension preferably up to 50° C., preferably at a rate about 20° C./hour and preferably stir,
- j3) cooling down the suspension preferably to 10° C., preferably at a rate about 20° C./hour and preferably stir,
- j4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir,
- j5) heating the suspension preferably up to 25° C., preferably at a rate about 10° C./hour and preferably stir,
- j6) isolating new crystalline form IX, preferably by filtration preferably under reduced pressure and optionally followed by drying or optionally by spray drying the suspension.

II. A process for the preparation of new crystalline form X of vilanterol trifenatate according to S comprising steps of:
- k1) suspending vilanterol trifenatate form I in binary mixture, preferably 50:50 of cyclohexane:ethanol or heptane:ethanol, preferably in 24 vol.
- k2) heating the suspension preferably up to 50° C., preferably at a rate about 20° C./hour and preferably stir,
- k3) cooling down the suspension preferably to 10° C., preferably at a rate about 20° C./hour and preferably stir,
- k4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir,
- k5) heating the suspension preferably up to 25° C., preferably at a rate about 10° C./hour and preferably stir,
- k6) isolating new crystalline form X, preferably by filtration preferably under reduced pressure and optionally followed by drying or optionally by spray drying the suspension.

JJ. A process for the preparation of new crystalline form X of vilanterol trifenatate according to S comprising steps of:
- l1) suspending vilanterol trifenatate form II in a binary mixture, preferably 50:50 of cyclohexane:ethanol or heptane:ethanol, preferably in 24 vol.,
- l2) heating the suspension preferably up to 50° C., preferably at a rate about 20° C./hour and preferably stir,
- l3) cooling down the suspension preferably to 10° C., preferably at a rate about 20° C./hour and preferably stir,
- l4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir,
- l5) heating the suspension preferably up to 25° C., preferably at a rate about 10° C./hour and preferably stir,
- l6) isolating new crystalline form X, preferably by filtration preferably under reduced pressure and optionally followed by drying or optionally by spray drying the suspension.

KK. A process for the preparation of new crystalline form XI of vilanterol trifenatate according to T comprising steps of:
- m1) suspending vilanterol trifenatate form II in binary mixture, preferably 50:50 of cyclohexane:2-methyltetrahydrofuran, preferably in 24 vol.,
- m2) heating the suspension preferably up to 50° C., preferably at a rate about 20° C./hour and preferably stir,
- m3) cooling down the suspension preferably to 10° C., preferably at a rate about 20° C./hour and preferably stir,
- m4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir,
- m5) heating the suspension preferably up to 25° C., preferably at a rate about 10° C./hour and preferably stir,
- m6) isolating new crystalline form XI, preferably by filtration preferably under reduced pressure and optionally followed by drying or optionally by spray drying the suspension.

LL. A process for the preparation of new crystalline form XII of vilanterol trifenatate according to U comprising steps of:
- n1) suspending vilanterol trifenatate form II in a binary mixture, preferably 50:50 of heptane: 1,2-dimethoxyethane, preferably in 24 vol.,
- n2) heating the suspension preferably up to 50° C., preferably at a rate about 20° C./hour and preferably stir,
- n3) cooling down the suspension preferably to 10° C., preferably at a rate about 20° C./hour and preferably stir,
- n4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir, n5) heating the suspension preferably up to 25° C., preferably at a rate about 10° C./hour and preferably stir, n6) isolating new crystalline form XII, preferably by filtration preferably under reduced pressure and optionally followed by drying or optionally by spray drying the suspension.

MM. A process for the preparation of new crystalline form XIII of vilanterol trifenatate according to V comprising steps of:

o1) suspending vilanterol trifenatate form II in a binary mixture, preferably 50:50 of cyclohexane:methylethylketone or heptane:methylethylketone or mesitylene:methylethylketone, preferably in 24 vol., o2) heating the suspension preferably up to 50° C., preferably at a rate about 20° C./hour and preferably stir, o3) cooling down the suspension preferably to 10° C., preferably at a rate about 20° C./hour and preferably stir, o4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir, o5) heating the suspension preferably up to 25° C., preferably at a rate about 10° C./hour and preferably stir, o6) isolating new crystalline form XIII, preferably by filtration preferably under reduced pressure and optionally followed by drying or optionally by spray drying the suspension.

NN. A process for the preparation of new crystalline form XIV of vilanterol trifenatate according to W comprising steps of:

p1) suspending vilanterol trifenatate form III in methylcyclohexane, preferably in 24 vol., p2) heating the suspension preferably up to 50° C., preferably at a rate about 20° C./hour and preferably stir, p3) cooling down the suspension preferably to 10° C., preferably at a rate about 20° C./hour and preferably stir, p4) optionally, heating the suspension preferably up to 50° C., preferably at a rate about 10° C./hour and preferably stir, cooling down the suspension preferably to 10° C., preferably at a rate about 10° C./hour and preferably stir, heating the suspension preferably up to 50° C., preferably at a rate about 5° C./hour and preferably stir, cooling down the suspension preferably to 10° C., preferably at a rate about 5° C./hour and preferably stir, p5) heating the suspension preferably up to 25° C., preferably at a rate about 10° C./hour and preferably stir, p6) isolating new crystalline form XIV, preferably by filtration preferably under reduced pressure and optionally followed by drying or optionally by spray drying the suspension.

OO. A process for the preparation of amorphous of vilanterol trifenatate according to any one of X to AA comprising steps of:

r1) dissolving vilanterol trifenatate in methanol, preferably in 38 vol., preferably at 25° C., r2) preferably stir the solution at preferably 25° C. and, r3) isolating new amorphous form, preferably by spray drying.

PP. A process according to any of Y to OO, wherein the process further comprises the vilanterol trifenatate particle size control during crystallization.

QQ. A process according to any of Y to PP, wherein the product is isolated and dried by conventional drying technologies, such as oven drying and/or lyophilization and/or spray drying.

RR. A process according to QQ, wherein the process further comprises the micronizing the vilanterol trifenatate.

SS. A process according to RR, wherein the micronization is effected by cavitation and/or particle to particle collision and/or shear stress in the milling apparatus.

TT. A process according to SS, further comprising the step of isolating vilanterol trifenatate in the form of powder, optionally by spray drying.

UU. Vilanterol trifenatate obtainable from a process according to claim Y to TT.

VV. Vilanterol trifenatate according to claim 52, wherein the vilanterol trifenatate is suitable for administration by inhalation with a particle size distribution of Dv90 below 10 μm, optionally Dv90 below 5 μm.

WW. A pharmaceutical formulation for administration by inhalation comprising any one of the crystalline forms of vilanterol trifenatate of this invention and one or more pharmaceutically acceptable excipients therefor.

XX. A pharmaceutical application using any one of the crystalline forms of vilanterol trifenatate claimed in this invention or forms derived therefrom.

YY. Any crystalline form of vilanterol trifenatate obtained according to any one of the above paragraphs.

The invention claimed is:

1. A crystalline form of vilanterol trifenatate, characterised by an XRPD pattern as depicted in any one of the figures and comprising the diffraction angles (2 θ) as listed in the table:

| Angle 2θ (°) | | | | | | |
| --- | --- | --- | --- | --- | --- | --- |
| Form II | Form III | Form IV | Form V | Form VI | Form VII | Form VIII |
| — | — | 3.87 | 3.82 | — | — | — |
| 4.31 | 4.22 | — | — | — | — | — |
| — | — | — | — | — | — | 5.42 |
| — | — | — | — | 5.70 | — | — |
| — | — | — | — | — | — | 5.81 |
| — | — | — | — | 6.03 | 6.02 | — |
| — | — | — | — | — | — | — |
| — | — | — | — | — | — | — |
| — | — | — | — | — | 6.94 | — |
| — | — | — | — | — | — | 7.03 |
| — | — | — | — | — | — | — |
| — | — | 7.70 | 7.70 | — | 7.71 | — |
| 8.14 | 8.12 | 8.11 | 8.10 | — | — | — |
| 8.43 | 8.44 | — | — | — | — | — |
| — | — | — | — | — | — | — |
| — | — | — | 8.72 | — | — | — |
| — | — | — | — | — | — | 8.89 |
| — | — | — | — | — | 9.26 | 9.29 |

Angle 2θ (°)

| | | | | | | |
|---|---|---|---|---|---|---|
| — | — | — | — | — | — | — |
| — | — | 9.63 | 9.63 | 9.60 | — | — |
| — | — | — | — | — | — | 9.80 |
| 10.59 | — | — | — | — | — | — |
| — | — | — | — | — | 10.71 | 10.74 |
| — | 10.91 | — | — | — | — | — |
| 11.09 | — | — | — | — | 11.15 | 11.01 |
| — | — | — | — | 11.47 | — | — |
| — | 11.52 | 11.60 | 11.59 | — | — | — |
| — | 11.89 | — | — | — | 11.84 | 11.82 |
| — | — | — | — | 11.95 | — | 12.03 |
| — | — | 12.32 | 12.31 | — | — | — |
| — | — | — | — | — | — | 12.48 |
| — | — | 12.62 | 12.59 | — | — | — |
| — | 12.69 | — | — | — | — | — |
| 12.85 | — | — | — | 12.80 | 12.80 | — |
| — | 12.92 | — | — | — | — | — |
| 13.10 | 13.16 | — | — | — | — | — |
| 13.48 | 13.44 | 13.43 | 13.35 | — | — | — |
| — | — | — | — | 13.62 | — | — |
| 13.81 | — | 13.83 | — | — | — | — |
| — | — | — | 14.00 | 14.06 | 14.01 | 13.92 |
| 14.26 | 14.24 | — | — | — | — | 14.25 |
| 14.72 | — | — | — | — | 14.77 | — |
| — | — | — | — | 14.92 | — | — |
| — | 14.99 | — | — | — | — | — |
| — | 15.36 | — | — | — | — | — |
| — | — | 15.54 | 15.51 | — | 15.44 | — |
| — | 15.86 | — | — | — | — | — |
| 16.09 | 16.25 | — | 16.11 | 16.20 | 16.23 | 16.09 |
| — | — | — | 16.47 | — | — | — |
| 16.62 | — | — | — | — | — | 16.63 |
| — | 16.79 | — | — | — | — | — |
| — | 16.98 | 17.03 | 16.93 | — | — | 16.92 |
| 17.12 | 17.32 | — | 17.22 | — | — | — |
| 17.51 | — | 17.41 | 17.42 | — | 17.46 | — |
| — | — | — | — | 17.55 | — | 17.56 |
| — | — | — | — | 17.98 | — | — |
| — | 18.07 | — | — | — | — | 18.14 |
| — | — | — | — | — | — | 18.35 |
| — | — | — | — | 18.48 | — | — |
| — | — | — | — | — | 18.60 | — |
| — | 18.75 | — | — | — | — | 18.75 |
| 19.01 | — | 19.02 | 19.02 | — | — | 18.91 |
| 19.22 | 19.17 | — | — | — | 19.11 | — |
| — | — | — | 19.35 | — | — | 19.28 |
| 19.62 | — | 19.45 | 19.56 | — | — | — |
| — | 19.75 | 19.70 | 19.78 | — | — | 19.66 |
| 20.04 | — | — | — | 20.04 | — | — |
| 20.34 | 20.18 | — | 20.33 | — | 20.24 | — |
| — | 20.57 | 20.59 | — | 20.63 | 20.69 | 20.63 |
| — | 20.71 | 20.85 | — | — | — | 20.84 |
| — | — | — | 21.00 | 21.05 | — | — |
| 21.15 | 21.26 | 21.17 | 21.35 | — | 21.17 | 21.27 |
| 21.44 | 21.59 | — | — | 21.49 | — | — |
| 21.69 | 21.70 | — | — | — | 21.66 | — |
| 21.93 | — | 21.93 | 21.93 | — | — | 21.79 |
| — | — | — | — | 22.07 | — | 22.07 |
| 22.42 | — | 22.47 | — | 22.44 | — | 22.31 |
| — | 22.60 | — | 22.53 | — | — | — |
| — | 22.69 | — | — | — | 22.76 | 22.81 |
| 23.01 | 23.07 | 23.04 | 23.02 | 23.01 | — | — |
| — | — | — | 23.17 | — | — | — |
| 23.39 | — | — | 23.37 | — | — | 23.28 |
| — | — | 23.49 | 23.53 | 23.61 | 23.64 | 23.67 |
| 23.98 | — | — | 23.75 | — | — | 23.91 |
| — | 24.17 | 24.08 | — | — | — | 24.09 |

Angle 2θ (°)

| | | | | | | |
|---|---|---|---|---|---|---|
| — | — | — | — | 24.23 | — | — |
| 24.32 | — | 24.31 | 24.34 | — | — | — |
| 25.47 | — | — | — | — | 24.65 | — |
| — | 24.70 | 24.86 | 24.82 | 24.71 | — | 24.90 |
| — | 25.28 | 25.33 | — | — | — | 25.28 |
| — | 25.55 | — | 25.51 | 25.43 | — | — |
| 25.75 | — | — | — | — | 25.67 | 25.64 |
| — | — | 25.97 | 25.94 | — | — | 25.93 |
| — | — | — | — | 26.08 | 26.06 | — |
| 26.14 | 26.15 | — | — | — | — | — |
| — | — | — | 26.41 | — | — | — |
| — | — | 26.50 | — | — | — | — |
| 26.72 | — | 26.74 | 26.62 | — | 26.73 | — |
| — | 26.82 | — | 26.95 | 26.91 | — | 26.95 |
| — | — | 27.02 | — | — | — | — |
| 27.18 | — | — | — | — | 27.18 | — |
| — | 27.26 | 27.28 | — | — | — | — |
| — | — | — | 27.39 | — | — | — |
| — | — | — | — | 27.61 | — | — |
| 27.69 | — | — | — | — | — | 27.73 |
| — | 27.95 | — | — | — | — | — |
| — | — | 28.06 | — | — | — | — |
| — | — | — | 28.23 | — | — | — |
| — | — | 28.42 | — | — | — | 28.43 |
| 28.78 | 28.72 | 28.70 | 28.67 | 28.79 | — | 28.79 |
| — | — | — | — | — | 28.96 | — |
| — | — | — | — | 29.13 | — | — |
| — | — | — | — | — | — | 29.27 |
| — | — | 29.33 | 29.30 | — | — | — |
| 29.61 | 29.49 | — | — | — | 29.54 | — |
| 29.70 | — | — | — | — | 29.76 | 29.74 |
| — | 29.95 | — | — | — | — | — |
| — | — | 30.32 | 30.25 | — | 30.19 | — |
| — | — | — | — | — | — | 30.43 |
| — | 30.62 | — | 30.68 | — | — | — |
| 30.84 | — | 30.82 | — | — | — | — |
| — | 31.00 | — | — | — | — | 31.06 |
| — | — | 31.24 | — | — | — | — |
| — | — | — | 31.46 | 31.51 | — | 31.55 |
| 31.61 | 31.68 | — | — | — | — | — |
| 32.07 | — | — | 31.83 | 31.83 | — | — |
| — | 32.15 | 32.17 | 32.13 | — | — | 32.20 |
| 32.39 | — | — | — | 32.30 | — | — |
| — | 32.65 | — | — | — | — | — |
| — | — | — | 32.83 | — | — | — |
| — | 33.11 | 33.13 | — | — | — | 33.22 |
| — | — | 33.67 | — | — | — | — |
| — | 33.78 | — | 33.83 | — | — | — |
| 33.91 | — | — | — | — | — | — |
| — | — | — | 34.17 | — | — | 34.15 |
| — | — | 34.24 | — | — | — | — |
| 34.46 | — | — | — | — | — | — |
| — | 34.63 | 34.66 | 34.60 | — | — | — |
| — | — | — | — | — | — | 34.81 |
| 34.98 | — | — | 34.99 | — | — | — |
| — | 35.16 | — | — | — | — | — |
| 35.41 | — | 35.40 | — | 35.43 | — | 35.41 |
| — | — | — | — | — | 35.61 | — |
| — | — | — | — | 36.04 | — | — |
| — | 36.37 | — | — | — | — | 36.39 |
| 36.45 | — | — | — | — | — | — |
| — | — | — | 36.62 | 36.72 | — | 36.79 |
| 37.11 | — | — | — | — | — | — |
| — | — | 37.23 | — | — | — | 37.31 |
| — | 37.42 | — | — | 37.40 | — | — |
| — | — | — | — | 37.66 | — | 37.76 |

| Angle 2θ (°) | | | | | | |
|---|---|---|---|---|---|---|
| — | 38.11 | — | 38.14 | — | — | — |
| — | — | 38.28 | — | — | — | — |
| 38.35 | — | — | — | — | — | — |
| — | — | 38.68 | 38.67 | — | — | — |
| — | — | 38.81 | — | — | — | 38.71 |
| 39.29 | — | — | — | — | — | 39.12 |
| — | — | 39.36 | — | — | — | — |
| — | — | — | 39.48 | — | 39.46 | — |
| — | — | — | — | — | — | 39.65 |
| XRPD in FIG. 1 | 7 | 11 | 12 | 13 | 14 | 15 |

| Form IX | Form X | Form XI | Form XII | Form XIII | Form XIV |
|---|---|---|---|---|---|
| — | 5.35 | — | — | — | — |
| — | — | — | 5.61 | — | — |
| — | 5.81 | — | — | — | — |
| 6.01 | — | 6.10 | 6.01 | — | — |
| — | — | — | — | 6.27 | — |
| — | 6.34 | — | — | — | — |
| — | — | — | 6.89 | — | — |
| 7.04 | — | 7.10 | — | 7.05 | — |
| — | 7.25 | — | — | — | — |
| — | 7.48 | — | — | — | 7.51 |
| 8.09 | — | — | — | — | 7.96 |
| — | 8.36 | — | — | — | — |
| — | — | 8.69 | — | — | 8.64 |
| 9.26 | — | — | — | — | — |
| — | — | 9.40 | 9.44 | — | — |
| — | 9.52 | — | — | — | — |
| — | — | — | — | 9.76 | — |
| — | — | — | — | — | 9.61 |
| 10.49 | — | — | — | — | — |
| — | — | — | 10.77 | — | — |
| 10.81 | 10.85 | — | — | — | — |
| 10.92 | — | 10.93 | — | — | 10.87 |
| — | — | — | — | 11.09 | — |
| 11.23 | — | 11.36 | 11.30 | — | 11.37 |
| — | 11.48 | — | — | — | — |
| — | — | — | 11.69 | 11.66 | — |
| 11.71 | 11.77 | — | — | — | — |
| 11.84 | — | 11.82 | — | 11.87 | — |
| — | — | 12.15 | 12.11 | — | — |
| — | 12.37 | — | — | 12.29 | — |
| — | — | 12.50 | 12.56 | — | 12.56 |
| — | — | — | — | 12.96 | — |
| 13.18 | 13.20 | 13.12 | — | — | 13.28 |
| — | — | — | — | 13.40 | — |
| — | 13.68 | — | — | — | — |
| — | — | — | 13.84 | — | 13.86 |
| 14.09 | 14.10 | 14.09 | — | 14.00 | — |
| — | — | — | 14.36 | — | — |
| 14.57 | — | — | — | 14.50 | — |
| — | 14.75 | 14.73 | — | — | — |
| — | — | 14.86 | 14.86 | — | — |
| 15.06 | — | — | — | — | — |
| — | — | — | — | 15.16 | 15.25 |
| 15.99 | 15.68 | — | — | — | 15.91 |
| — | — | 16.17 | 16.22 | — | — |
| 16.31 | — | — | — | — | — |
| — | — | — | 16.59 | — | — |
| — | — | — | — | 16.78 | — |
| 16.86 | 16.88 | 17.02 | 17.01 | — | — |
| — | — | — | — | 17.17 | — |
| 17.34 | 17.36 | — | 17.36 | 17.44 | 17.48 |
| 17.71 | — | 17.70 | 17.64 | — | — |
| — | 17.91 | — | — | — | — |
| 18.07 | — | — | — | — | — |
| — | — | — | 18.31 | — | — |
| — | — | — | — | 18.40 | — |
| 18.55 | 18.61 | 18.52 | 18.56 | 18.60 | 18.52 |
| 18.77 | — | — | 18.80 | — | — |
| — | 18.98 | — | — | 18.96 | 18.94 |
| — | 19.23 | — | 19.18 | — | — |
| — | — | 19.36 | — | — | — |
| 19.40 | — | 19.57 | 19.56 | — | — |
| — | — | — | 19.76 | 19.71 | 19.60 |
| 19.80 | — | 19.86 | — | — | — |
| 20.04 | — | — | — | 19.94 | — |
| — | — | 20.24 | — | 20.23 | 20.18 |
| — | 20.50 | 20.53 | — | — | — |
| — | 20.80 | — | 20.83 | — | 20.75 |
| — | — | 20.95 | — | 20.97 | — |
| 21.20 | 21.10 | 21.15 | 21.09 | 21.08 | 21.07 |
| 21.42 | 21.49 | — | 21.51 | 21.47 | 21.50 |
| — | — | — | 21.69 | 21.69 | 21.67 |
| 21.77 | 21.81 | 21.71 | — | — | — |
| — | — | 22.06 | 22.00 | 22.09 | 22.00 |
| — | 22.40 | 22.42 | 22.26 | 22.30 | — |
| 22.61 | — | — | — | — | 22.48 |
| — | 22.83 | 22.76 | 22.92 | — | — |
| — | — | — | — | 22.99 | 23.03 |
| 23.31 | — | 23.28 | 23.27 | 23.37 | — |
| — | — | — | — | — | 23.44 |
| 23.97 | 23.83 | — | 23.81 | — | 23.76 |
| 24.19 | — | — | 24.18 | 24.14 | — |
| 24.37 | 24.38 | 24.36 | — | — | 24.36 |
| — | — | — | 24.52 | 24.53 | — |
| 24.78 | — | — | 24.68 | 24.69 | 24.74 |
| — | — | 24.85 | — | — | — |
| — | 25.07 | — | — | — | — |
| — | — | 25.22 | 25.19 | 25.22 | 25.24 |
| — | — | 25.47 | — | 25.47 | — |
| 25.73 | — | — | — | — | 25.60 |
| — | — | — | 25.90 | 25.81 | — |
| — | 26.06 | — | — | — | — |
| — | — | — | 26.24 | — | 26.23 |
| — | — | — | 26.32 | 26.37 | — |
| — | — | — | — | — | 26.50 |
| — | — | — | 26.70 | — | — |
| — | 26.80 | — | — | — | — |
| — | — | — | 27.08 | — | 27.00 |
| — | — | — | — | 27.20 | — |
| 27.25 | — | 27.29 | — | — | — |
| — | 27.81 | — | — | — | — |
| — | — | — | 27.50 | 27.58 | — |
| — | — | — | 27.99 | — | — |
| — | — | — | — | 28.04 | — |
| — | — | 28.21 | — | — | 28.23 |
| — | — | — | — | 28.44 | — |
| 28.76 | — | — | 28.67 | — | — |
| — | — | 28.80 | 28.90 | — | 28.91 |
| — | 29.06 | — | — | — | — |
| — | — | — | 29.23 | 29.17 | 29.21 |
| 29.29 | — | 29.31 | 29.37 | 29.38 | — |
| — | 29.76 | — | 29.79 | — | — |
| — | — | — | — | 29.83 | — |
| — | — | 30.04 | — | — | 30.09 |
| — | — | — | 30.17 | — | — |
| — | — | — | — | 30.29 | — |
| — | 30.47 | 30.42 | — | — | — |

-continued

| Angle 2θ (°) | | | | | |
|---|---|---|---|---|---|
| 30.85 | — | — | — | — | 30.94 |
| — | 31.04 | — | — | — | — |
| — | — | — | 31.23 | — | — |
| — | — | 31.47 | 31.54 | 31.38 | 31.48 |
| — | — | — | — | 31.73 | — |
| — | — | 31.99 | 31.83 | — | 31.97 |
| — | — | — | — | 32.17 | — |
| — | — | — | 32.43 | — | — |
| 32.89 | 32.87 | — | — | — | — |
| — | — | 33.06 | 33.12 | — | — |
| 33.41 | 33.53 | — | — | — | — |
| — | — | — | 33.64 | — | 33.60 |
| 33.87 | — | — | — | — | — |
| — | — | — | — | — | 33.99 |
| — | — | — | — | 34.16 | — |
| — | 34.46 | 34.50 | 34.56 | — | 34.55 |
| 34.60 | — | — | — | — | — |
| — | — | — | — | 34.82 | — |
| — | — | — | — | — | 34.96 |
| — | — | — | — | 35.12 | — |
| — | — | 35.22 | 35.21 | — | — |
| — | 35.29 | — | — | — | — |
| — | — | — | 35.59 | — | 35.54 |
| — | 35.89 | — | — | — | 35.88 |
| — | — | 36.23 | — | 36.19 | — |
| — | 36.55 | — | — | — | — |
| 36.69 | — | — | — | — | — |
| — | — | — | 36.90 | 36.86 | — |
| — | — | 37.02 | — | — | — |
| — | — | — | 37.25 | 37.28 | — |
| 37.41 | — | — | — | — | 37.41 |
| — | — | 37.65 | — | 37.69 | — |
| 38.53 | 38.66 | — | 38.58 | — | 38.54 |
| 39.28 | — | — | — | — | — |
| — | — | 39.48 | 39.59 | — | 39.42 |
| — | — | — | — | 38.67 | — |
| XRPD in FIG. 16 | 17 | 18 | 19 | 20 | 21 |

2. The crystalline form of vilanterol trifenatate according to claim 1, characterised by a thermogravimetric analysis (TGA) profile having one or more consecutive sample weight losses below 100 degrees Celsius, wherein each sample weight loss is either (a) less than 2 weight %; or (b) at least 20 weight %.

3. The crystalline form of vilanterol trifenatate according to claim 1, characterised by having a purity by HPLC of more than 99.9%.

4. The crystalline form of vilanterol trifenatate according to claim 1, characterised by comprising less than 0.15%, by area of HPLC of Impurity A.

5. The crystalline form II of vilanterol trifenatate according to claim 1 further characterized by one or more of the following:
(a) a DSC profile having an endothermic event with onset at 64° C. and peak at 72° C. and a degradation event with onset at 189° C. and peak at 191° C.;
(b) a TGA profile having a weight loss of 1.13%;
(c) a ratio of vilanterol trifenatate:water of 1:0.57;
(d) $^{13}$C CP-DD/MAS-TOSS and $^{13}$C CP-DD/MAS-TOSS with Dipolar Dephasing comprising the characteristic chemical shift (±0.218 ppm): 182.35, 171.24, 169.06, 154.47, 152.51, 146.19, 143.36, 36.17, 134.43, 133.12, 130.50, 127.67, 126.15, 124.62;
(e) $^{15}$N CP-DD/MAS shown in FIG. 5;
defined according to the European Pharmacopoeia as not hygroscopic.

6. The crystalline form III of vilanterol trifenatate according to claim 1 further characterized by one or more of the following:
(a) a DSC profile having a endothermic event with onset at 67° C. and peak at 79° C. and a degradation event with onset at 189° C. and peak at 191° C.;
(b) a TGA profile having a two consecutive poor weight loss of approx. 0.32% and 0.54%;
(c) a ratio of vilanterol trifenatate:water of 1:0.37;
(d) defined according to the European Pharmacopoeia as slightly hygroscopic.

7. The crystalline form of vilanterol trifenatate according to claim 1, preparable by:
(a) providing vilanterol trifenatate form I

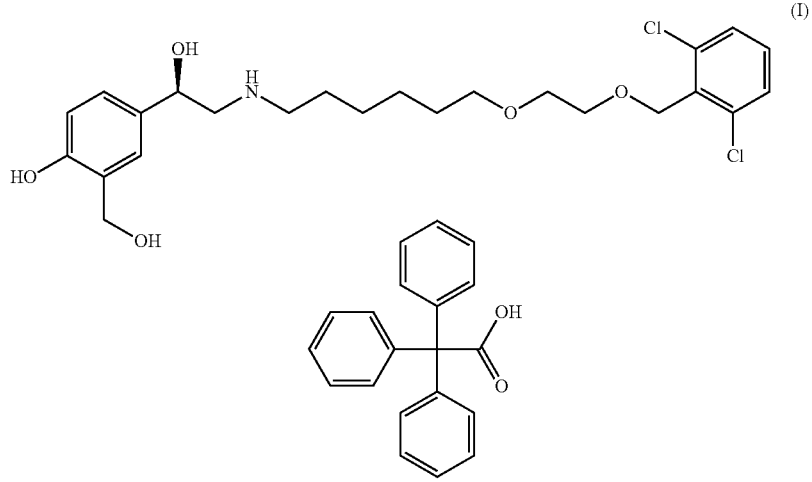 [SMILES: OCc1cc([C@@H](O)CNCCCCCCOCCOCc2c(Cl)cccc2Cl)ccc1O ; O=C(O)C(c1ccccc1)(c1ccccc1)c1ccccc1]

and cystallising from a mixture of acetone and water in a ratio in the range of from about 5:1 to 10:1 by volume; and, optionally, (b) converting the form II and/or III thus prepared to another form of vilanterol trifenatate by crystallising from a solvent or solvent system selected from the group consisting of: heptane, cyclohexane, methylcyclohexane, 2-propanol, 3-methyl-1-butanol, anisole, nitromethane, cyclohexane/ethanol (50:50), cyclihexane/2-methyltetrahydrofuran (50:50), heptane/dimethoxyethane (DME) (50:50), cyclohexane:methylketone (50:50) and methyl cyclohexane.

8. The crystalline form of vilanterol trifenatate according to claim 1, preparable by:
(a) providing vilanterol trifenatate form I Or
c1) suspending vilanterol trifenatate form I in acetone,
c2) heating the suspension,
c3) adding water, to the solution obtained in step c2),
c4) cooling down the solution obtained in step c3), optionally at a rate about 10° C./hour and, optionally,
c5) adding a seed of crystalline form III, and
c6) isolating crystalline form III, optionally under reduced pressure, followed by drying or optionally by spray drying the suspension;

Or
d1) suspending vilanterol trifenatate form II in heptane,
d2) heating the suspension, optionally at a rate about 20° C./hour and optionally with stirring,
d3) cooling down the suspension, optionally at a rate about 20° C./hour and optionally with stirring, and, and cystallising from a mixture of acetone and water in a ratio in the range of from about 30:3 by volume; and, optionally, (b) converting the form II thus prepared to (i) another form of vilanterol trifenatate and/or (ii) to form III, by adding further water.

9. A process for the preparation of crystalline form II of vilanterol trifenatate according to claim 1, comprising the steps of:
a1) suspending vilanterol trifenatate form I in acetone,
a2) heating the suspension, optionally with stirring,
a3) adding water, optionally with stirring,
a4) cooling down the obtained solution, optionally at a rate of about 10° C./hour and, optionally, a5) adding a seed of crystalline form II, and
a6) isolating new crystalline form II, optionally under reduced pressure, followed by drying, optionally by spray drying, the resulting suspension.

10. The process for the preparation of crystalline form III of vilanterol trifenatate according to claim 1, comprising the steps of:
Either
b1) suspending vilanterol trifenatate forms II and III in water, optionally at 20-25° C. and optionally with stirring, and
b2) isolating crystalline form III, optionally under reduced pressure, followed by drying, optionally by spray drying the suspension;

optionally d4) heating the suspension, optionally at a rate about 10° C./hour and optionally with stirring, cooling down the suspension optionally at a rate about 10° C./hour and optionally with stirring, heating the suspension, optionally at a rate about 5° C./hour and optionally with stirring, cooling down the suspension, optionally at a rate about 5° C./hour and optionally with stirring, d5) heating the suspension, optionally at a rate of about 10° C./hour and optionally with stirring, and d6) isolating new crystalline form III, optionally under reduced pressure, followed by drying, optionally by spray drying, the suspension.

11. The process for the preparation of a crystalline form of vilanterol trifenatate defined in claim 1, comprising:
either
suspending vilanterol trifenatate form II in a solvent, undertaking one or more cycles of heating and cooling, optionally with stirring, and isolating the crystalline form, optionally under reduced pressure, followed by drying, optionally by spray drying, the suspension, wherein the solvent is, (a) for the preparation of form IV, cyclohexane;
(b) for the preparation of form V, methylcyclohexane;
(c) for the preparation of form VI, 2-propanol;
(d) for the preparation of form VII, 3-methyl-1-butanol;
(e) for the preparation of form VIII, anisole;
for the preparation of form IX, nitromethane;
(g) for the preparation of form X, a binary mixture of cyclohexane:ethanol or of heptane:ethanol;

(h) for the preparation of form XI, a binary mixture of cyclohexane:2-methyltetrahydrofuran;
(i) for the preparation of form XII, a binary mixture of heptane: 1,2-dimethoxyethane;
(j) for the preparation of form XIII, a binary mixture of cyclohexane:methylethylketone or of heptane:methylethylketone or of mesitylene:methylethylketone;

or suspending vilanterol trifenatate form III in methylcyclohexane, undertaking one or more cycles of heating and cooling, optionally with stirring, and isolating the crystalline form, optionally under reduced pressure, followed by drying, optionally by spray drying, the suspension.

12. The process according to claim 9, wherein the crystallization step further comprises controlling the particle size of the vilanterol trifenatate, optionally by micronisation of the vilanterol trifenatate.

13. The process according to claim 9, further comprising the step of isolating vilanterol trifenatate in the form of powder.

14. Vilanterol trifenatate obtainable from the process according to claim 7.

15. Vilanterol trifenatate according to claim 14, wherein the vilanterol trifenatate is suitable for administration by inhalation having a particle size distribution of Dv90 below 10 μm.

16. A vilanterol trifenatate crystalline form according to claim 1 formulated for the treatment of COPD or asthma.

17. A pharmaceutical composition comprising the vilanterol trifenatate crystalline form according to claim 1 in association with a pharmaceutically acceptable carrier therefor and optionally one or more additional active pharmaceutical ingredient(s).

18. The pharmaceutical composition according to claim 17 in a form suitable for inhalation, optionally in the form of micronized powders, having a particle size suitable for inhalation, which powdered form is optionally deliverable from foil-wrapped blisters.

* * * * *